US009951277B2

(12) United States Patent
Takata et al.

(10) Patent No.: US 9,951,277 B2
(45) **Date of Patent: *Apr. 24, 2018**

(54) LIQUID CRYSTAL COMPOUND HAVING 1,1,3,3-TETRAFLUOROALLYLOXY GROUP, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Akihiro Takata, Chiba (JP); Takahiro Kubo, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/121,383

(22) PCT Filed: Feb. 19, 2015

(86) PCT No.: PCT/JP2015/054570

§ 371 (c)(1),
(2) Date: Aug. 25, 2016

(87) PCT Pub. No.: WO2015/129540

PCT Pub. Date: Sep. 3, 2015

(65) Prior Publication Data

US 2016/0362605 A1 Dec. 15, 2016

(30) Foreign Application Priority Data

Feb. 25, 2014 (JP) ................................ 2014-033987

(51) Int. Cl.

| | |
|---|---|
| ***G02F 1/1333*** | (2006.01) |
| ***C09K 19/34*** | (2006.01) |
| ***C09K 19/20*** | (2006.01) |
| ***C07C 43/225*** | (2006.01) |
| ***C07D 213/30*** | (2006.01) |
| ***C07D 239/26*** | (2006.01) |
| ***C07D 309/06*** | (2006.01) |
| ***C07D 319/06*** | (2006.01) |

(Continued)

(52) U.S. Cl.

CPC ........ *C09K 19/3458* (2013.01); *C07C 43/225* (2013.01); *C07D 213/30* (2013.01); *C07D 239/26* (2013.01); *C07D 309/06* (2013.01); *C07D 319/06* (2013.01); *C07D 405/04* (2013.01); *C07D 493/08* (2013.01); *C09K 19/20* (2013.01); *C09K 19/3028* (2013.01);

(Continued)

(58) Field of Classification Search

CPC ................ C09K 19/3458; C09K 19/20; C09K 19/3028; C09K 2019/0444; C09K 2019/0466; C09K 2019/123; C09K 2019/124; C09K 2019/301; C09K 2019/3016; C09K 2019/3019; C09K 2019/3025; C09K 2019/3077; C09K 2019/308; C09K 2019/3083; C09K 2019/3422; G02F 1/1333; C07C 43/225; C07C 2101/14; C07D 213/30; C07D 239/26; C07D 309/06; C07D 319/06; C07D 405/04; C07D 493/08

USPC .............. 252/299.01, 299.6, 299.61; 428/1.1

See application file for complete search history.

(56) References Cited

U.S. PATENT DOCUMENTS 7,001,647 B2 * 2/2006 Shinano .............. C07D 239/04 252/299.61
2005/0161637 A1 7/2005 Shinano et al.

(Continued)

FOREIGN PATENT DOCUMENTS

JP 2007277127 10/2007
JP 2013014575 1/2013

(Continued)

OTHER PUBLICATIONS

"International Search Report (Form PCT/ISA/210)", dated May 12, 2015, with English translation thereof, pp. 1-5.

*Primary Examiner* — Geraldina Visconti
(74) *Attorney, Agent, or Firm* — JCIPRNET

(57) ABSTRACT

To show a liquid crystal compound satisfying at least one of physical properties such as a high stability to heat, light or the like, a high clearing point, a low minimum temperature of a liquid crystal phase, a small viscosity, a suitable optical anisotropy, a large dielectric anisotropy, a suitable elastic constant and an excellent compatibility with other liquid crystal compounds, a liquid crystal composition containing the compound and a liquid crystal display device including the composition.

A compound represented by formula (1):

(1)

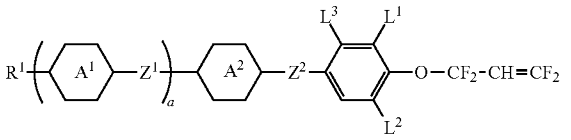

wherein, in formula (1), for example, $R^1$ is alkyl having 1 to 15 carbons;

ring $A^1$ and ring $A^2$ are 1,4-cyclohexylene, 1,4-cyclohexenylene, 1,4-phenylene, 1,4-phenylene in which at least one piece of hydrogen is replaced by halogen, tetrahydropyran-2,5-diyl or 1,3-dioxane-2,5-diyl; $Z^1$ and $Z^2$ are a single bond or $—CF_2O—$; $L^1$, $L^2$ and $L^3$ are halogen or hydrogen; and a is 0 to 3.

14 Claims, No Drawings

(51) Int. Cl.

| | |
|---|---|
| ***C07D 405/04*** | (2006.01) |
| ***C07D 493/08*** | (2006.01) |
| *C09K 19/04* | (2006.01) |
| *C09K 19/12* | (2006.01) |
| *C09K 19/30* | (2006.01) |

(52) U.S. Cl.

CPC .. *C07C 2101/14* (2013.01); *C09K 2019/0444* (2013.01); *C09K 2019/0466* (2013.01); *C09K 2019/123* (2013.01); *C09K 2019/124* (2013.01); *C09K 2019/301* (2013.01); *C09K 2019/308* (2013.01); *C09K 2019/3016* (2013.01); *C09K 2019/3019* (2013.01); *C09K 2019/3025* (2013.01); *C09K 2019/3077* (2013.01); *C09K 2019/3083* (2013.01); *C09K 2019/3422* (2013.01)

(56) References Cited

U.S. PATENT DOCUMENTS

2017/0044435 A1* 2/2017 Matsuda ............ C09K 19/3402
2017/0051205 A1* 2/2017 Matsuda ............ C09K 19/3402

FOREIGN PATENT DOCUMENTS

JP 2013221011 10/2013
WO 2004058676 7/2004

* cited by examiner

LIQUID CRYSTAL COMPOUND HAVING 1,1,3,3-TETRAFLUOROALLYLOXY GROUP, LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2015/054570, filed on Feb. 19, 2015, which claims the priority benefit of Japan application no. 2014-033987, filed on Feb. 25, 2014. The entirety of each of the above-mentioned patent applications is hereby incorporated by reference herein and made a part of this specification.

TECHNICAL FIELD

The invention relates to a liquid crystal compound, a liquid crystal composition and a liquid crystal display device. More specifically, the invention relates to a liquid crystal compound having a 1, 1, 3,3-tetrafluoroallyloxy group, a liquid crystal composition that contains the compound and has a nematic phase, and a liquid crystal display device including the composition.

A liquid crystal display device has been widely utilized for a display of a personal computer, a television and so forth. The device utilizes optical anisotropy, dielectric anisotropy and so forth of a liquid crystal compound. As an operating mode of the liquid crystal display device, such modes are known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the liquid crystal display device, a liquid crystal compound contained in the composition preferably has physical properties described in (1) to (8) below.

(1) High stability to heat, light or the like, (2) a high clearing point, (3) a low minimum temperature of a liquid crystal phase, (4) a small viscosity (η), (5) a suitable optical anisotropy (Δn), (6) a large dielectric anisotropy (Δ∈), (7) a suitable elastic constant (K), and (8) an excellent compatibility with other liquid crystal compounds.

An effect of the physical properties of the liquid crystal compound on the characteristics of the device is as described below. A compound having the high stability to heat, light and so forth as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase as described in (3), in particular, a compound having the low minimum temperature of the nematic phase, also extends a temperature range in which the device can be used. A compound having the small viscosity as described in (4) shortens a response time of the device.

A compound having a suitable optical anisotropy as described in (5) improves a contrast of the device. According to a design of the device, a compound having a large optical anisotropy or a small optical anisotropy, more specifically, a compound having the suitable optical anisotropy is required. When the response time is shortened by decreasing a cell gap of the device, a compound having the large optical anisotropy is suitable. A compound having a large dielectric anisotropy as described in (6) decreases a threshold voltage of the device. Thus, an electric power consumption of the device is reduced. On the other hand, a compound having a small dielectric anisotropy shortens the response time of the device by decreasing viscosity of the composition.

With regard to (7), a compound having a large elastic constant shortens the response time of the device. A compound having a small elastic constant decreases the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing liquid crystal compounds having different physical properties. In general, compatibility of a compound becomes lower as the temperature becomes lower. Accordingly, the compound having the excellent compatibility is also required even at a low temperature.

A variety of liquid crystal compounds having the excellent compatibility with other liquid crystal compounds have been so far prepared. On Patent literature No. 2, compound (S-1) having perfluoroallyloxy is described.

However, the compound has no sufficiently high stability to heat, and has no sufficiently high compatibility also at low temperature.

(S-1)

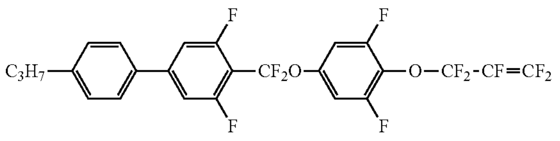

In view of such a situation, development has been desired for a compound having excellent properties with regard to characteristics (1) to (8) described above, particularly for a compound having excellent stability and compatibility, and having a large dielectric anisotropy.

CITATION LIST

Patent Literature

Patent literature No. 1: WO 2004/058676 A.

Patent literature No. 2: JP 2007-277127 A.

SUMMARY OF INVENTION

Technical Problem

The invention provides a liquid crystal compound satisfying at least one of physical properties such as a high stability to heat and light, a high clearing point, a low minimum temperature of a liquid crystal phase, a small viscosity, a suitable optical anisotropy, a large dielectric anisotropy, a suitable elastic constant and an excellent compatibility with other liquid crystal compounds. In particular, the invention provides a compound being excellent in stability and compatibility and having a large dielectric anisotropy. The invention also provides a liquid crystal composition that contains the compound and satisfies at least one of physical properties such as a high maximum temperature of a nematic phase, a low minimum temperature of the nematic phase, a small viscosity, a suitable optical anisotropy, a large dielectric anisotropy and a suitable elastic constant. The invention provides a liquid crystal composition having a suitable balance regarding at least two of physical properties. The invention further provides a liquid crystal display device that includes the composition, and has a wide temperature range in which the device can be used, a short response time, a large voltage holding ratio, a low threshold voltage, a large contrast ratio and a long service life.

Solution to Problem

The invention concerns a liquid crystal compound represented by formula (1), a liquid crystal composition containing the compound, and a liquid crystal display device including the composition:

(1)

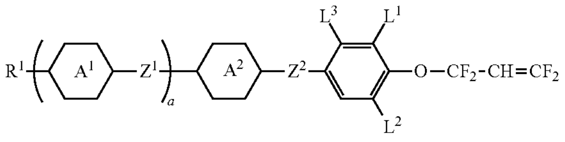

wherein, in formula (1), $R^1$ is alkyl having 1 to 15 carbons, and in the alkyl, at least one piece of $-CH_2-$ may be replaced by $-O-$, and at least one piece of $-CH_2CH_2-$ may be replaced by $-CH{=}CH-$, and in the groups, at least one piece of hydrogen may be replaced by halogen;

ring $A^1$ and ring $A^2$ are independently 1,4-cyclohexylene, 1,4-cyclohexenylene, 1,4-phenylene, 1,4-phenylene in which at least one piece of hydrogen is replaced by halogen, tetrahydropyran-2,5-diyl, 1,3-dioxane-2,5-diyl, 2,6,7-trioxabicyclo[2.2.2]octane-1,4-diyl, pyrimidine-2, 5-diyl or pyridine-2, 5-diyl;

$Z^1$ and $Z^2$ are independently a single bond, $-CH_2CH_2-$, $-C{\equiv}C-$, $-CH{=}CH-$, $-CF{=}CF-$, $-CF_2O-$, $-OCF_2-$, $-CH_2O-$, $-OCH_2-$, $-COO-$ or $-OCO-$;

$L^1$, $L^2$ and $L^3$ are independently hydrogen or halogen; and a is 0, 1, 2 or 3.

Advantageous Effects of Invention

A first advantage of the invention is to provide a liquid crystal compound satisfying at least one of physical properties such as a high stability to heat and light, a high clearing point, a low minimum temperature of a liquid crystal phase, a small viscosity, a suitable optical anisotropy, a large dielectric anisotropy, a suitable elastic constant and an excellent compatibility with other liquid crystal compounds. In particular, the advantage is to provide a compound being excellent in stability and compatibility and having a large dielectric anisotropy. A second advantage is to provide a liquid crystal composition that contains the compound and satisfies at least one of physical properties such as a high maximum temperature of a nematic phase, a low minimum temperature of the nematic phase, a small viscosity, a suitable optical anisotropy, a large dielectric anisotropy and a suitable elastic constant. A third advantage is to provide a liquid crystal display device that includes the composition, and has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase and a smectic phase, and a compound having no liquid crystal phase but to be added for the purpose of adjusting physical properties of a composition such as a maximum temperature, a minimum temperature, viscosity and a dielectric anisotropy. The compound has a six-membered ring such as 1,4-cyclohexylene and 1,4-phenylene, and has rod-like molecular structure. A liquid crystal composition is prepared by mixing such liquid crystal compounds. A proportion (content) of the liquid crystal compounds is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the composition when necessary. A proportion (amount of addition) of the additive is expressed in terms of weight percent (% by weight) based on the weight of the liquid crystal composition in a manner similar to the proportion of the liquid crystal compounds. Weight parts per million (ppm) may be occasionally used. A liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as "maximum temperature." A minimum temperature of the nematic phase may be occasionally abbreviated as "minimum temperature."

A compound represented by formula (1) may be occasionally abbreviated as "compound (1)." The abbreviation applies also to a compound represented by formula (2) or the like. In formula (1) to formula (15), a symbol $A^1$, $B^1$, $C^1$ or the like surrounded by a hexagonal shape corresponds to ring $A^1$, ring $B^1$ and ring $C^1$, respectively. A symbol of terminal group $R^{11}$ is used in a plurality of compounds. In the compounds, two groups represented by two pieces of arbitrary $R^{11}$ may be identical or different. For example, in one case, $R^{11}$ of compound (2) is ethyl and of compound (3) is ethyl. In another case, $R^{11}$ of compound (2) is ethyl and $R^{11}$ of compound (3) is propyl. A same rule applies also to a symbol such as any other terminal group and a ring. In formula (5), when i is 2, two of rings $C^1$ exists. In the compound, two groups represented by two of rings $C^1$ may be identical or different. A same rule applies also to arbitrary two when i is larger than 2. A same rule applies also to a symbol such as any other ring and a bonding group.

An expression "at least one piece of "A" may be replaced by "B"" means that, when the number of "A" is 1, a position of "A" is arbitrary, and also when the number of "A" is 2 or more, positions thereof can be selected without restriction. An expression "at least one piece of A may be replaced by B, C or D" includes a case where arbitrary A is replaced by B, a case where arbitrary A is replaced by C, and a case where arbitrary A is replaced by D, and also a case where a plurality of pieces A are replaced by at least two of B, C and D. For example, alkyl in which at least one piece of —$CH_2$— may be replaced by —O— or —CH═CH— includes alkyl, alkenyl, alkoxy, alkoxyalkyl, alkoxyalkenyl and alkenyloxyalkyl. In addition, a case where replacement of two consecutive pieces of —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Then, 2-fluoro-1,4-phenylene means two divalent groups described below. In a chemical formula, fluorine may be leftward (L) or rightward (R). A same rule applies also to an asymmetrical divalent ring such as tetrahydropyran-2,5-diyl.

(L)

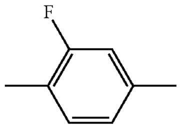

(R)

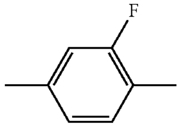

The invention includes contents described in items 1 to 14 below.

Item 1. A compound, represented by formula (1):

(1)

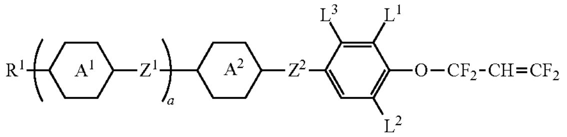

wherein, in formula (1), $R^1$ is alkyl having 1 to 15 carbons, and in the alkyl, at least one piece of —$CH_2$— may be replaced by —O—, and at least one piece of —$CH_2CH_2$— may be replaced by —CH═CH—, and in the groups, at least one piece of hydrogen may be replaced by halogen;

ring $A^1$ and ring $A^2$ are independently 1,4-cyclohexylene, 1,4-cyclohexenylene, 1,4-phenylene, 1,4-phenylene in which at least one piece of hydrogen is replaced by halogen, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl;

$Z^1$ and $Z^2$ are independently a single bond, —$CH_2CH_2$—, —C≡C—, —CH═CH—, —CF═CF—, —$CF_2O$—, —$OCF_2$—, —$CH_2O$—, —$OCH_2$—, —COO— or —OCO—;

$L^1$, $L^2$ and $L^3$ are independently hydrogen or halogen; and a is 0, 1, 2 or 3.

Item 2. The compound according to item 1, wherein, in formula (1) described in item 1, $R^1$ is alkyl having 1 to 15 carbons, alkenyl having 2 to 15 carbons, alkoxy having 1 to 14 carbons or alkenyloxy having 2 to 14 carbons.

Item 3. The compound according to item 1 or 2, wherein, in formula (1) described in item 1, $Z^1$ and $Z^2$ are independently a single bond, —$CH_2CH_2$—, —C≡O—, —CH═CH—, —$CF_2O$— or —COO—.

Item 4. The compound according to item 1, represented by any one of formulas (1-1) to (1-4):

(1-1)

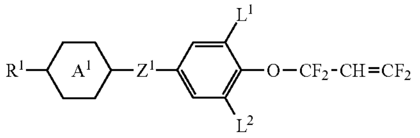

(1-2)

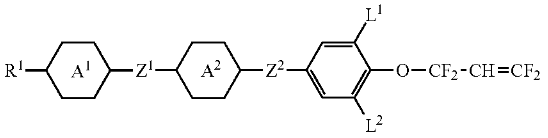

(1-3)

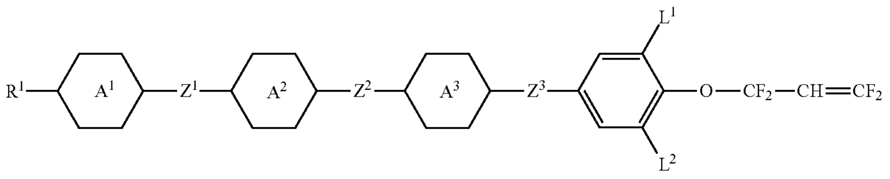

(1-4)

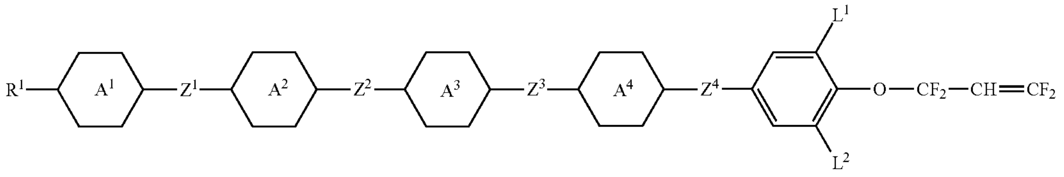

wherein, in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by halogen, tetrahydropyran-2,5-diyl, 1,3-dioxane-2,5-diyl or 2,6,7-trioxabicyclo[2.2.2]octane-1,4-diyl;

$Z^1$, $Z^2$, $Z^3$ and $Z^4$ are independently a single bond, $-CH_2CH_2-$, $-CH{=}CH-$, $-CF_2O-$ or $-COO-$;

$R^1$ is alkyl having 1 to 10 carbons or alkenyl having 2 to 10 carbons; and $L^1$ and $L^2$ are independently hydrogen or halogen.

Item 5. The compound according to item 1, wherein, in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by fluorine or chlorine, tetrahydropyran-2,5-diyl or 1,3-dioxane-2,5-diyl;

$Z^1$, $Z^2$, $Z^3$ and $Z^4$ are independently a single bond, $-CH_2CH_2-$, $-CH{=}CH-$ or $-CF_2O-$;

$R^1$ is alkyl having 1 to 10 carbons or alkenyl having 2 to 10 carbons; and $L^1$ and $L^2$ are independently hydrogen or fluorine.

(1-1)

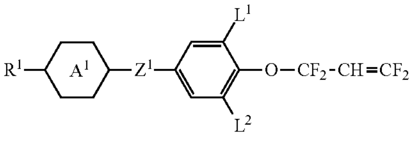

(1-2)

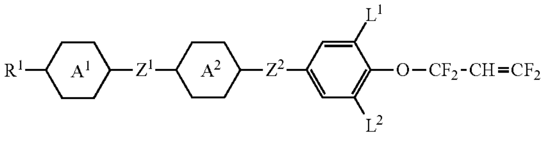

(1-3)

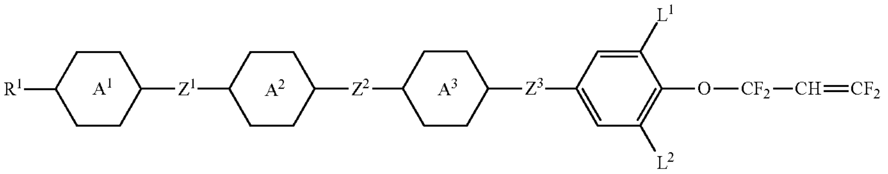

(1-4)

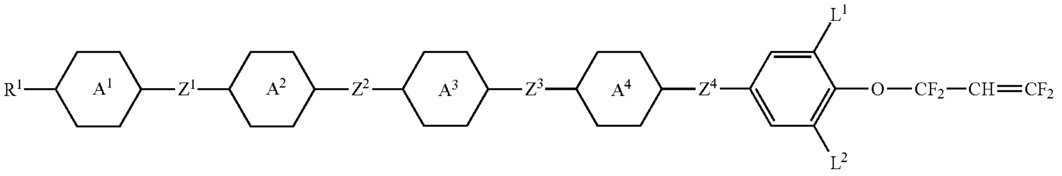

Item 6. The compound according to item 1, represented by any one of formulas (1-5) to (1-12)

(1-5)

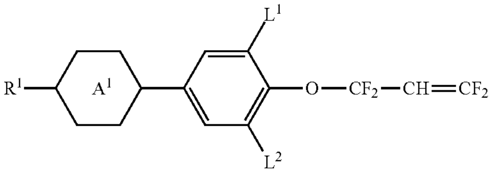

(1-6)

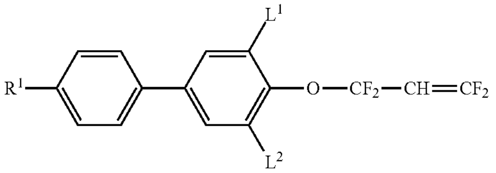

(1-7)

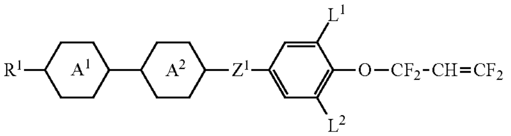

(1-8)

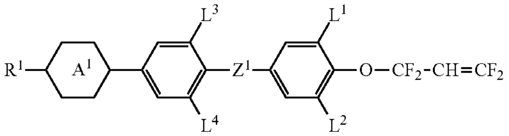

(1-9)

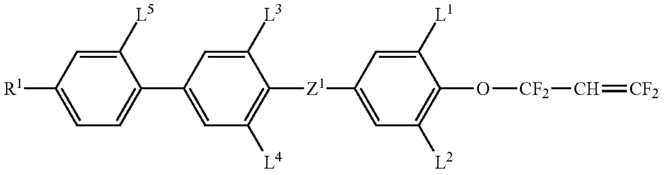

-continued (1-10)

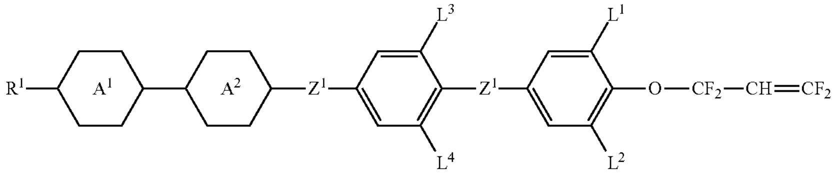

(1-11)

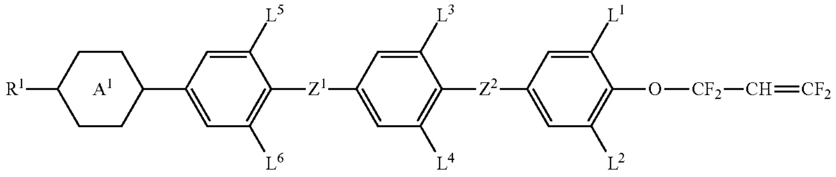

(1-12)

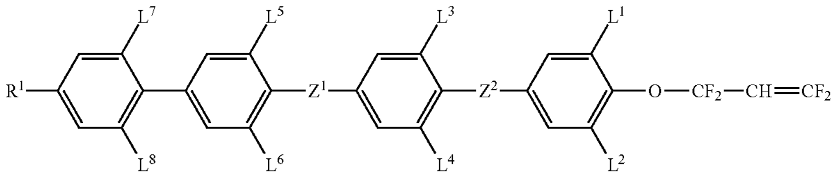

wherein, in formulas (1-5) to (1-12), ring $A^1$ and ring $A^2$ are independently 1,4-cyclohexylene, tetrahydropyran-2,5-diyl or 1,3-dioxane-2,5-diyl;

$Z^1$ and $Z^2$ are independently a single bond or $-CF_2O-$;

$R^1$ is alkyl having 1 to 10 carbons or alkenyl having 2 to 10 carbons; and $L^1$, $L^2$, $L^3$, $L^4$, $L^5$, $L^6$, $L^7$ and $L^8$ are independently hydrogen or fluorine.

Item 7. The compound according to item 1, represented by any one of formulas (1-13) to (1-23):

(1-13)

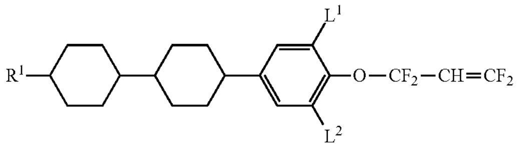

(1-14)

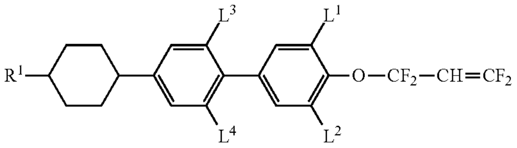

(1-15)

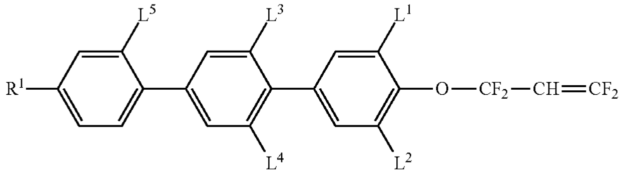

(1-16)

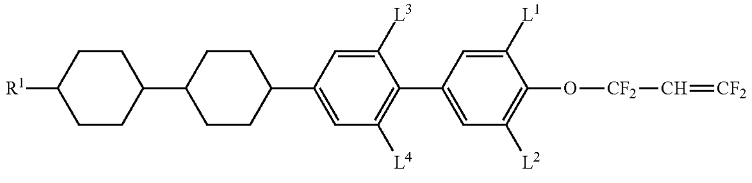

-continued (1-17)

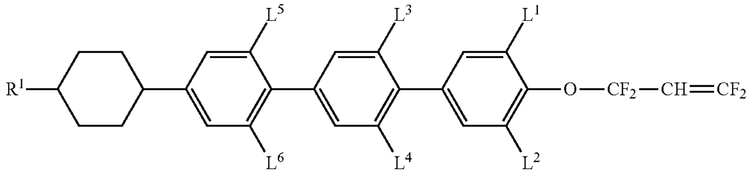

(1-18)

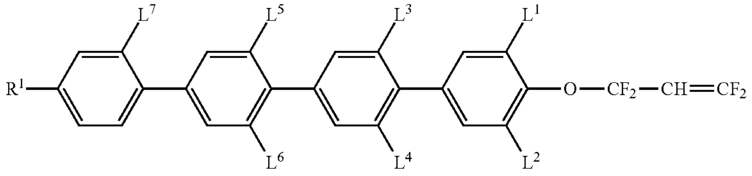

(1-19)

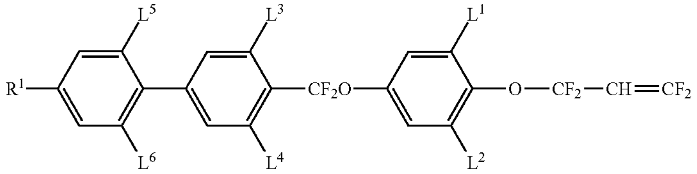

(1-20)

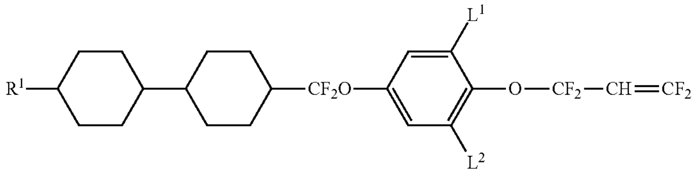

(1-21)

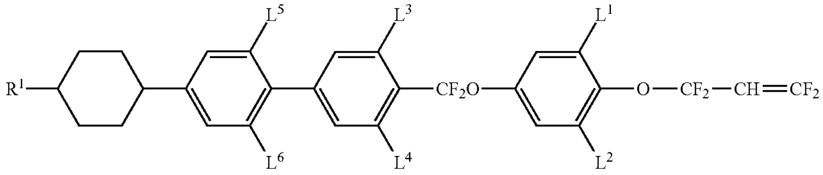

(1-22)

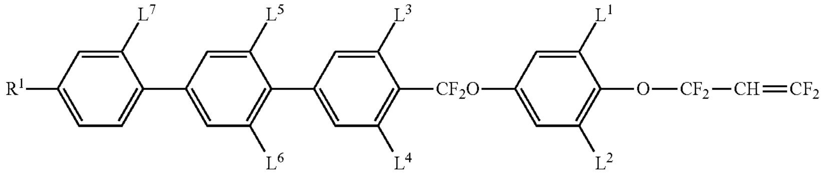

(1-23)

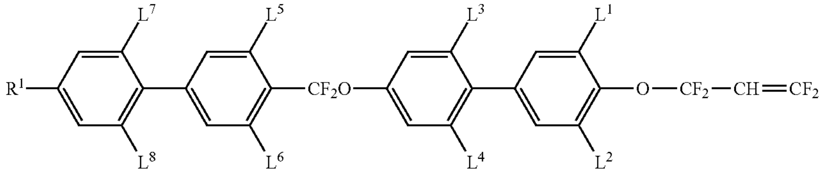

wherein, in formulas (1-13) to (1-23), $R^1$ is alkyl having 1 to 10 carbons or alkenyl having 2 to 10 carbons; and $L^1$, $L^2$, $L^3$, $L^4$, $L^5$, $L^6$, $L^7$ and $L^8$ are independently hydrogen or fluorine.

Item 8. A liquid crystal composition, containing at least one of the compounds according to any one of items 1 to 7.

Item 9. The liquid crystal composition according to item 8, further containing at least one compound selected from the group of compounds represented by formulas (2) to (4):

(2)

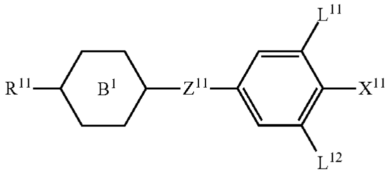

-continued (3)

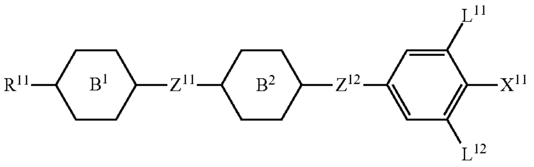

(4)

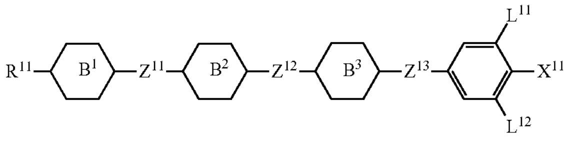

wherein, in formulas (2) to (4), $R^{11}$ is alkyl having 1 to 10 carbons or alkenyl having 2 to 10 carbons, and in the alkyl and the alkenyl, at least one piece of hydrogen may be replaced by fluorine, and at least one piece of $—CH_2—$ may be replaced by —O—;

$X^{11}$ is fluorine, chlorine, $—OCF_3$, $—OCHF_2$, $—CF_3$, $—CHF_2$, $—CH_2F$, $—OCF_2CHF_2$ or $—OCF_2CHFCF_3$;

ring $B^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, $—CH_2CH_2—$, —CH═CH—, —C≡O—, —COO—, $—CF_2O—$, $—OCF_2—$, $—CH_2O—$ or $—(CH_2)_4—$; and $L^{11}$ and $L^{12}$ are independently hydrogen or fluorine.

Item 10. The liquid crystal composition according to item 8 or 9, further containing at least one compound selected from the group of compounds represented by formula (5):

(5)

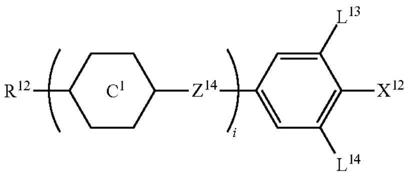

wherein, in formula (5), $R^{12}$ is alkyl having 1 to 10 carbons or alkenyl having 2 to 10 carbons, and in the alkyl and the alkenyl, at least one piece of hydrogen may be replaced by fluorine, and at least one piece of $—CH_2—$ may be replaced by —O—;

$X^{12}$ is —C≡N or —C≡C—C≡N;

ring $C^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$ is a single bond, $—CH_2CH_2—$, —C≡C—, —COO—, $—CF_2O—$, $—OCF_2—$ or $—CH_2O—$;

$L^{13}$ and $L^{14}$ are independently hydrogen or fluorine; and i is 1, 2, 3 or 4.

Item 11. The liquid crystal composition according to any one of items 8 to 10, further containing at least one compound selected from the group of compounds represented by formulas (6) to (12):

(6)

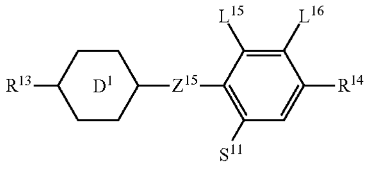

(7)

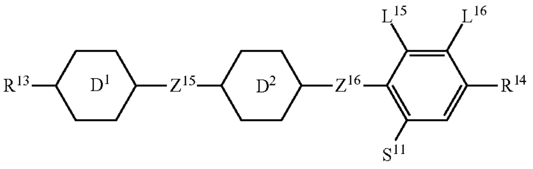

(8)

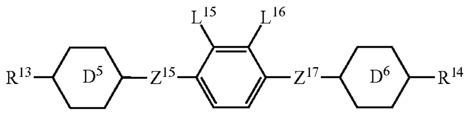

(9)

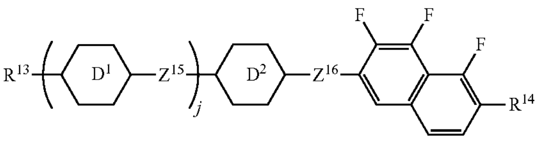

(10)

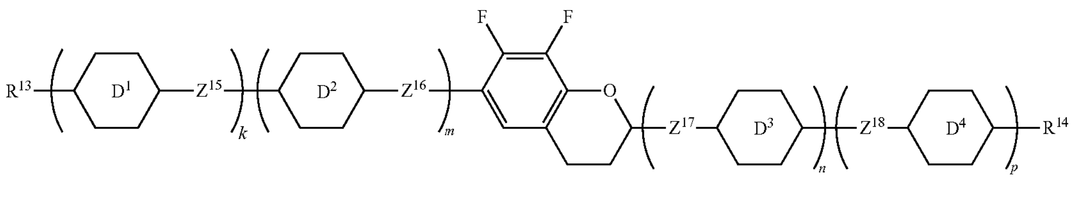

(11)

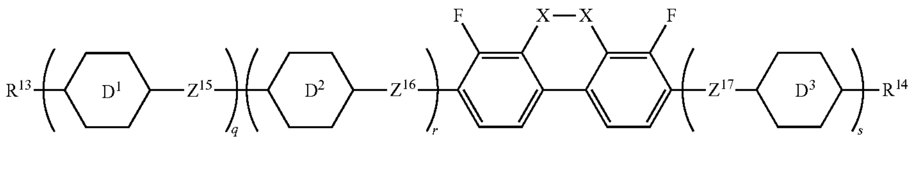

-continued (12)

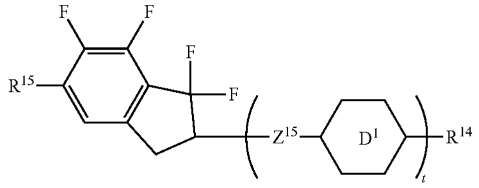

wherein, in formulas (6) to (12), $R^{13}$ and $R^{14}$ are independently alkyl having 1 to 10 carbons or alkenyl having 2 to 10 carbons, and in the alkyl and the alkenyl, at least one piece of $—CH_2—$ may be replaced by —O—, and at least one piece of hydrogen may be replaced by fluorine;

$R^{15}$ is hydrogen, fluorine, alkyl having 1 to 10 carbons or alkenyl having 2 to 10 carbons, and in the alkyl and the alkenyl, at least one piece of $—CH_2—$ may be replaced by —O—, and at least one piece of hydrogen may be replaced by fluorine;

$S^{11}$ is hydrogen or methyl;

X is $—CF_2—$, —O— or —CHF—;

ring $D^1$, ring $D^2$, ring $D^3$ and ring $D^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, $—CH_2CH_2—$, —COO—, $—CH_2O—$, $—OCF_2—$ or $—OCF_2CH_2CH_2—$;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 12. The liquid crystal composition according to any one of items 8 to 11, further containing at least one compound selected from the group of compounds represented by formulas (13) to (15):

(13)

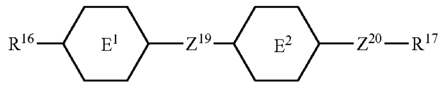

(14)

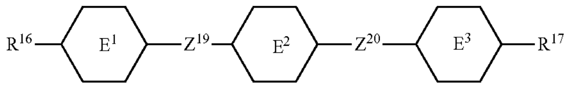

(15)

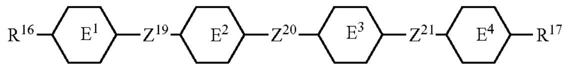

wherein, in formulas (13) to (15), $R^{16}$ and $R^{17}$ are independently alkyl having 1 to 10 carbons or alkenyl having 2 to 10 carbons, and in the alkyl and the alkenyl, at least one piece of $—CH_2—$ may be replaced by —O—, and at least one piece of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, $—CH_2CH_2—$, —CH=CH—, —C≡C— or —COO—.

Item 13. The liquid crystal composition according to any one of items 8 to 12, further containing at least one selected from a polymerizable compound, an optically active compound, an antioxidant, an ultraviolet light absorber, a light stabilizer, a heat stabilizer and an antifoaming agent.

Item 14. A liquid crystal display device, including the liquid crystal composition according to any one of items 8 to 13.

The compound, the liquid crystal composition and the liquid crystal display device according to the invention will be described in the order.

1-1. Compound (1)

Compound (1) of the invention is a compound having a 1,1,3,3-tetrafluoroallyloxy group, and therefore, particularly has a feature of having a high stability to heat, an excellent compatibility with other liquid crystal compounds, and having a large dielectric anisotropy. Preferred examples of compound (1) according to the invention will be described. Preferred examples of a terminal group, a ring structure, a bonding group and a substituent in compound (1) are also applied to a subordinate formula of formula (1) for compound (1).

(1)

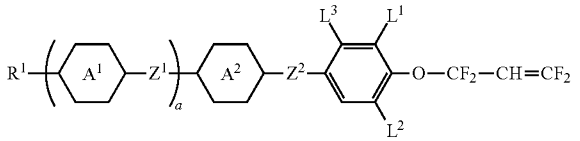

wherein, in formula (1), $R^1$ is alkyl having 1 to 15 carbons, and in the alkyl, at least one piece of $—CH_2—$ may be replaced by —O—, and at least one piece of $—CH_2CH_2—$ may be replaced by —CH=CH—, and in the groups, at least one piece of hydrogen may be replaced by halogen.

Specific examples of such a terminal group $R^1$ include alkyl, alkoxy, alkoxyalkyl, alkoxyalkoxy, alkenyl, alkenyloxy, alkenyloxyalkyl and alkoxyalkenyl. In the groups, at least one piece of hydrogen may be replaced by halogen. Preferred halogen is fluorine and chlorine. Further preferred halogen is fluorine. The groups have a straight chain or a branched chain, and include no cyclic group such as cyclohexyl. In the groups, the straight chain is preferred to the branched chain.

A preferred configuration of —CH═CH— in the alkenyl depends on a position of a double bond. A trans configuration is preferred, in alkenyl having the double bond in an odd-numbered position, such as —CH═CHCH$_3$, —CH═CHC$_2$H$_5$, —CH═CHC$_3$H$_7$, —CH═CHC$_4$H$_9$, —C$_2$H$_4$CH═CHCH$_3$ and —C$_2$H$_4$CH═CHC$_2$H$_5$. A cis configuration is preferred in alkenyl having the double bond in an even-numbered position, such as —CH$_2$CH═CHCH$_3$, —CH$_2$CH═CHC$_2$H$_5$ and —CH$_2$CH═CHC$_3$H$_7$. An alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

Specific examples of the alkyl include —CH$_3$, —C$_2$H$_5$, —C$_3$H$_7$, —C$_4$H$_9$, —C$_5$H$_{11}$, —C$_6$H$_{13}$ and —C$_7$H$_{15}$.

Specific examples of the alkoxy include —OCH$_3$, —OC$_2$H$_5$, —OC$_3$H$_7$, —OC$_4$H$_9$, —OC$_5$H$_{11}$, —OC$_6$H$_{13}$ and —OC$_7$H$_{15}$.

Specific examples of the alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Specific examples of the alkenyl include —CH═CH$_2$, —CH═CHCH$_3$, —CH$_2$CH═CH$_2$, —CH═CHC$_2$H$_5$, —CH$_2$CH═CHCH$_3$, —(CH$_2$)$_2$—CH═CH$_2$, —CH═CHC$_3$H$_7$, —CH$_2$CH═CHC$_2$H$_5$, —(CH$_2$)$_2$—CH═CHCH$_3$ and —(CH$_2$)$_3$—CH═CH$_2$.

Specific examples of the alkenyloxy include —OCH$_2$CH═CH$_2$, —OCH$_2$CH═CHCH$_3$ and —OCH$_2$CH═CHC$_2$H$_5$.

Specific examples of alkyl in which at least one piece of hydrogen is replaced by halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_2$Cl, CCl$_2$CHCl$_2$, CH$_2$CCl$_3$, —CCl$_2$CCl$_3$, —(CH$_2$)$_3$—Cl, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —(CH$_2$)$_5$—C$_1$ and —(CCl$_2$)$_5$—C$_1$.

Specific examples of alkoxy in which at least one piece of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$Cl, —OCHCl$_2$, —OCCl$_3$, —O—(CH$_2$)$_2$—Cl, —OCCl$_2$CH$_2$C$_1$, —OCCl$_2$CHCl$_2$, —OCH$_2$CCl$_3$, —O—(CH$_2$)$_3$—Cl, —O—(CCl$_2$)$_3$—Cl, —OCCl$_2$CHClCCl$_3$, —OCHCl$_2$CCl$_2$CCl$_3$, —O(CH$_2$)$_4$—Cl, —O—(CCl$_2$)$_4$—Cl, —O—(CH$_2$)$_5$—Cl and —O—(CCl$_2$)$_5$—Cl.

Specific examples of alkenyl in which at least one piece of hydrogen is replaced by halogen include —CH═CHF, —CH═CF$_2$, —CF═CHF, —CH═CHCH$_2$F, —CH═CHCF$_3$, —(CH$_2$)$_2$—CH═CF$_2$, —CH$_2$CH═CHCF$_3$, —CH═CHCF$_2$CF$_3$, —CH═CHCl, —CH═CCl$_2$, —CCl═CHCl, —CH═CHCH$_2$Cl, —CH═CHCCl$_3$, —(CH$_2$)$_2$—CH═CCl$_2$, —CH$_2$CH═CHCCl$_3$ and —CH═CHCCl$_2$CCl$_3$.

Specific preferred examples of R$^1$ include alkyl having 1 to 10 carbons, alkenyl having 2 to 10 carbons, alkoxy having 1 to 9 carbons, alkyl having 1 to 10 carbons in which one or two pieces of hydrogen are replaced by fluorine, or alkenyl having 2 to 10 carbons in which one or two pieces of hydrogen are replaced by fluorine. Further preferred examples of R$^1$ include alkyl having 1 to 7 carbons and alkenyl having 2 to 7 carbons. Most preferred examples of R$^1$ include —CH$_3$, —C$_2$H$_5$, —C$_3$H$_7$, —C$_4$H$_9$, —C$_5$H$_{11}$, —CH═CH$_2$, —CH═CHCH$_3$, —(CH$_2$)$_2$—CH═CH$_2$, —CH$_2$CH═CHC$_2$H$_5$ and —(CH$_2$)$_2$—CH═CHCH$_3$.

In formula (1), ring A$^1$ and ring A$^2$ are independently 1,4-cyclohexylene, 1,4-cyclohexenylene, 1,4-phenylene, 1,4-phenylene in which at least one piece of hydrogen is replaced by halogen, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl.

Specific preferred examples of ring A$^1$ and ring A$^2$ include 1,4-cyclohexylene, 1,4-phenylene, 1,4-phenylene in which at least one piece of hydrogen is replaced by halogen, tetrahydropyran-2,5-diyl, 1,3-dioxane-2,5-diyl and 2,6,7-trioxabicyclo[2.2.2]octane-1,4-diyl. In 1,4-cyclohexylene, a configuration of cis and trans exists. From a viewpoint of a high maximum temperature, the trans configuration is preferred. Specific preferred examples of 1,4-phenylene in which at least one piece of hydrogen is replaced by halogen include rings (A-1) to (A-17).

(A-1)

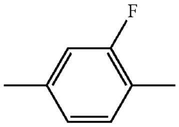

(A-2)

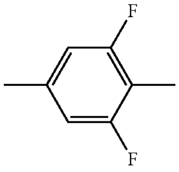

(A-3)

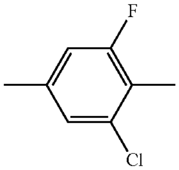

(A-4)

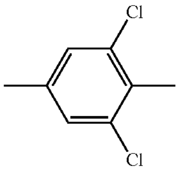

(A-5)

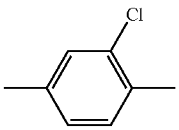

-continued (A-6)

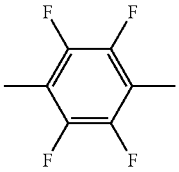

(A-7)

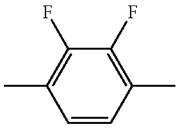

(A-8)

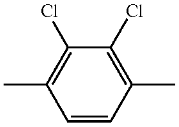

(A-9)

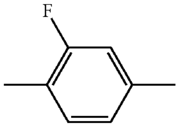

(A-10)

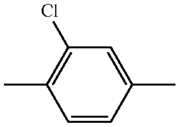

(A-11)

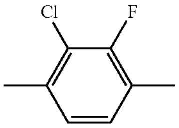

(A-12)

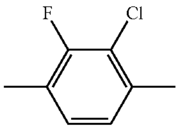

(A-13)

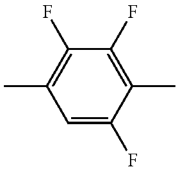

-continued (A-14)

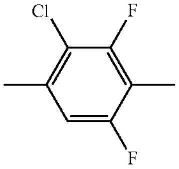

(A-15)

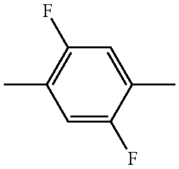

(A-16)

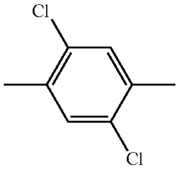

(A-17)

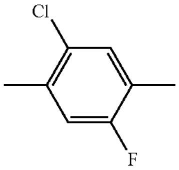

Then, 2-fluoro-1,4-phenylene is not left-right symmetric. In a chemical formula thereof, fluorine includes a case where the fluorine is located on a side of a left-terminal group (leftward) and a case where the fluorine is located on a side of a right-terminal group (rightward). Preferred 2-fluoro-1,4-phenylene is rightward (A-1) in order to increase the dielectric anisotropy. A same rule applies also to 2,6-difluoro-1,4-phenylene or the like. More specifically, rings (A-1) to (A-5) are further preferred.

Further preferred examples of 1,4-phenylene in which at least one piece of hydrogen is replaced by halogen include 2-fluoro-1,4-phenylene, 2,6-difluoro-1,4-phenylene, 2-chloro-6-fluoro-1,4-phenylene, 2,6-dichloro-1,4-phenylene and 2-chloro-1,4-phenylene. Most preferred examples of 1,4-phenylene in which at least one piece of hydrogen is replaced by halogen include 2-fluoro-1,4-phenylene and 2,6-difluoro-1,4-phenylene.

Further preferred examples of ring $A^1$ and ring $A^2$ include 1,4-cyclohexylene, 1,4-phenylene, 2-fluoro-1,4-phenylene, 2,6-difluoro-1,4-phenylene, tetrahydropyran-2,5-diyl and 1,3-dioxane-2,5-diyl.

In formula (1), $Z^1$ and $Z^2$ are independently a single bond, $-CH_2CH_2-$, $-C{\equiv}C-$, $-CH{=}CH-$, $-CF{=}CF-$, $-CF_2O-$, $-OCF_2-$, $-CH_2O-$, $-OCH_2-$, $-COO-$ or $-COO-$. Specific preferred examples of $Z^1$ and $Z^2$ include a single bond, $-CH_2CH_2-$, $-CH{=}CH-$, $-CF{=}CF-$, $-COO-$ and $-CF_2O-$. Further preferred examples of $Z^1$ and $Z^2$ include a single bond and $-CF_2O-$.

In formula (1), $L^1$, $L^2$ and $L^3$ are independently hydrogen or halogen. Preferred halogen is fluorine and chlorine. Further preferred halogen is fluorine. As for a preferred combination of $L^1$, $L^2$ and $L^3$, $L^3$ is hydrogen, one of $L^1$ and $L^2$ is hydrogen and the other is fluorine. As for a further preferred combination of $L^1$, $L^2$ and $L^3$, $L^3$ is hydrogen, and both $L^1$ and $L^2$ are fluorine.

In formula (1), a is 0, 1, 2 or 3. Preferred a is 1, 2 or 3. Further preferred a is 1 or 2. From a viewpoint of a small viscosity, preferred a is 1. From a viewpoint of a high maximum temperature, preferred a is 2.

1-2. Physical Properties of Compound (1)

In compound (1), physical properties such as a clearing point, an optical anisotropy and a dielectric anisotropy can be arbitrarily adjusted by suitably combining kinds of $R^1$, ring $A^1$, ring $A^2$, $Z^1$, $Z^2$, $L^1$, $L^2$, $L^3$ and a. Compound (1) may contain an isotope such as $^2H$ (deuterium) and $^{13}C$ in an amount larger than an amount of natural abundance because no significant difference is caused in the physical properties of the compound. A main effect of kinds of $R^1$ or the like on the physical properties of compound (1) will be described below.

When a left-terminal group $R^1$ has the straight chain, a temperature range of the liquid crystal phase is wide and the viscosity is small. When $R^1$ has the branched chain, the compatibility with other liquid crystal compounds is good. A compound in which $R^1$ is optically active is useful as a chiral dopant. A reverse twisted domain to be generated in the liquid crystal display device can be prevented by adding the compound to the composition. A compound in which $R^1$ is not optically active is useful as a component of the composition. When $R^1$ is alkenyl, a preferred configuration depends on a position of a double bond. An alkenyl compound having the preferred configuration has the small viscosity, the high maximum temperature or the wide temperature range of the liquid crystal phase.

When all of ring $A^1$ and ring $A^2$ are 1, 4-cyclohexylene, the clearing point is high and the viscosity is small. When at least one of ring $A^1$ and ring $A^2$ is 1,4-phenylene, or 1,4-phenylene in which at least one piece of hydrogen is replaced by halogen, the optical anisotropy is comparatively large and an orientational order parameter is comparatively large. When all of ring $A^1$ and ring $A^2$ are 1, 4-phenylene, 1,4-phenylene in which at least one piece of hydrogen is replaced by halogen, or a combination thereof, the optical anisotropy is particularly large. When at least one of ring $A^1$ and ring $A^2$ is 1,4-phenylene in which at least one piece of hydrogen is replaced by halogen, tetrahydropyran-2,5-diyl, pyrimidine-2,5-diyl, pyridine-2,5-diyl, 1,3-dioxane-2,5-diyl or 2,6,7-trioxabicyclo[2.2.2]octane-1, 4-diyl, the dielectric anisotropy is large.

When bonding group $Z^1$ or $Z^2$ is a single bond, $—CH_2CH_2—$, $—CH{=}CH—$ or $—CF_2O—$, the viscosity is small. When $Z^1$ or $Z^2$ is $—CH{=}CH—$ or $—CH_2O—$, the temperature range of the liquid crystal phase is wide, and an elastic constant (K) is large. When $Z^1$ or $Z^2$ is $—CH{=}CH—$ or $—C{\equiv}C—$, the optical anisotropy is large. When $Z^1$ or $Z^2$ is $—CF_2O—$ or $—COO—$, the dielectric anisotropy is large. When $Z^1$ or $Z^2$ is a single bond, $—CH_2CH_2—$, $—CF_2O—$ or $—CH_2O—$, chemical stability is high.

When $L^3$ is hydrogen and one of $L^1$ and $L^2$ is fluorine, the dielectric anisotropy is large. When $L^3$ is hydrogen and both $L^1$ and $L^2$ are fluorine, the dielectric anisotropy is particularly large, and the compatibility with other compounds is excellent.

When a is 0, the compatibility with other compounds is excellent, and the viscosity is extremely small. When a is 1, the compatibility with other compounds is excellent, the viscosity is small, and the dielectric anisotropy is large. When a is 2, the clearing point is high, the dielectric anisotropy is large, and the optical anisotropy is large. When a is 3, the clearing point is extremely high, and the optical anisotropy is large.

As described above, a compound having objective physical properties can be obtained by suitably selecting a kind of the ring structure, the terminal group, the bonding group or the like. Accordingly, compound (1) is useful as a component of a liquid crystal composition used in a liquid crystal display device having a mode such as the PC mode, the TN mode, the STN mode, the ECB mode, the OCB mode, the IPS mode and the VA mode.

1-3. Preferred Compound

Specific preferred examples of compounds (1) include compounds (1-1) to (1-4). Further preferred examples include compounds (1-5) to (1-12). Most preferred examples include compounds (1-13) to (1-23)

(1-1)

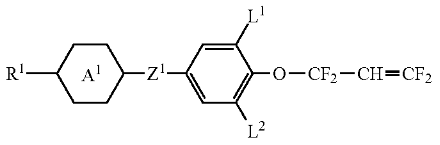

(1-2)

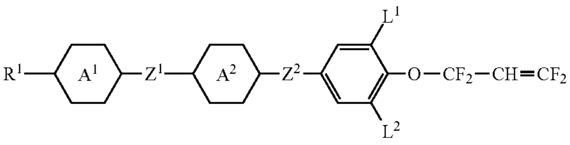

(1-3)

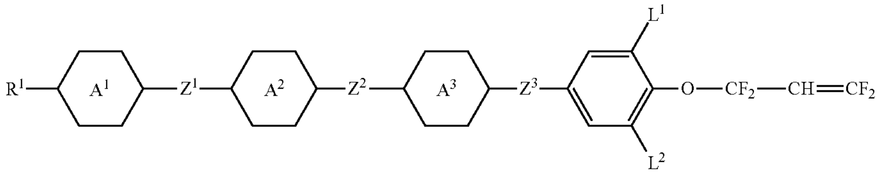

(1-4)

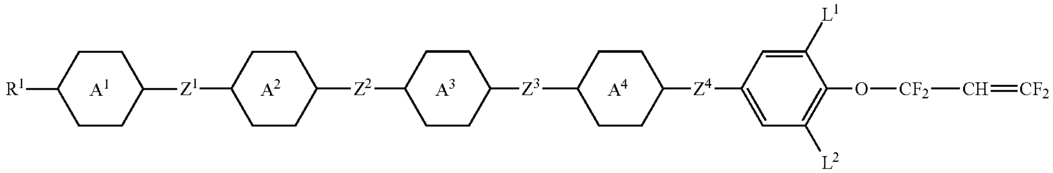

wherein, in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by halogen, tetrahydropyran-2,5-diyl, 1,3-dioxane-2,5-diyl or 2,6,7-trioxabicyclo[2.2.2]octane-1,4-diyl;

$Z^1$, $Z^2$, $Z^3$ and $Z^4$ are independently a single bond, $-CH_2CH_2-$, $-CH{=}CH-$, $-CF_2O-$ or $-COO-$;

$R^1$ is alkyl having 1 to 10 carbons or alkenyl having 2 to 10 carbons; and $L^1$ and $L^2$ are independently hydrogen or halogen.

A compound is further preferred, wherein in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by fluorine or chlorine, tetrahydropyran-2,5-diyl or 1,3-dioxane-2,5-diyl;

$Z^1$, $Z^2$, $Z^3$ and $Z^4$ are independently a single bond, $-CH_2CH_2-$, $-CH{=}CH-$ or $-CF_2O-$;

$R^1$ is alkyl having 1 to 10 carbons or alkenyl having 2 to 10 carbons; and $L^1$ and $L^2$ are independently hydrogen or fluorine.

(1-5)

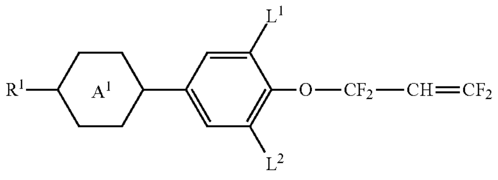

(1-6)

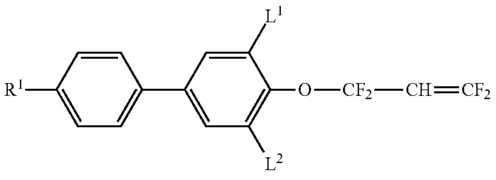

(1-7)

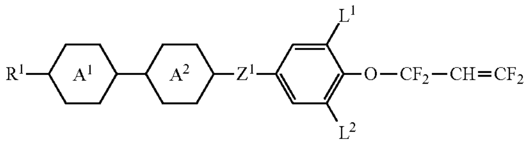

(1-8)

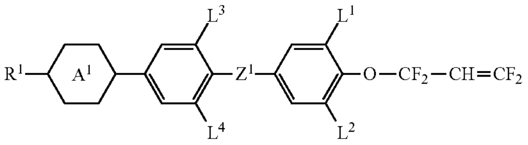

(1-9)

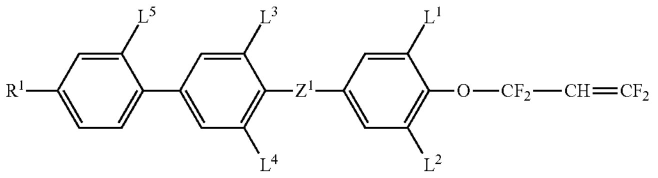

(1-10)

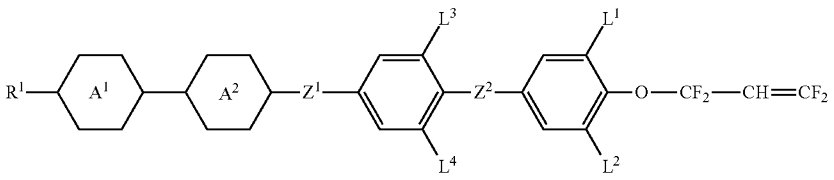

(1-11)

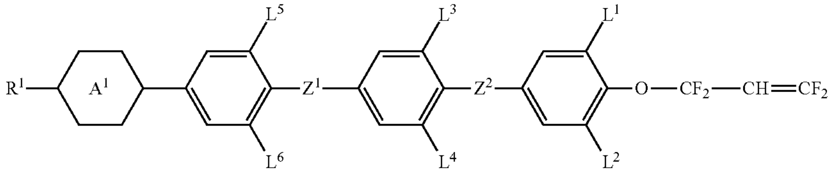

(1-12)

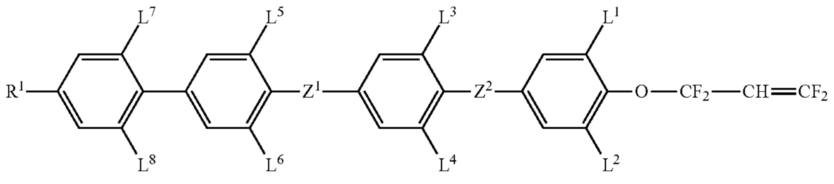

wherein, in formulas (1-5) to (1-12),
ring $A^1$ and ring $A^2$ are independently 1,4-cyclohexylene, tetrahydropyran-2,5-diyl or 1,3-dioxane-2,5-diyl;
$Z^1$ and $Z^2$ are independently a single bond or $-CF_2O-$;
$R^1$ is alkyl having 1 to 10 carbons or alkenyl having 2 to 10 carbons; and
$L^1$, $L^2$, $L^3$, $L^4$, $L^5$, $L^6$, $L^7$ and $L^8$ are independently hydrogen or fluorine.
(1-13)
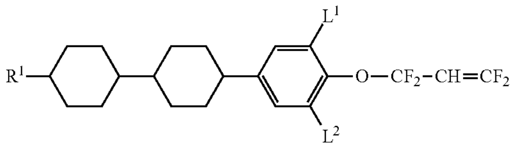
(1-14)
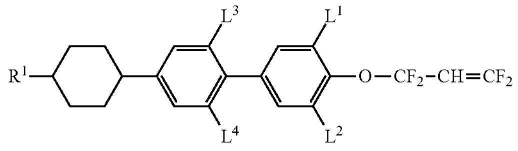
(1-15)
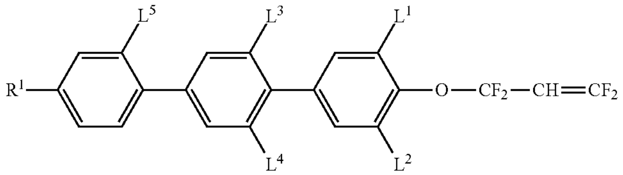
(1-16)
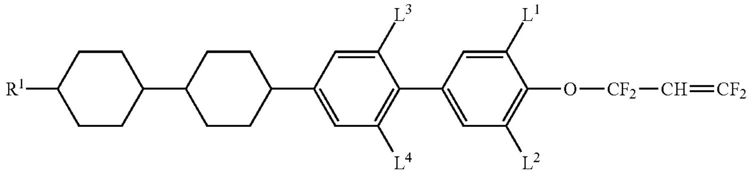
(1-17)
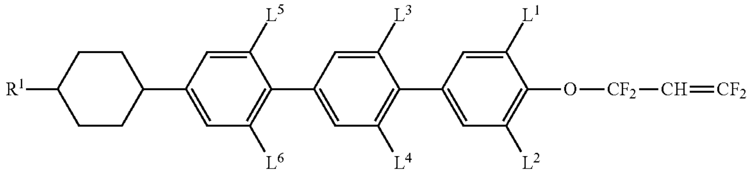
(1-18)
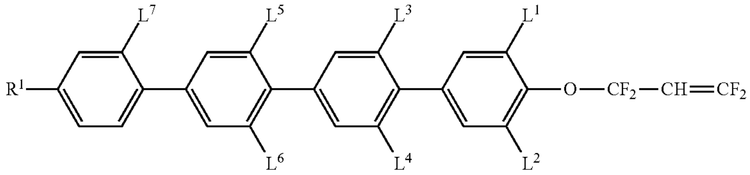
(1-19)
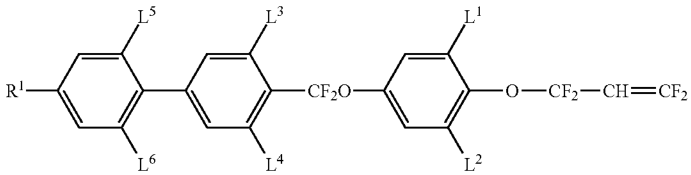
(1-20)
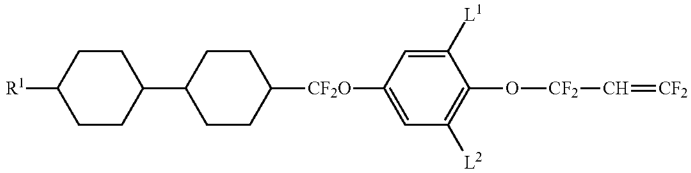
(1-21)
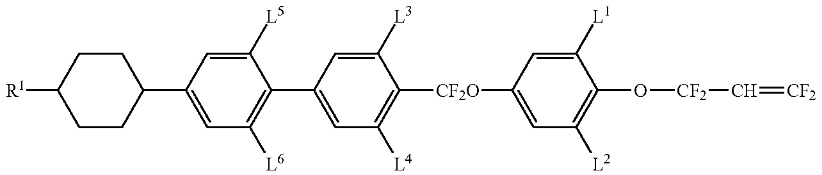

-continued (1-22)

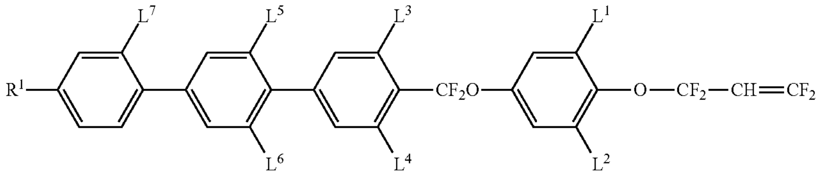

(1-23)

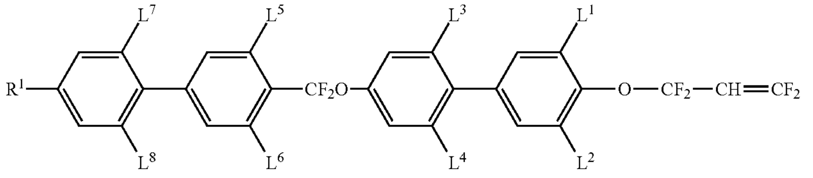

wherein, in formulas (1-13) to (1-23), $R^1$ is alkyl having 1 to 10 carbons or alkenyl having 2 to 10 carbons; and $L^1$, $L^2$, $L^3$, $L^4$, $L^5$, $L^6$, $L^7$ and $L^8$ are independently hydrogen or fluorine.

A liquid crystal compound of the invention has $R^1$, ring $A^1$, ring $A^2$, $Z^1$ and $Z^2$ described above, and has a 1,1,3,3-tetrafluoro-2-propenyloxy group, and thus is excellent in a good balance regarding a high stability to heat and light, a high clearing point, a low minimum temperature of a liquid crystal phase, a small viscosity, a suitable optical anisotropy, a large dielectric anisotropy, a suitable elastic constant, an excellent compatibility with other liquid crystal compounds or the like, and has an especially excellent compatibility with other liquid crystal compounds and a high stability to heat, light or the like, and also has a large dielectric anisotropy.

1-4. Synthesis of Compound (1)

A synthesis method of compound (1) will be described. Compound (1) can be prepared by suitably combining methods in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-4-1. Formation of a Bonding Group

An example of a method for forming a bonding group in compound (1) is as described in a scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1).

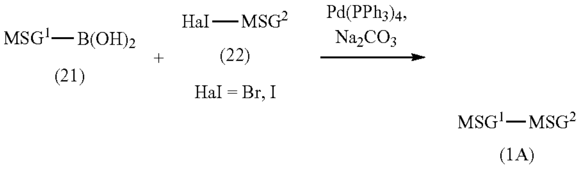

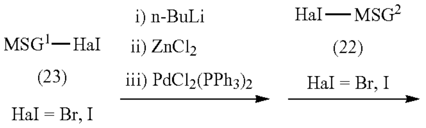

-continued $MSG^1$—$MSG^2$ (1A)

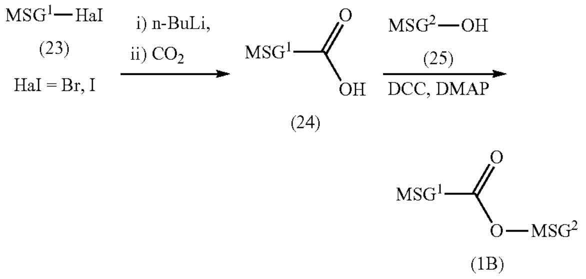

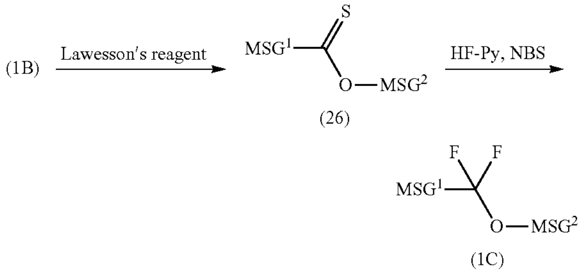

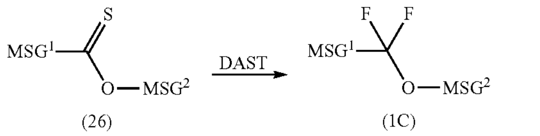

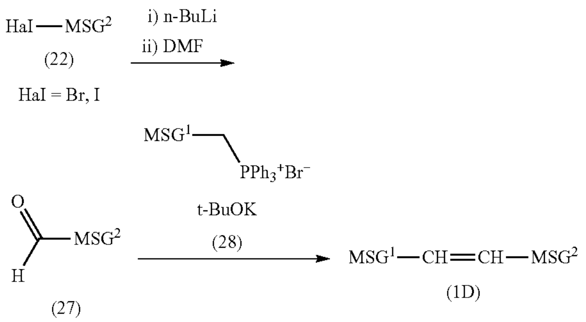

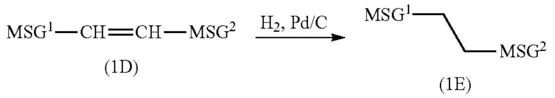

-continued

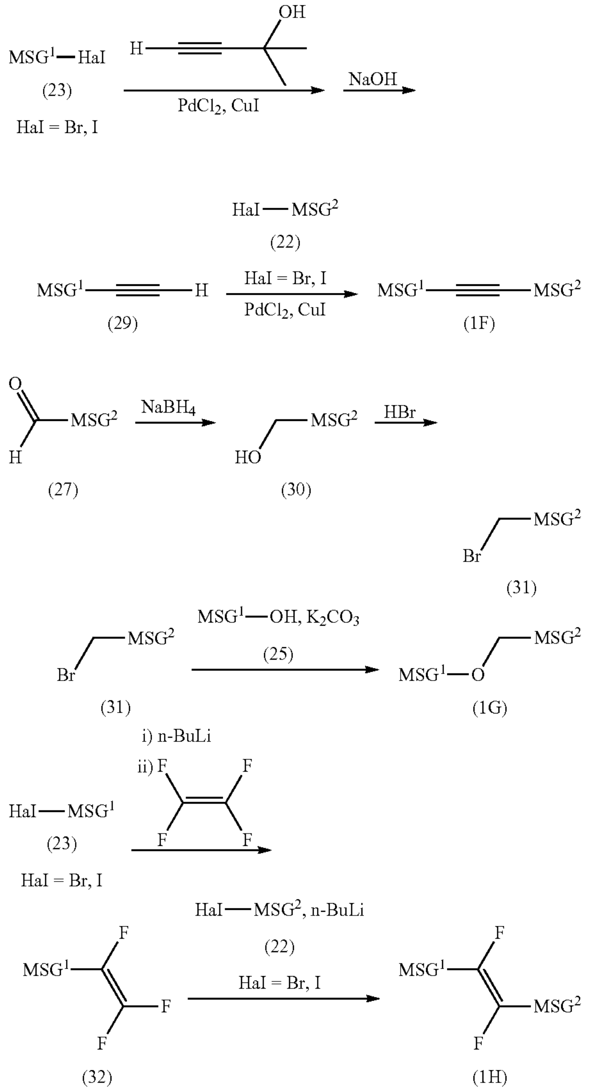

(23) (22) (29) (1F) (27) (30) (31) (25) (31) (1G) (23) (22) (32) (1H)

(I) Formation of a Single Bond

Compound (1A) is prepared by allowing arylboronic acid (21) to react with compound (22), in the presence of carbonate and a catalyst including tetrakis(triphenylphosphine)palladium. Compound (1A) is also prepared by allowing compound (23) to react with n-butyllithium and subsequently with zinc chloride, and further with compound (22) in the presence of a catalyst including dichlorobis(triphenylphosphine)palladium.

(II) Formation of —COO— and —OCO—

Carboxylic acid (24) is obtained by allowing compound (23) to react with n-butyllithium and subsequently with carbon dioxide. Compound (1B) having —COO— is prepared by dehydration of carboxylic acid (24) described above and phenol (25) derived from compound (21), in the presence of 1,3-dicyclohexylcarbodiimide (DCC) and 4-dimethylaminopyridine (DMAP). A compound having —OCO— is also prepared by the method.

(III) Formation of $—CF_2O—$ and $—OCF_2—$

Compound (26) is obtained by sulfurating compound (1B) with a Lawesson's reagent. Compound (1C) having $—CF_2O—$ is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino)sulfur trifluoride (DAST). Refer to W. H. Bunnelle et al., J. Org. Chem. 1990, 55, 768. A compound having $—OCF_2—$ is also prepared by the method.

(IV) Formation of —CH═CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium t-butoxide to react with aldehyde (27). A cis isomer may be generated depending on reaction conditions, and therefore the cis isomer is isomerized into a trans isomer according to a publicly known method when necessary.

(V) Formation of $—CH_2CH_2—$

Compound (1E) is prepared by hydrogenating compound (1D) in the presence of a catalyst including palladium on carbon.

(VI) Formation of —C≡C—

Compound (29) is obtained by allowing compound (23) to react with 2-methyl-3-butyn-2-ol in the presence of a catalyst including dichloropalladium and copper iodide, and then performing deprotection under basic conditions. Compound (1F) is prepared by allowing compound (29) to react with compound (22) in the presence of a catalyst including dichlorobis(triphenylphosphine) palladium and copper halide.

(VII) Formation of $—CH_2O—$ and $—OCH_2—$

Compound (30) is obtained by reducing compound (27) with sodium borohydride. Compound (31) is obtained by brominating the obtained compound with hydrobromic acid. Compound (1G) is prepared by allowing compound (25) to react with compound (31) in the presence of potassium carbonate. A compound having $—OCH_2—$ is also prepared by the method.

(VIII) Formation of —CF═CF—

Compound (32) is obtained by treating compound (23) with n-butyllithium, and then allowing the treated compound to react with tetrafluoroethylene. Compound (1H) is prepared by treating compound (32) with n-butyllithium, and then allowing the treated compound to react with compound (22).

Phenol (33) is prepared by a combination of processes described above.

1-4-2. Formation of Ring $A^1$ and Ring $A^2$

With regard to a ring such as 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl, pyrimidine-2,5-diyl, pyridine-2, 5-diyl and 2,6,7-trioxabicyclo[2.2.2]octane-1, 4-diyl, a starting material is commercially available or a synthetic process is well known.

1-4-3. Synthesis Examples

An example of a method for preparing compound (1) is as described below.

Synthesis Method 1

Compound (1) is prepared by allowing phenol (33) prepared according to a publicly known method to react with 1,3-difluoro-1,1,3,3-tetrafluoropropane in acetonitrile in the presence of potassium carbonate at 65° C. for 4 hours.

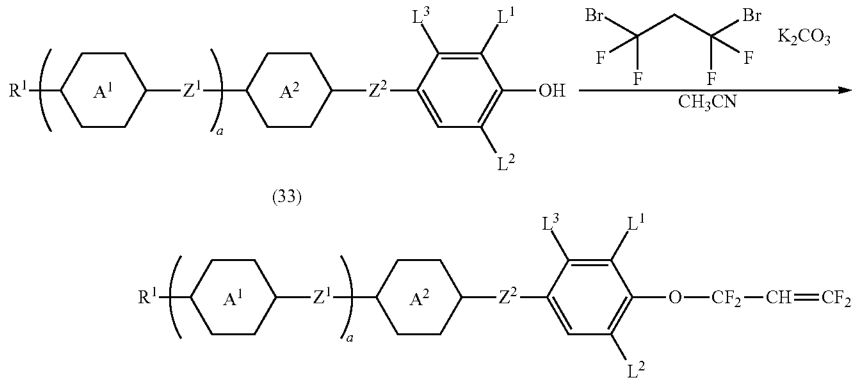

(33)

(1)

Synthesis Method 2

Compound (1) is prepared by stirring phenol (33) prepared according to a publicly known method and 1,1,3,3-tetrafluoropropene in THF in the presence of potassium carbonate at room temperature for 12 hours. In addition, 1,1,3,3-tetrafluoropropene used for the reaction is obtained by allowing 1,1,3,3,3-pentafluoropropene to react with t-butyllithium in diethyl ether.

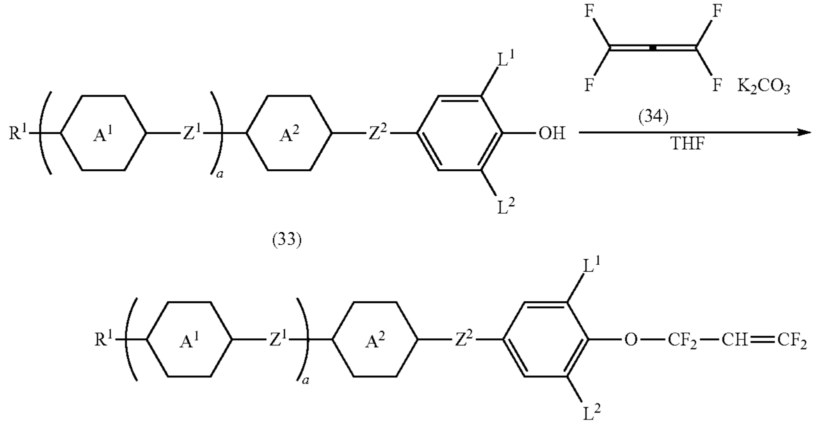

(33)

(1)

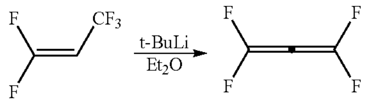

(35) (34)

In the compounds, definitions of $R^1$, ring $A^1$, ring $A^2$, $Z^1$, $Z^2$, $L^1$, $L^2$, $L^3$ and a are identical to formula (1) described in item 1.

2. Composition (1)

Liquid crystal composition (1) of the invention will be described. Composition (1) described above contains at least one compound (1) as component A. Composition (1) may contain two or more compounds (1). A component in the liquid crystal compound may be only compound (1). In order to develop excellent physical properties, composition (1) preferably contains at least one of compounds (1) in the range of 1 to 99% by weight. In a composition having a positive dielectric anisotropy, a preferred content of compound (1) is in the range of 5 to 60% by weight. In a composition having a negative dielectric anisotropy, a preferred content of compound (1) is 30% by weight or less. Composition (1) may also contain compound (1) and various liquid crystal compounds that are not described herein.

A preferred composition contains a compound selected from components B, C, D and E shown below. When composition (1) is prepared, components can also be selected, for example, by taking into account a dielectric anisotropy of compound (1). When a composition having the positive dielectric anisotropy is prepared for a mode such as the TFT mode, the IPS mode and the FFS mode, main components include components A, B and E. When a composition having the positive dielectric anisotropy is prepared for a mode such as the STN mode and the TN mode, main components include components A, C and E. When a composition having the negative dielectric anisotropy is prepared for a mode such as the VA mode and the PSA mode, main components include components D and E, and component A is added for the purpose of adjusting a voltage-transmittance curve of a device. A composition in which the components are suitably selected has a high maximum temperature, a low minimum temperature, a small viscosity, a suitable optical anisotropy, a large dielectric anisotropy and a suitable elastic constant.

Component B includes compounds (2) to (4) described in item 9. Component C includes compound (5) described in item 10. Component D includes compounds (6) to (12) described in item 11. Component E includes compounds (13) to (15) described in item 12. The components will be described in the order.

Component B is a compound having a halogen-containing group or a fluorine-containing group at a right terminal. Specific preferred examples of component B include compounds (2-1) to (2-16), compounds (3-1) to (3-113) and compounds (4-1) to (4-57). In the compounds, definitions of $R^{11}$ and $X^{11}$ are identical to compounds (2) to (4) described in item 9.

(2-1)

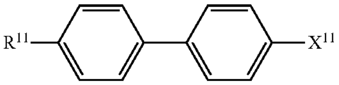

(2-2)

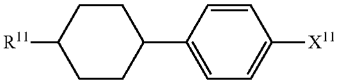

(2-3)

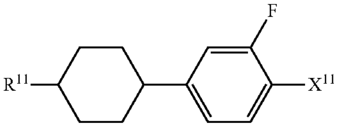

(2-4)

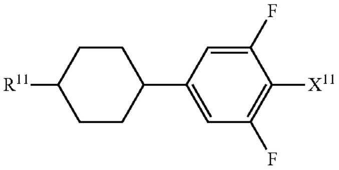

(2-5)

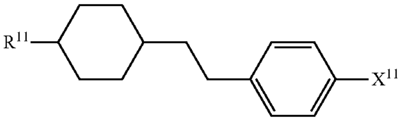

(2-6)

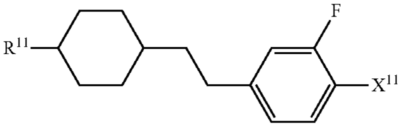

(2-7)

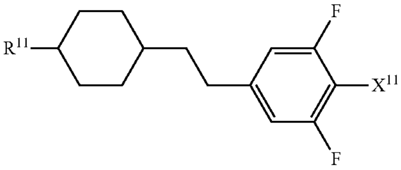

(2-8)

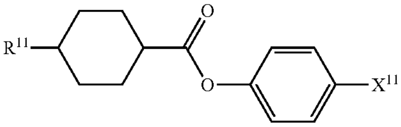

(2-9)

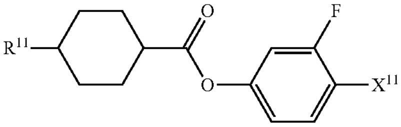

-continued (2-10)

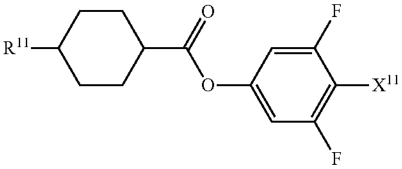

(2-11)

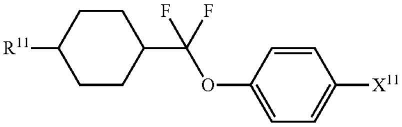

(2-12)

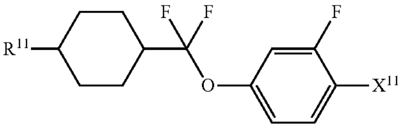

(2-13)

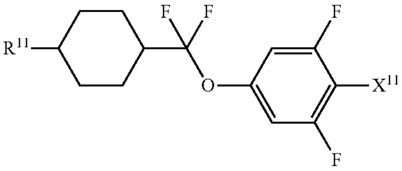

(2-14)

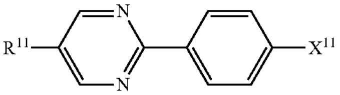

(2-15)

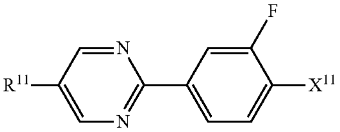

(2-16)

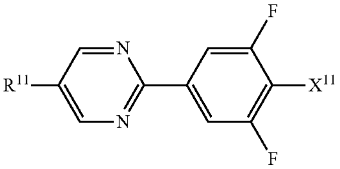

(3-1)

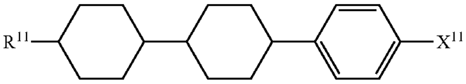

(3-2)

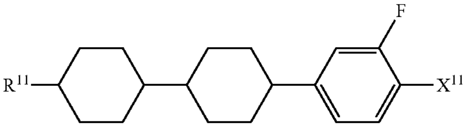

(3-3)

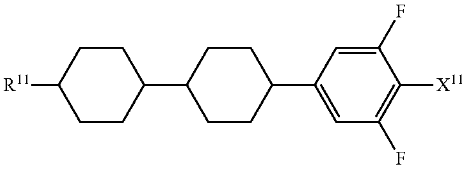

-continued
(3-4)
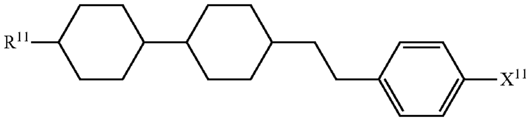
(3-5)
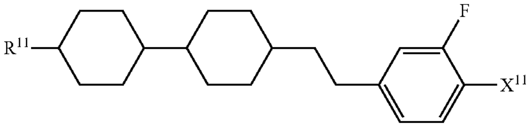
(3-6)
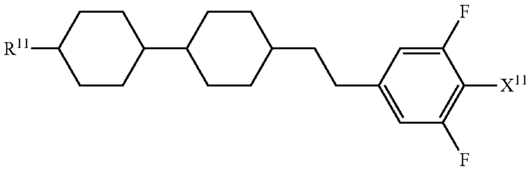
(3-7)
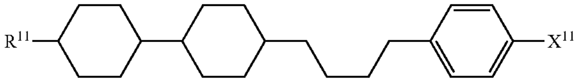
(3-8)
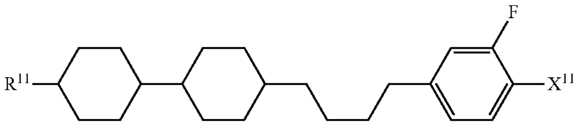
(3-9)
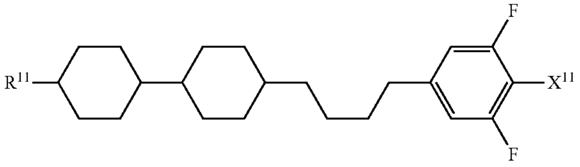
(3-10)
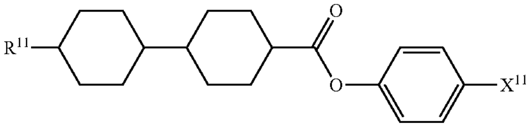
(3-11)
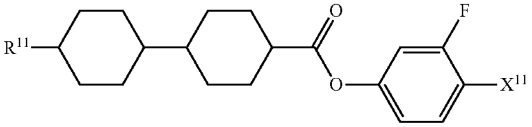
(3-12)
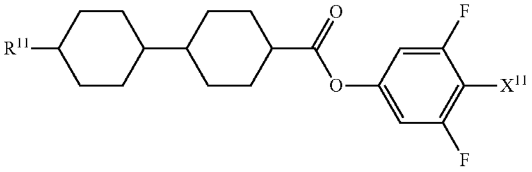
-continued
(3-13)
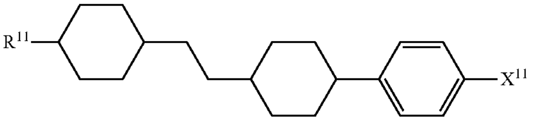
(3-14)
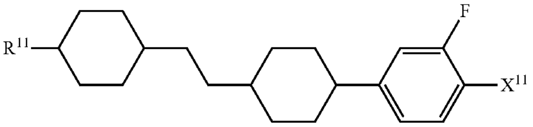
(3-15)
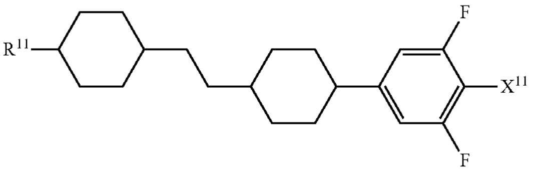
(3-16)
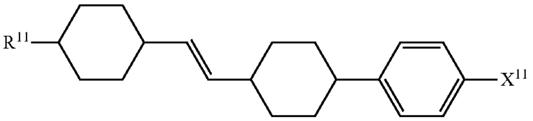
(3-17)
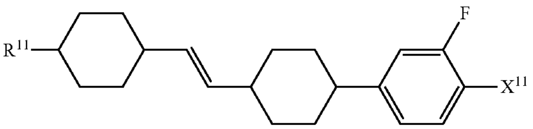
(3-18)
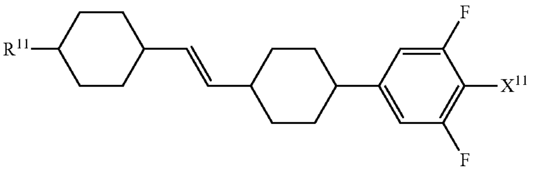
(3-19)
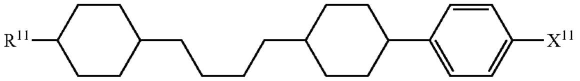
(3-20)
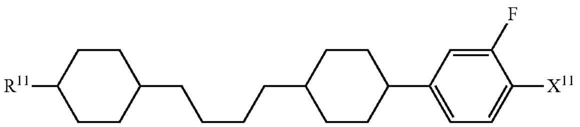
(3-21)
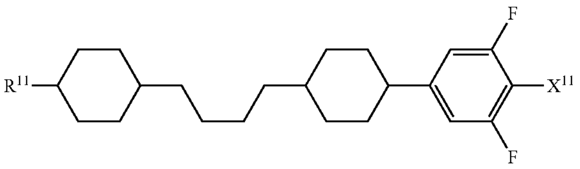
(3-22)
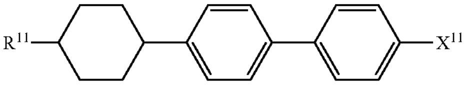

-continued
(3-23)
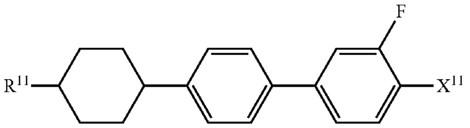
(3-24)
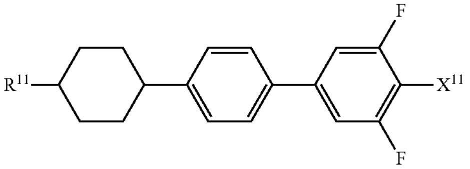
(3-25)
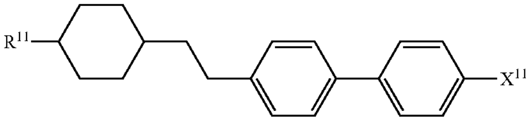
(3-26)
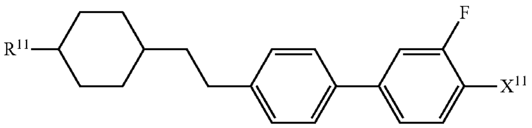
(3-27)
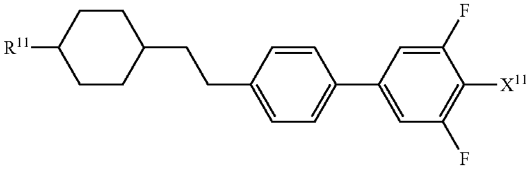
(3-28)
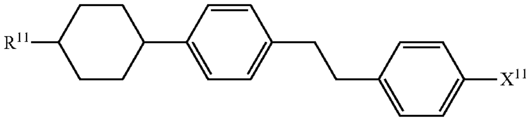
(3-29)
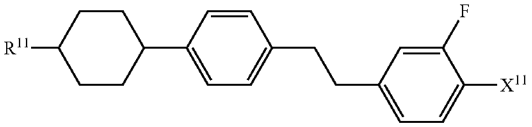
(3-30)
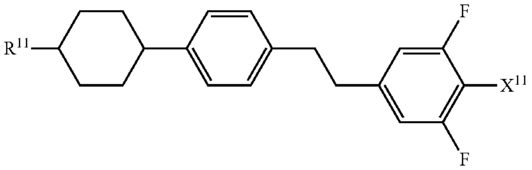
(3-31)
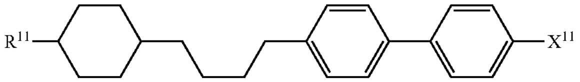
(3-32)
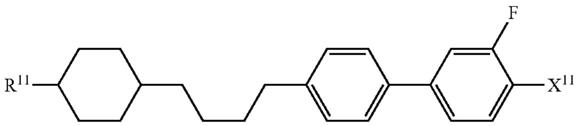
-continued
(3-33)
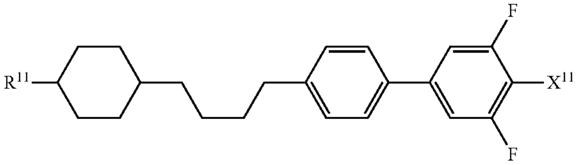
(3-34)
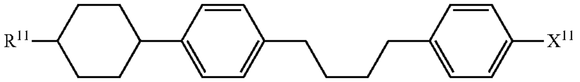
(3-35)
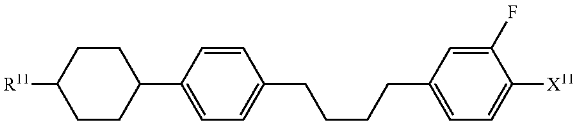
(3-36)
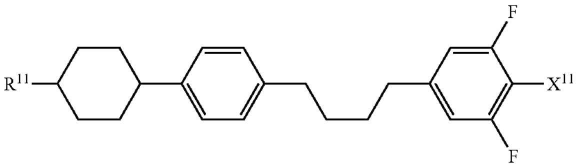
(3-37)
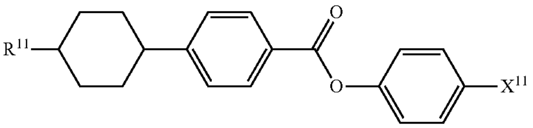
(3-38)
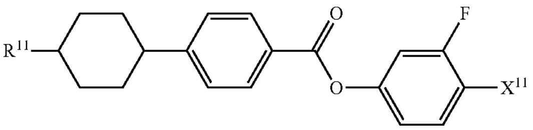
(3-39)
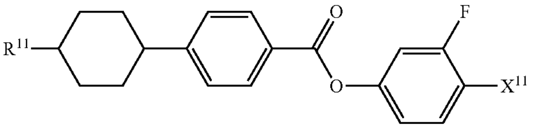
(3-40)
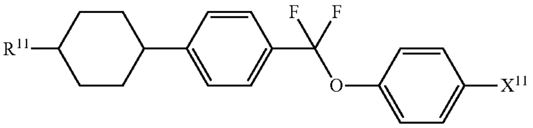
(3-41)
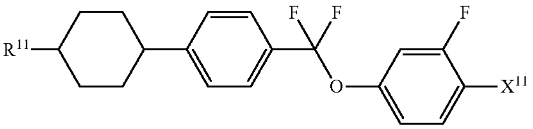

-continued
(3-42)
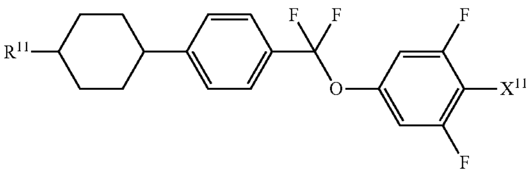
(3-43)
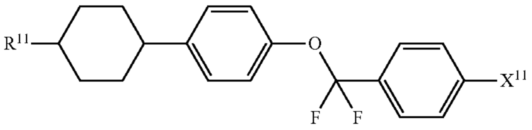
(3-44)
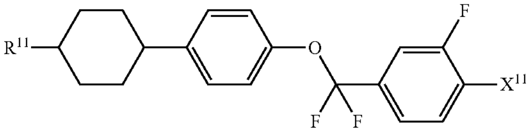
(3-45)
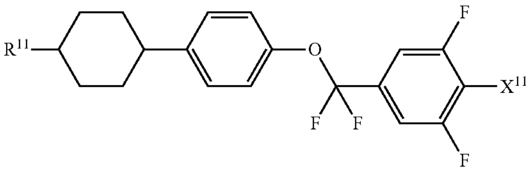
(3-46)
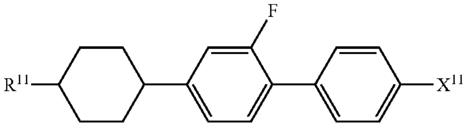
(3-47)
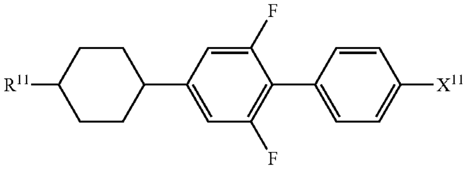
(3-48)
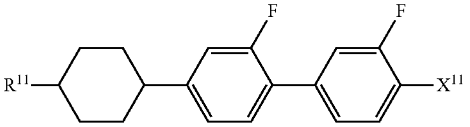
(3-49)
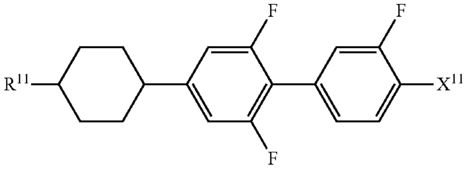
(3-50)
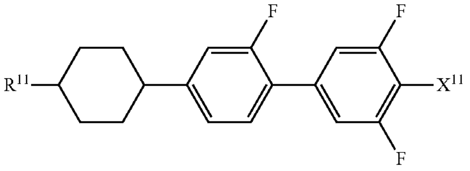
-continued
(3-51)
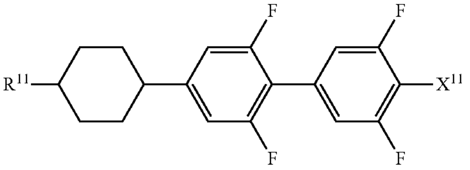
(3-52)
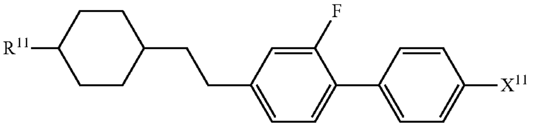
(3-53)
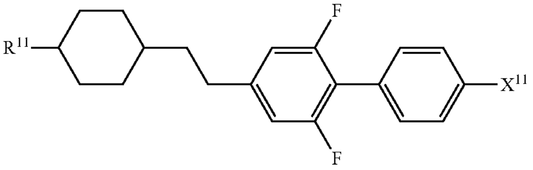
(3-54)
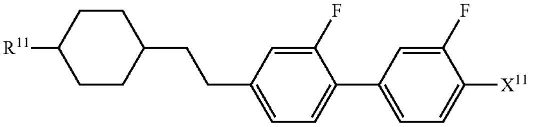
(3-55)
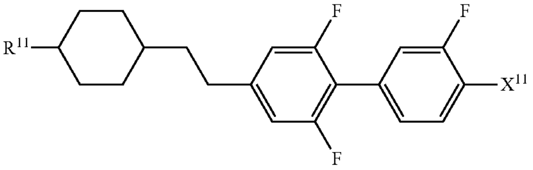
(3-56)
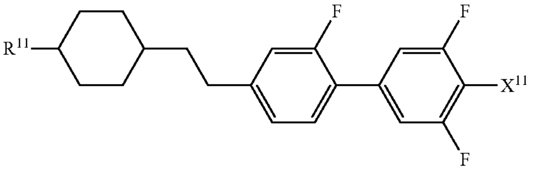
(3-57)
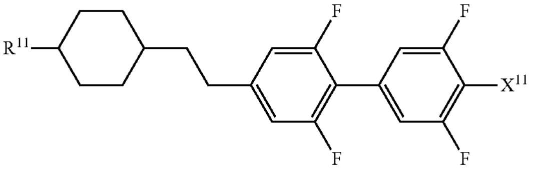
(3-58)
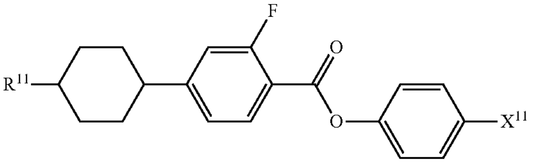

-continued
(3-59)
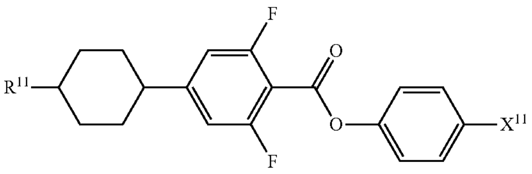
(3-60)
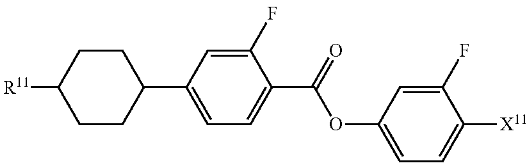
(3-61)
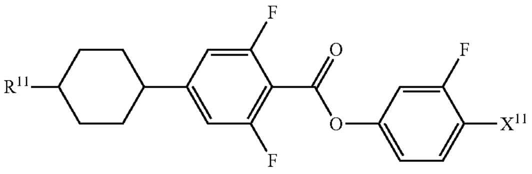
(3-62)
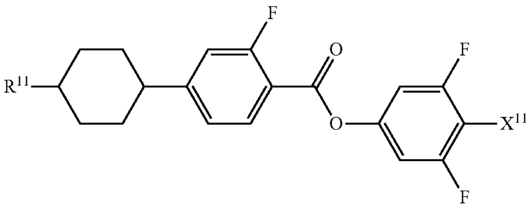
(3-63)
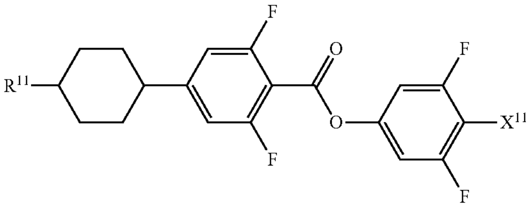
(3-64)
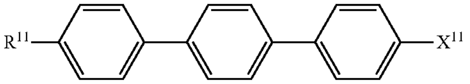
(3-65)
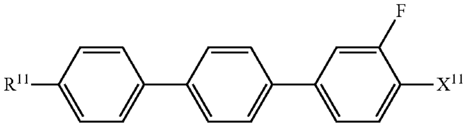
(3-66)
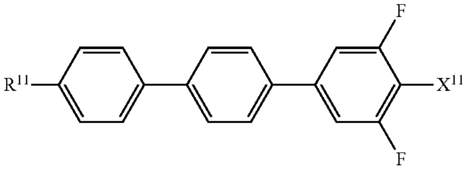
(3-67)
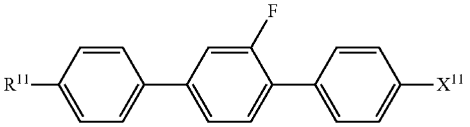
-continued
(3-68)
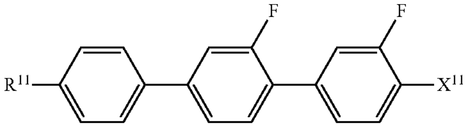
(3-69)
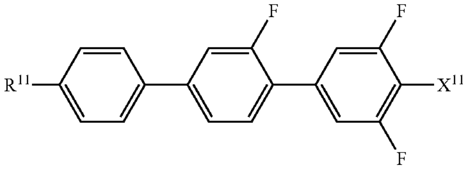
(3-70)
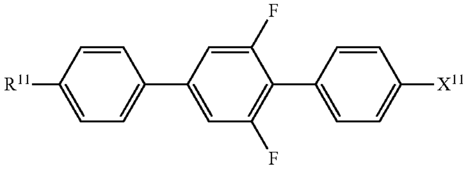
(3-71)
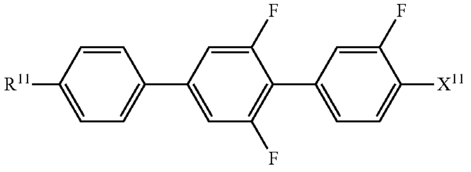
(3-72)
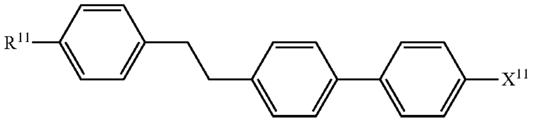
(3-73)
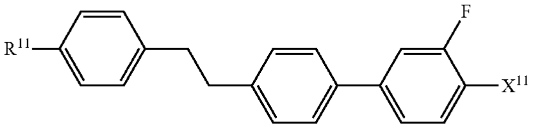
(3-74)
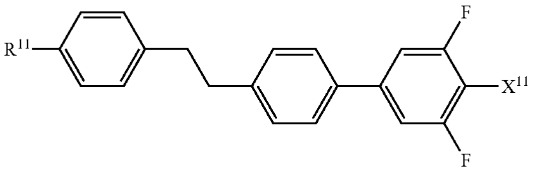
(3-75)
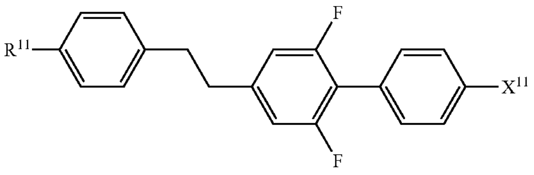
(3-76)
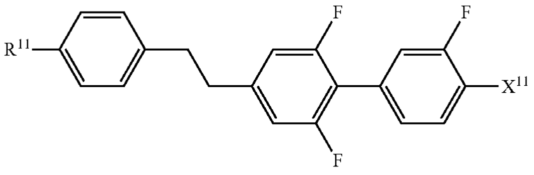

-continued
(3-77)
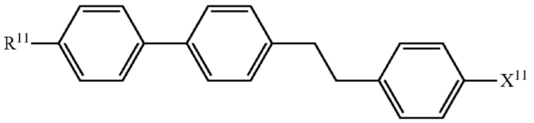
(3-78)
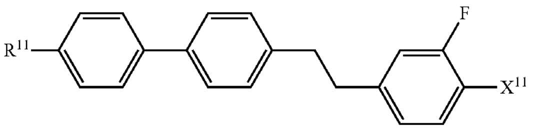
(3-79)
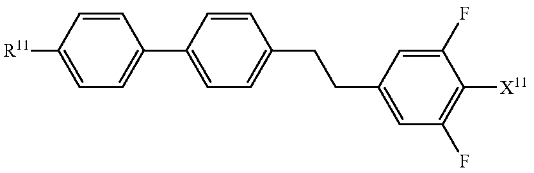
(3-80)
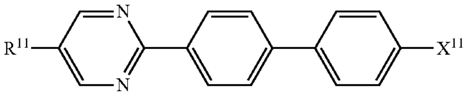
(3-81)
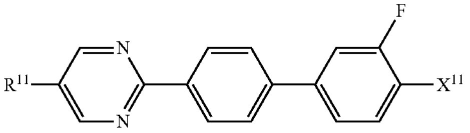
(3-82)
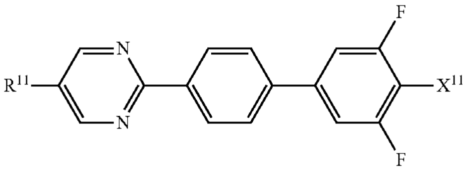
(3-83)
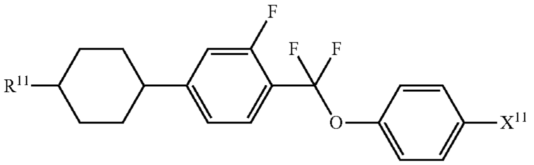
(3-84)
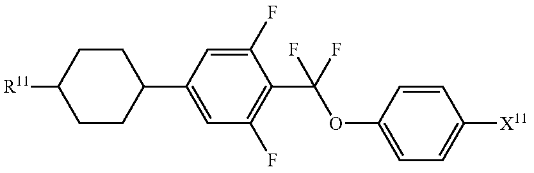
(3-85)
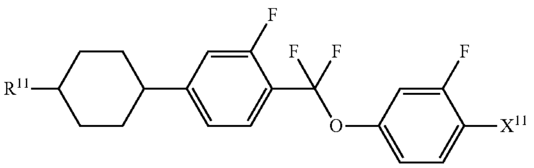
-continued
(3-86)
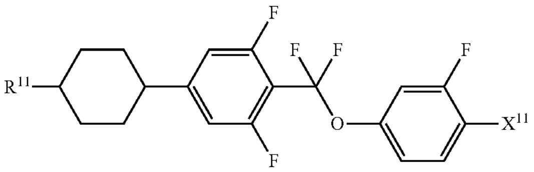
(3-87)
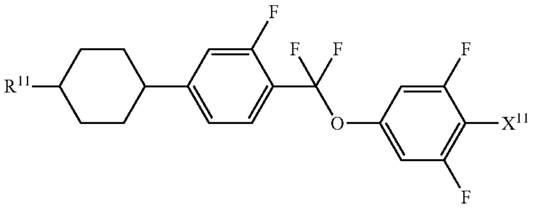
(3-88)
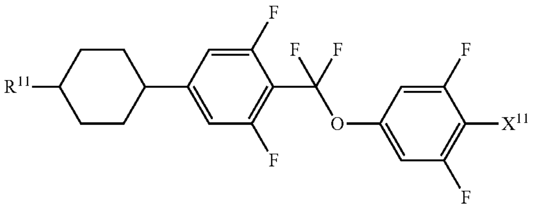
(3-89)
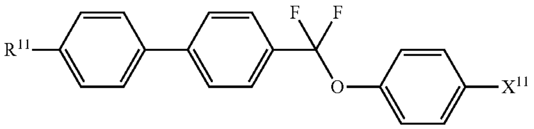
(3-90)
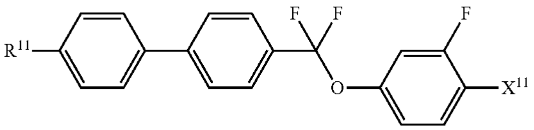
(3-91)
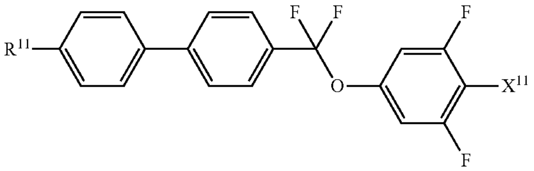
(3-92)
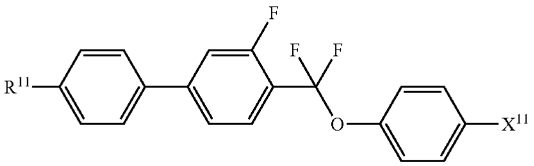
(3-93)
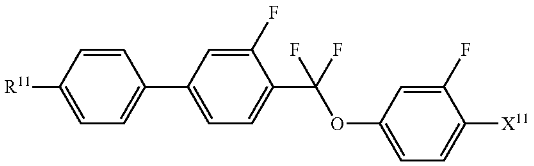

-continued
(3-94)
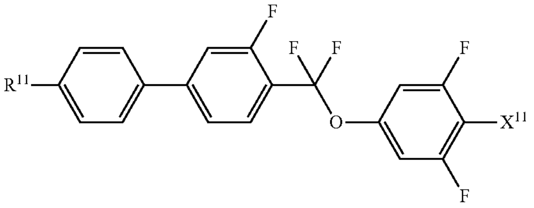
(3-95)
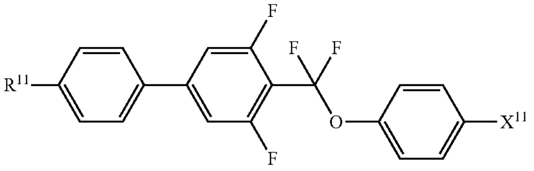
(3-96)
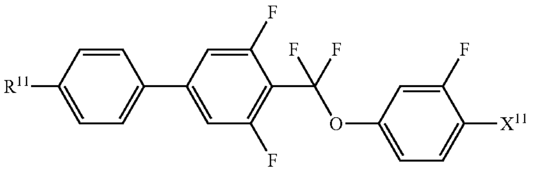
(3-97)
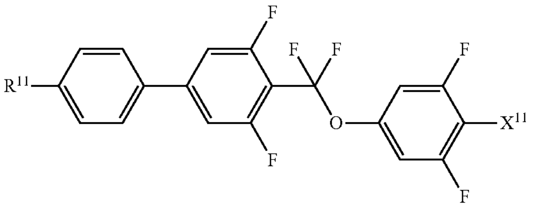
(3-98)
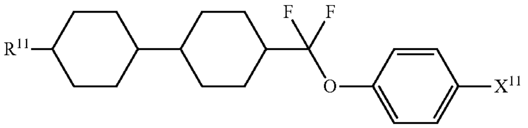
(3-99)
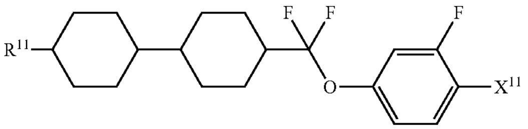
(3-100)
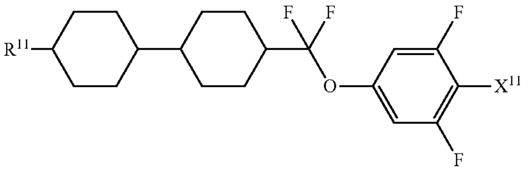
(3-101)
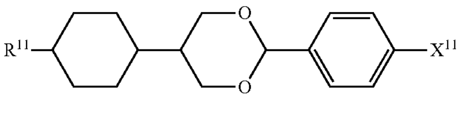
-continued
(3-102)
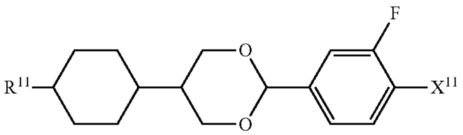
(3-103)
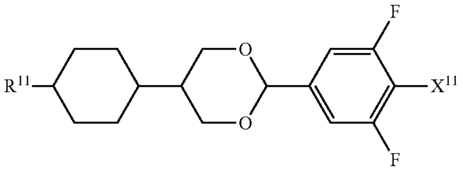
(3-104)
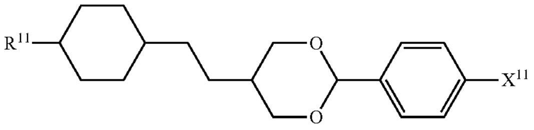
(3-105)
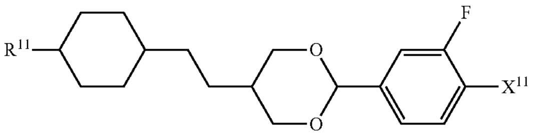
(3-106)
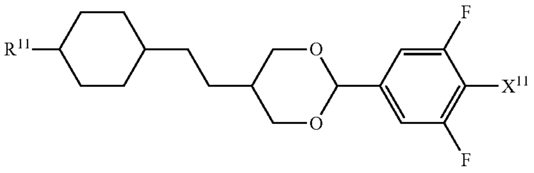
(3-107)
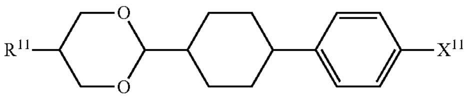
(3-108)
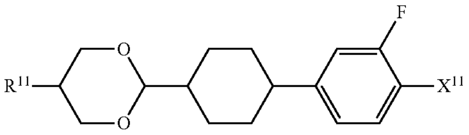
(3-109)
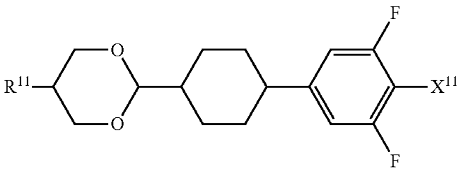
(3-110)
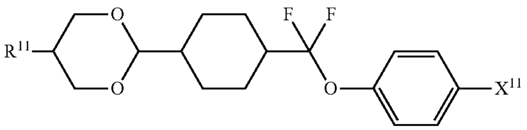

-continued
(3-111)
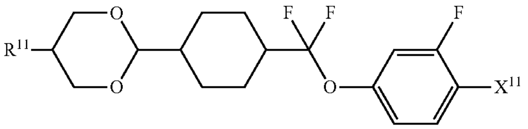
(3-112)
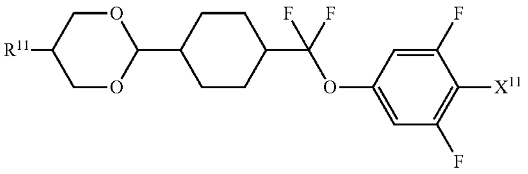
(3-113)
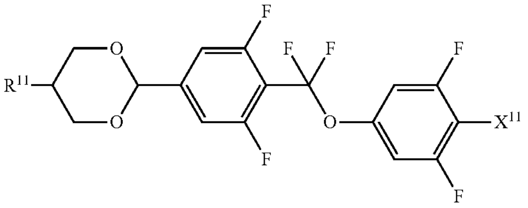
(4-1)
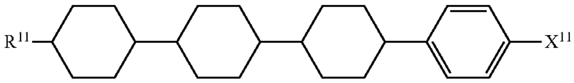
(4-2)
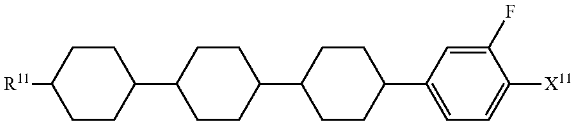
(4-3)
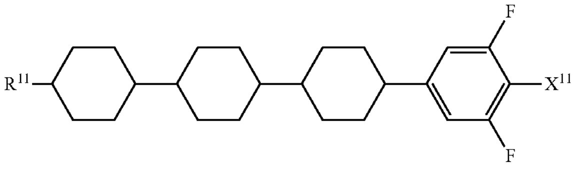
(4-4)
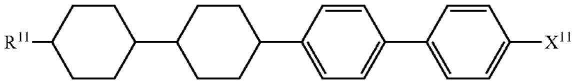
(4-5)
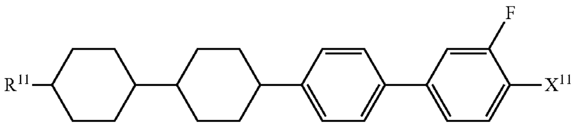
(4-6)
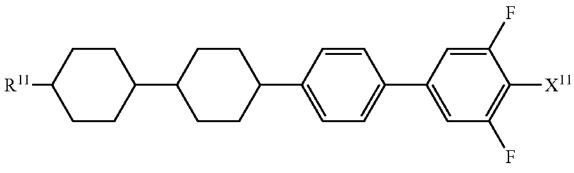
-continued
(4-7)
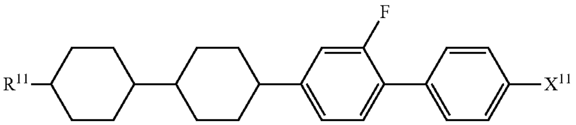
(4-8)
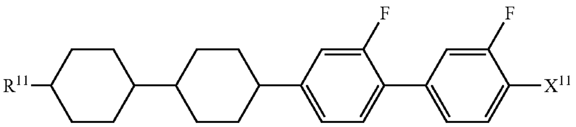
(4-9)
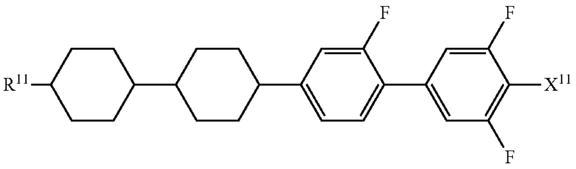
(4-10)
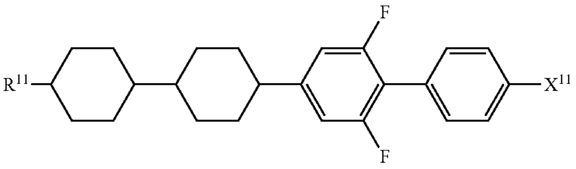
(4-11)
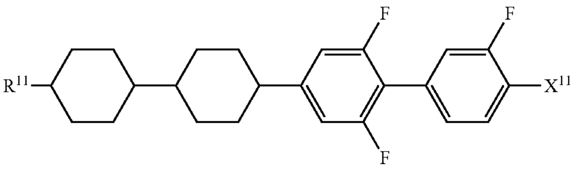
(4-12)
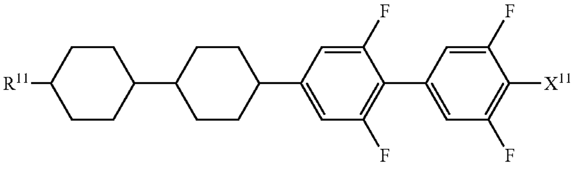
(4-13)
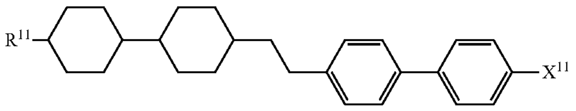
(4-14)
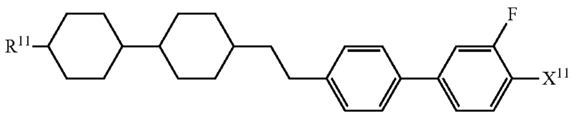
(4-15)
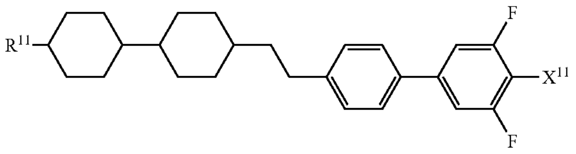

-continued
(4-16)
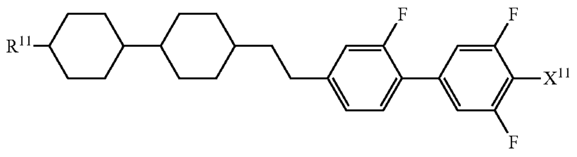
(4-17)
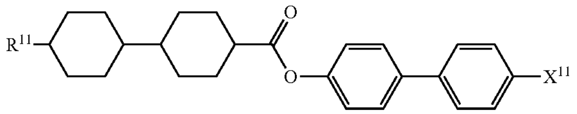
(4-18)
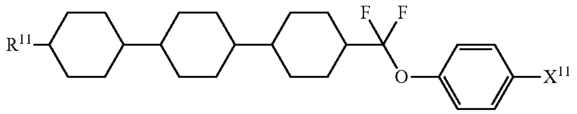
(4-19)
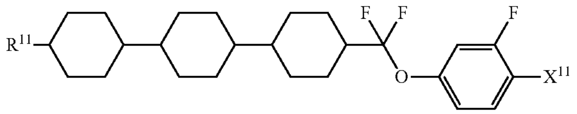
(4-20)
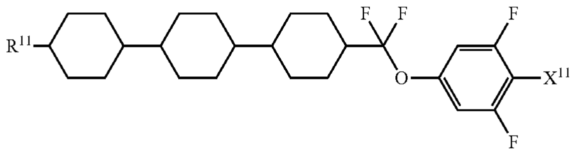
(4-21)
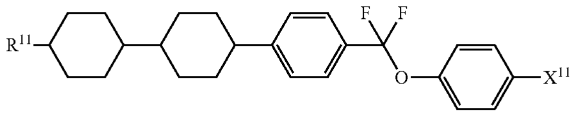
(4-22)
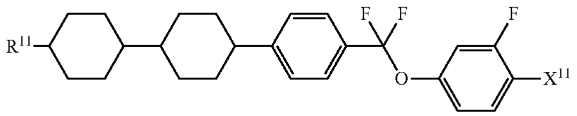
(4-23)
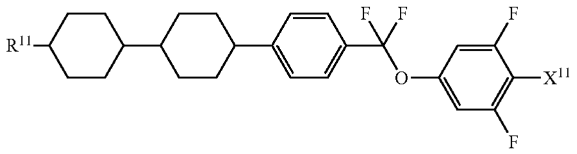
(4-24)
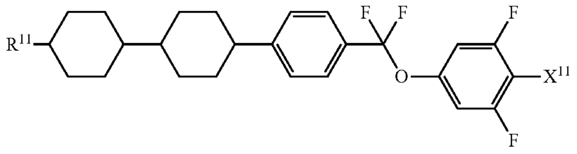
(4-25)
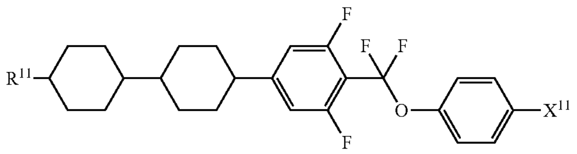
-continued
(4-26)
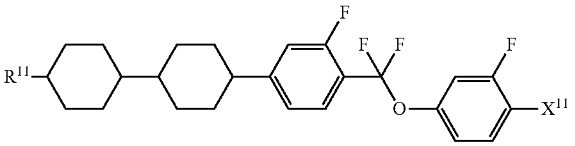
(4-27)
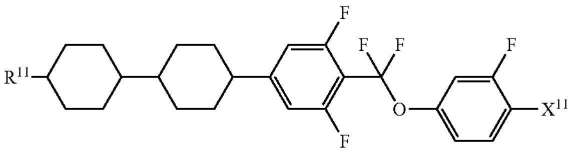
(4-28)
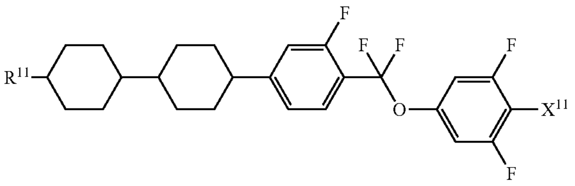
(4-29)
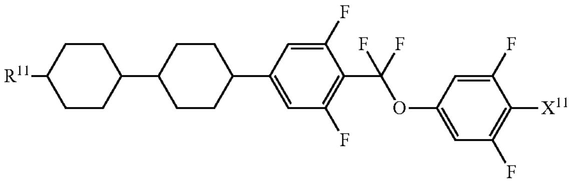
(4-30)
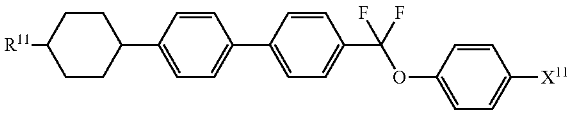
(4-31)
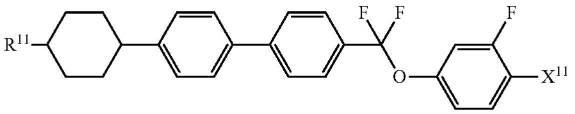
(4-32)
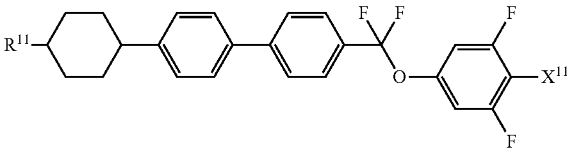
(4-33)
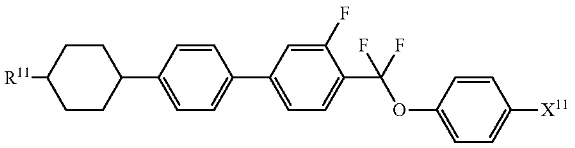
(4-34)
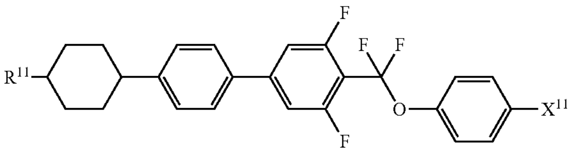

-continued
(4-35)
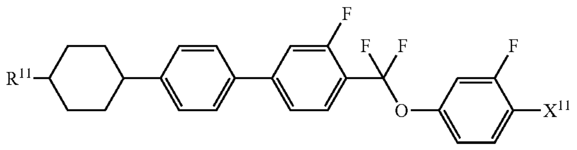
(4-36)
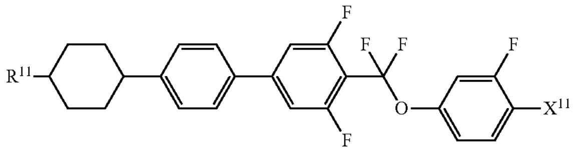
(4-37)
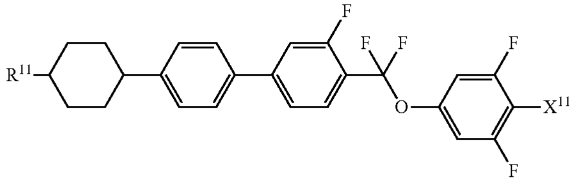
(4-38)
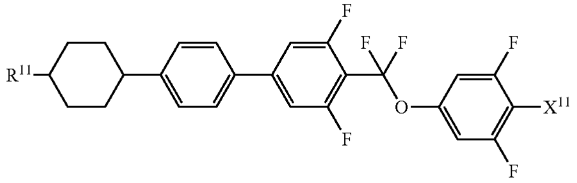
(4-39)
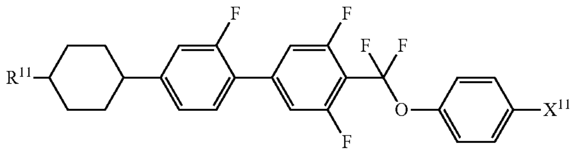
(4-40)
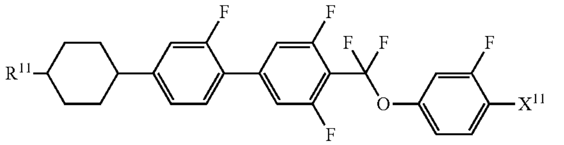
(4-41)
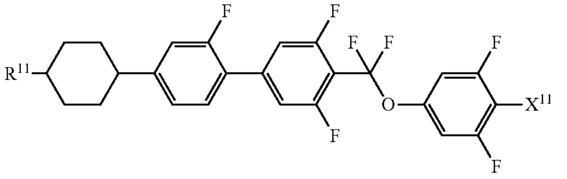
(4-42)
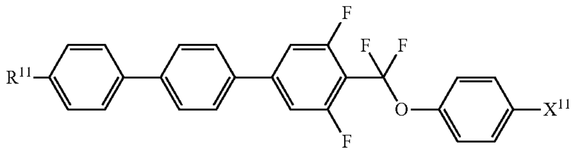
-continued
(4-43)
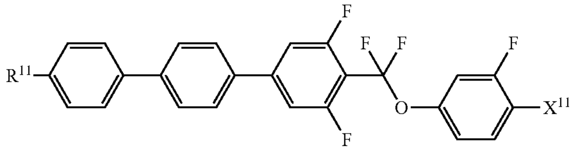
(4-44)
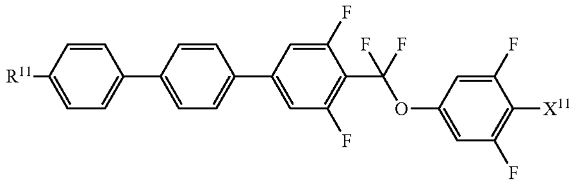
(4-45)
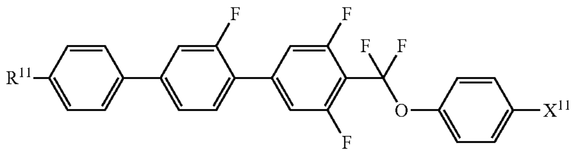
(4-46)
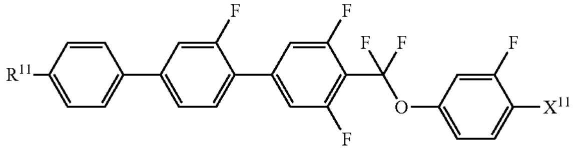
(4-47)
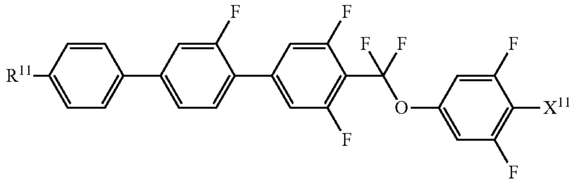
(4-48)
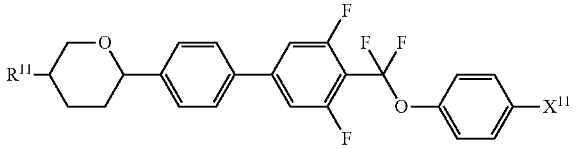
(4-49)
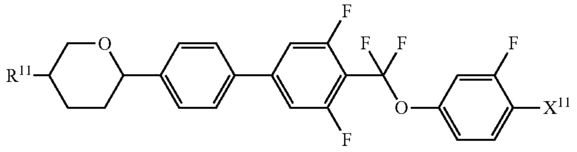
(4-50)
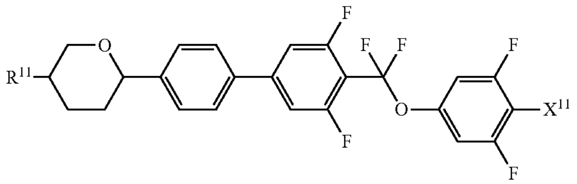

-continued (4-51)

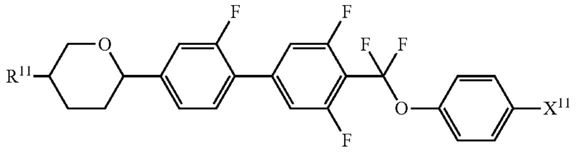

(4-52)

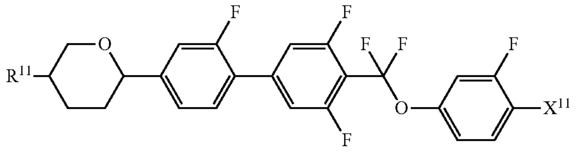

(4-53)

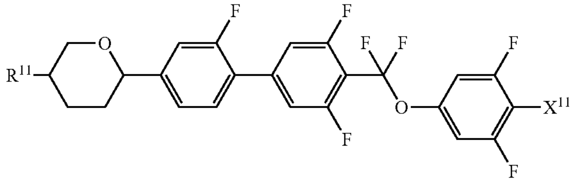

(4-54)

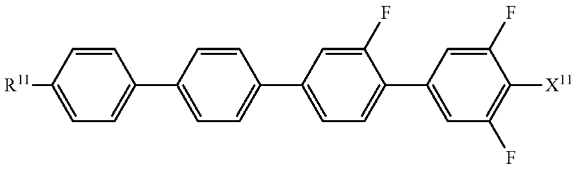

(4-55)

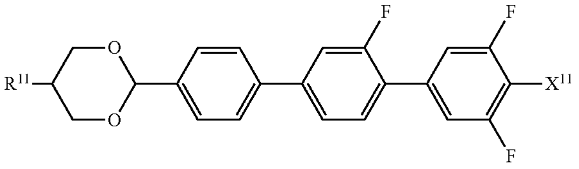

(4-56)

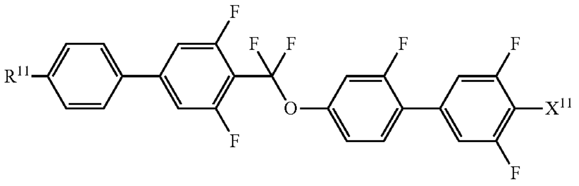

(4-57)

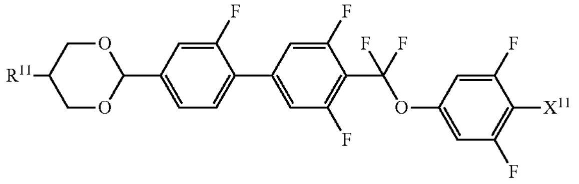

Component B has a positive dielectric anisotropy and a superb stability to heat, light or the like, and therefore is used for preparing a composition for the mode such as the TFT mode, the IPS mode and the FFS mode. A content of component B is suitably in the range of 1 to 99% by weight, preferably in the range of 10 to 97% by weight, and further preferably in the range of 40 to 95% by weight, based on the weight of the composition. Further addition of compounds (13) to (15) (component E) allows adjustment of viscosity of the composition.

Component C is compound (5) in which a right-terminal group is —C≡N or —C≡C—C≡N. Specific preferred examples of component C include compounds (5-1) to (5-64). In the compounds (component C), definitions of $R^{12}$ and $X^{12}$ are identical to compound (5) described in item 10.

(5-1)

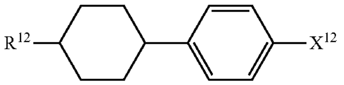

(5-2)

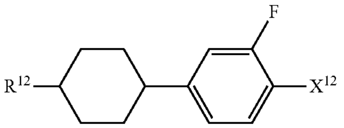

(5-3)

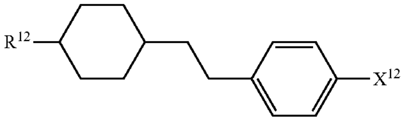

(5-4)

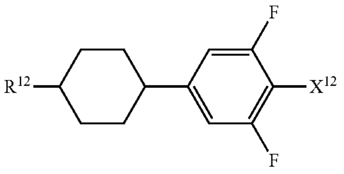

(5-5)

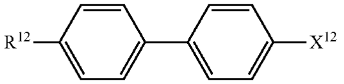

(5-6)

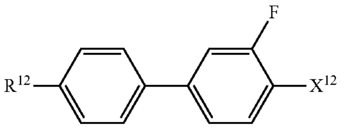

(5-7)

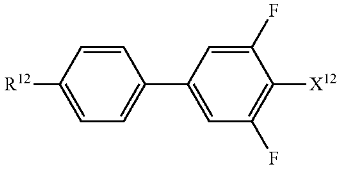

(5-8)

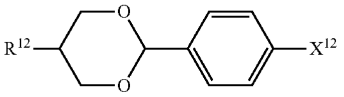

(5-9)

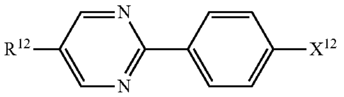

(5-10)

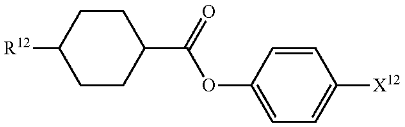

(5-11)

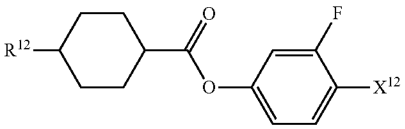

-continued
(5-12)
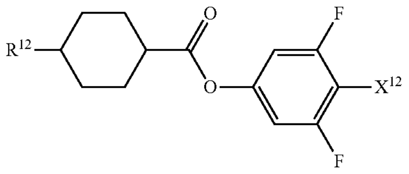
(5-13)
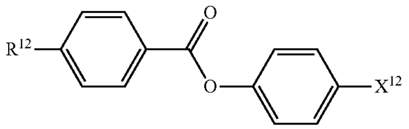
(5-14)
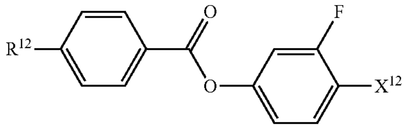
(5-15)
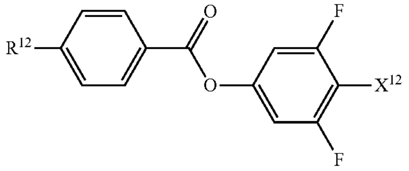
(5-16)
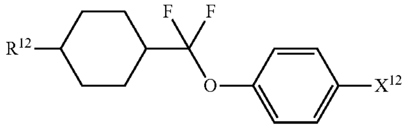
(5-17)
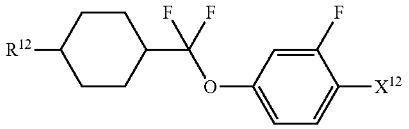
(5-18)
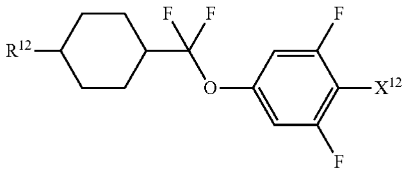
(5-19)
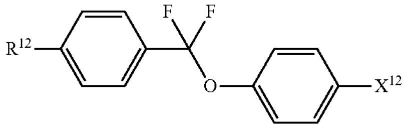
(5-20)
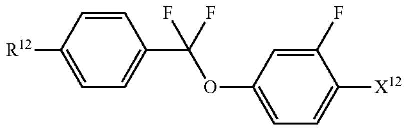
(5-21)
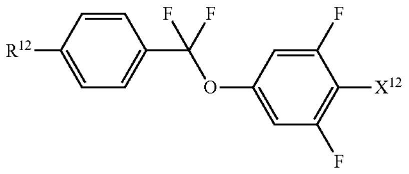
-continued
(5-22)
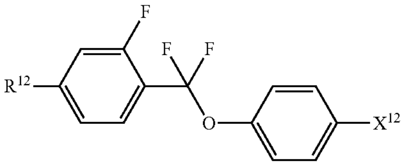
(5-23)
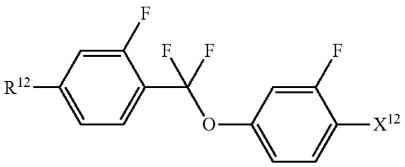
(5-24)
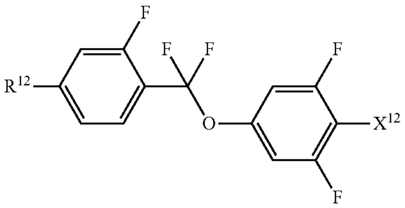
(5-25)
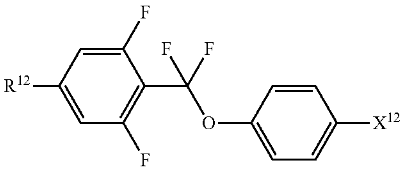
(5-26)
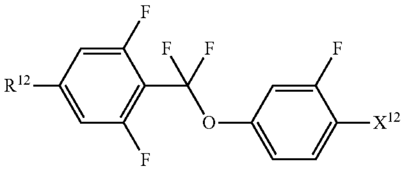
(5-27)
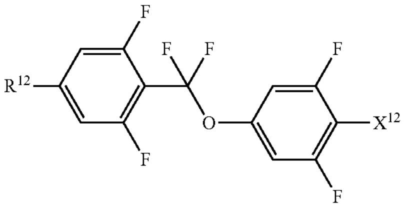
(5-28)
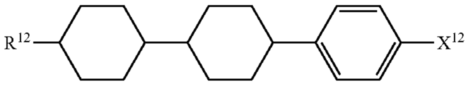
(5-29)
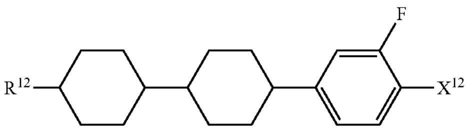
(5-30)
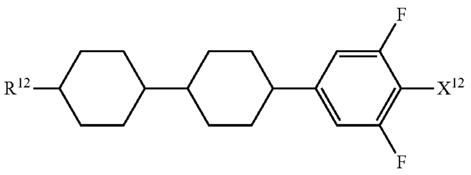

-continued
(5-31)
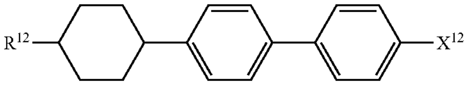
(5-32)
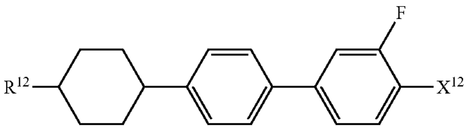
(5-33)
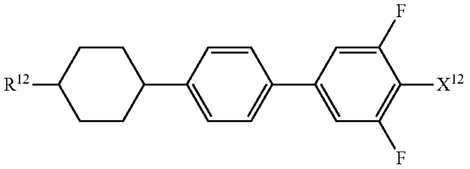
(5-34)
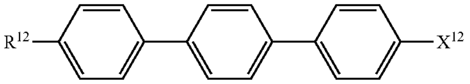
(5-35)
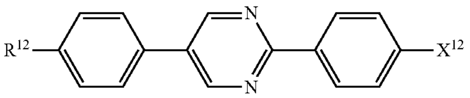
(5-36)
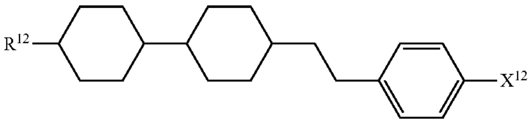
(5-37)
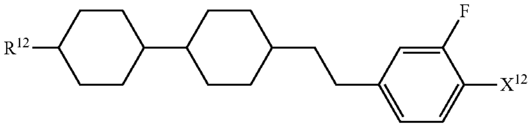
(5-38)
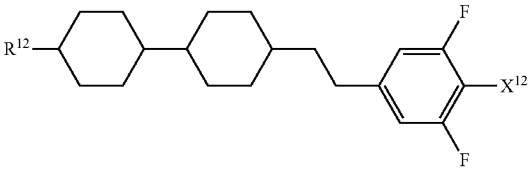
(5-39)
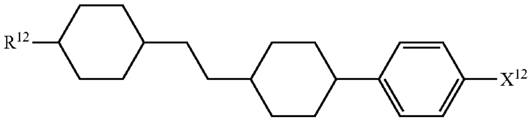
(5-40)
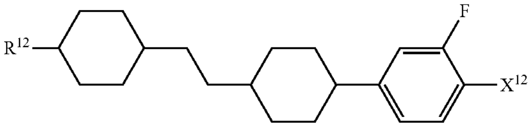
-continued
(5-41)
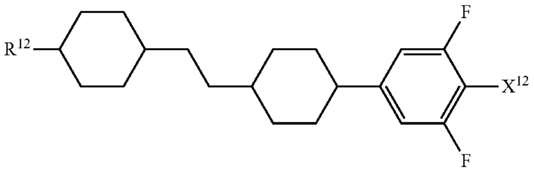
(5-42)
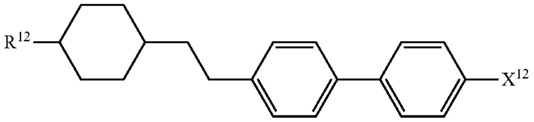
(5-43)
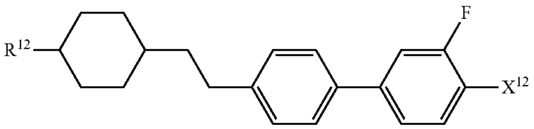
(5-44)
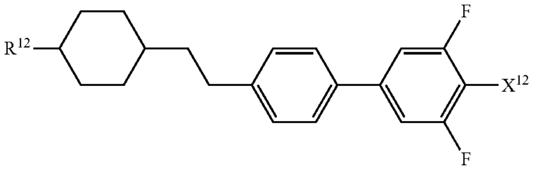
(5-45)
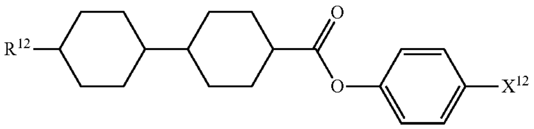
(5-46)
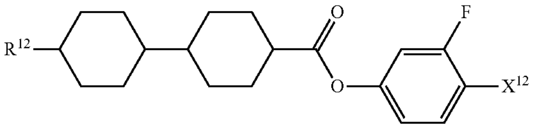
(5-47)
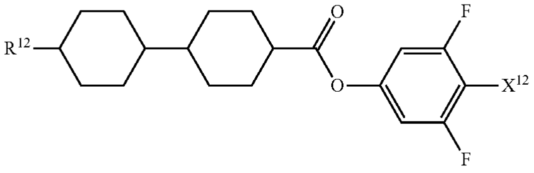
(5-48)
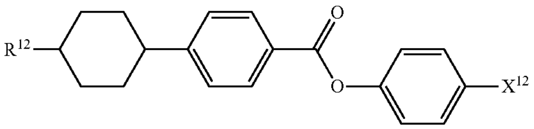
(5-49)
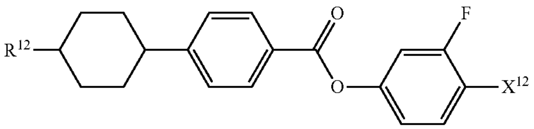

-continued (5-50)

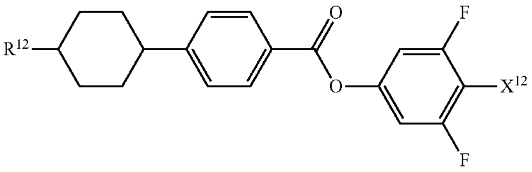

(5-51)

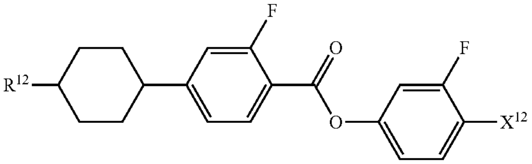

(5-52)

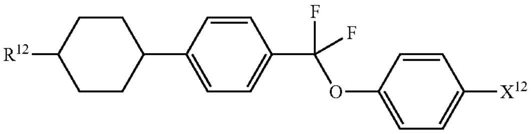

(5-53)

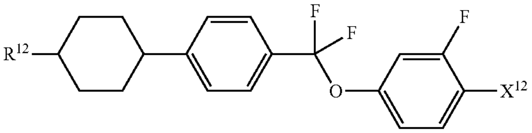

(5-54)

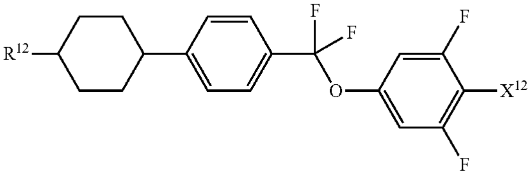

(5-55)

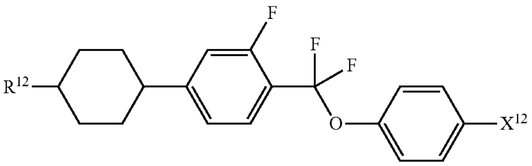

(5-56)

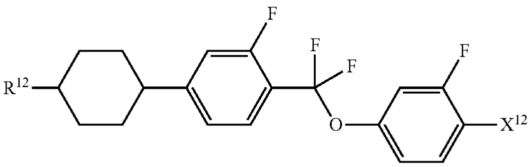

(5-57)

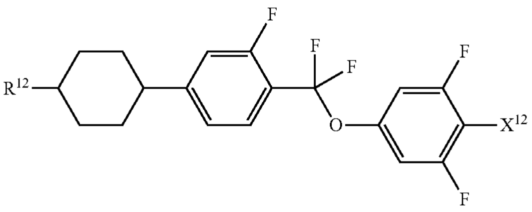

-continued (5-58)

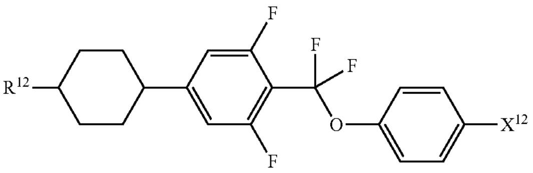

(5-59)

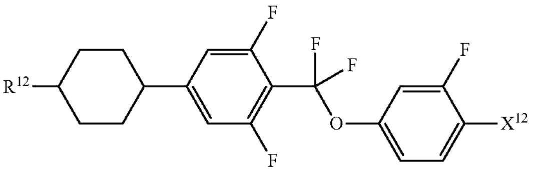

(5-60)

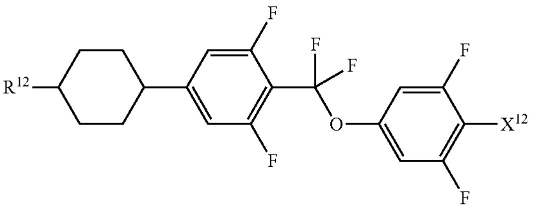

(5-61))

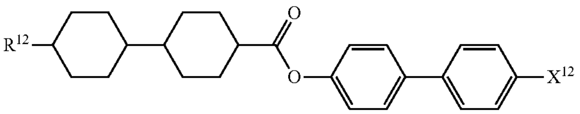

(5-62)

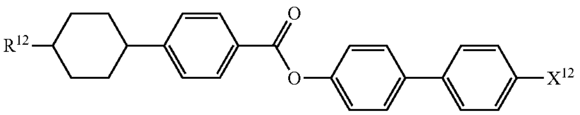

(5-63)

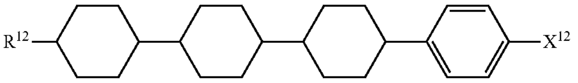

(5-64)

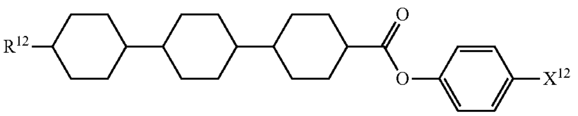

Component C has the positive dielectric anisotropy and a value of which is large, and therefore is mainly used for preparing a composition for the STN mode, the TN mode or the PSA mode. Dielectric anisotropy of the composition can be increased by adding component C. Component C is effective in extending the temperature range of the liquid crystal phase, adjusting the viscosity or adjusting the optical anisotropy. Component C is also useful for adjustment of the voltage-transmittance curve of the device.

When a composition for the STN mode or the TN mode is prepared, a content of component C is suitably in the range of 1 to 99% by weight, preferably in the range of 10 to 97% by weight, and further preferably in the range of 40 to 95% by weight, based on the weight of the composition. In the composition, the temperature range of the liquid crystal phase, the viscosity, the optical anisotropy, the dielectric anisotropy or the like can be adjusted by adding component E.

Component D includes compounds (6) to (12). The compounds have a benzene ring in which hydrogen in lateral positions are replaced by two pieces of halogen, such as 2,3-difluoro-1,4-phenylene. Specific preferred examples of components D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In the compounds (components D), definitions of $R^{13}$, $R^{14}$ and $R^{15}$ are identical to compounds (6) to (12) described in item 11.

(6-1)

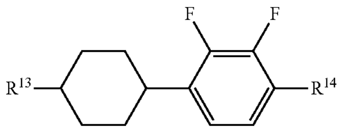

(6-2)

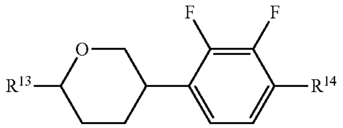

(6-3)

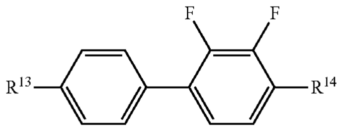

(6-4)

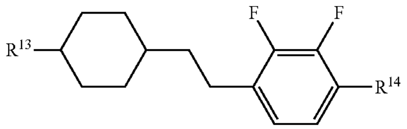

(6-5)

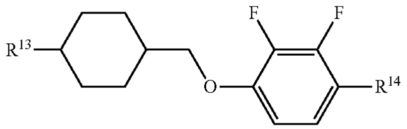

(6-6)

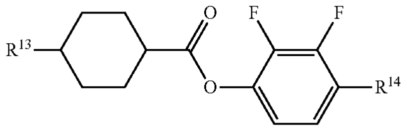

(6-7)

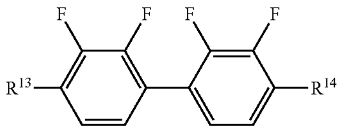

(6-8)

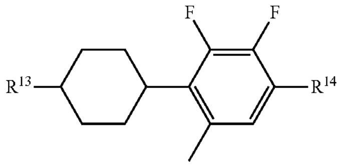

(7-1)

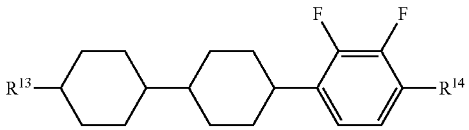

-continued (7-2)

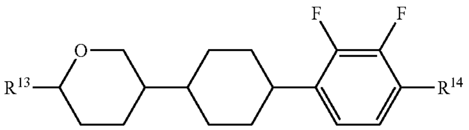

(7-3)

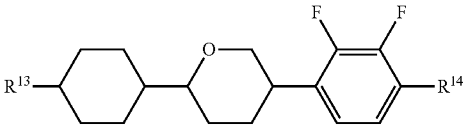

(7-4)

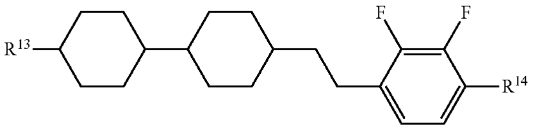

(7-5)

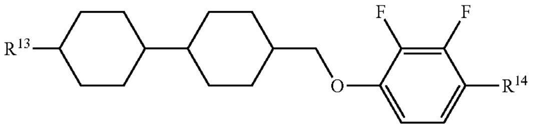

(7-6)

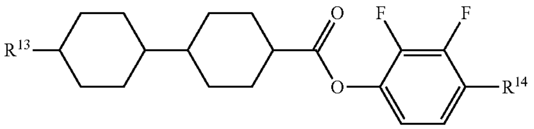

(7-7)

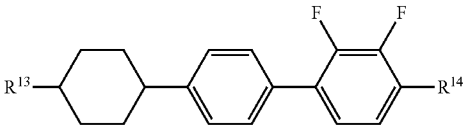

(7-8)

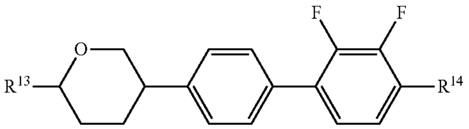

(7-9)

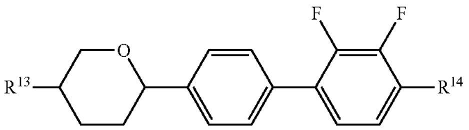

(7-10)

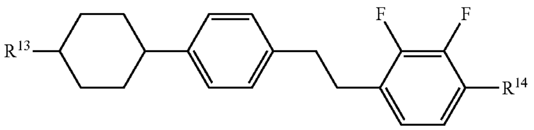

(7-11)

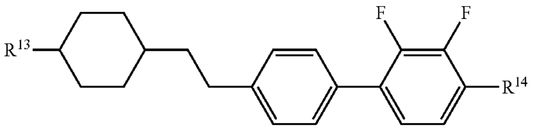

(7-12)

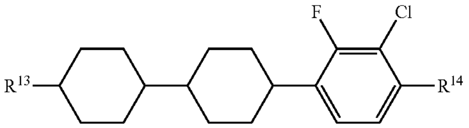

-continued
(7-13)
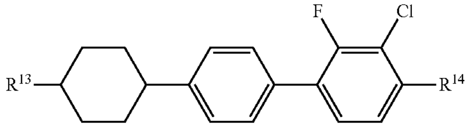
(7-14)
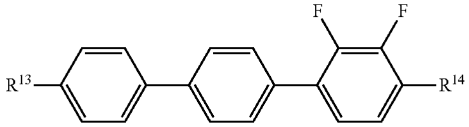
(7-15)
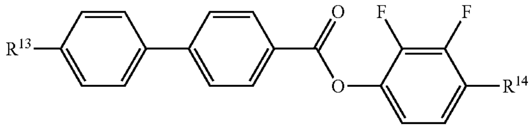
(7-16)
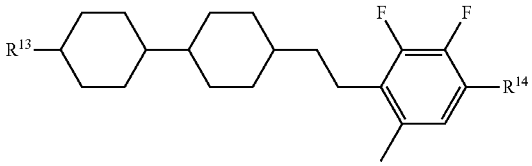
(7-17)
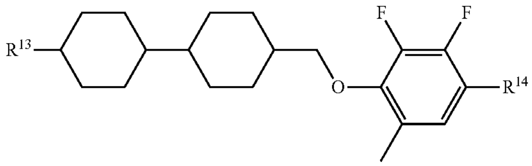
(8-1)
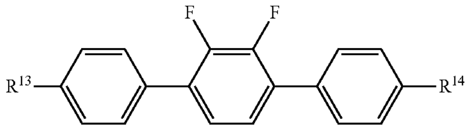
(9-1)
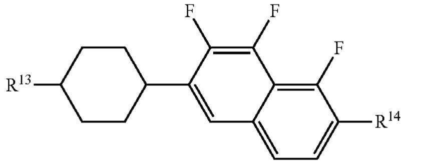
(9-2)
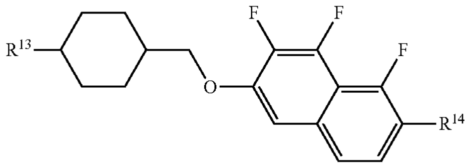
(9-3)
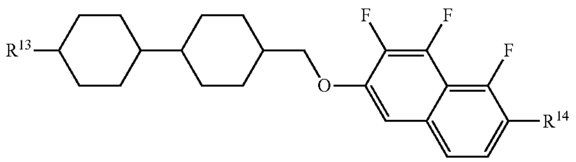
-continued
(10-1)
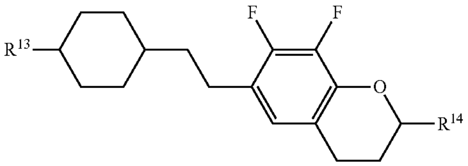
(10-2)
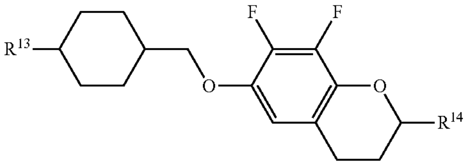
(10-3)
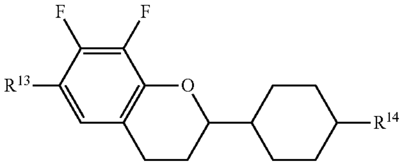
(10-4)
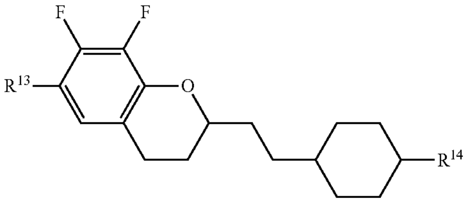
(10-5)
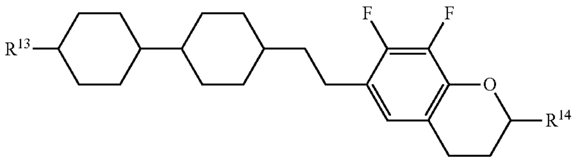
(10-6)
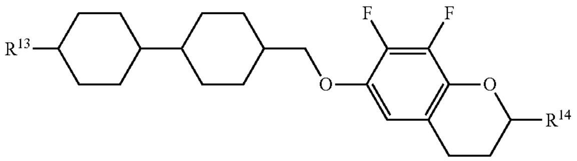
(10-7)
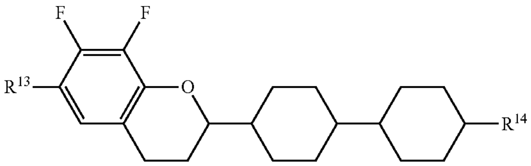
(10-8)
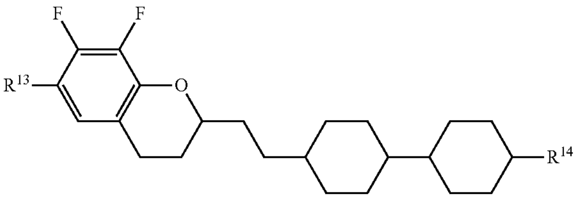

-continued (10-9)

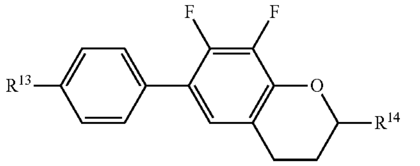

(10-10)

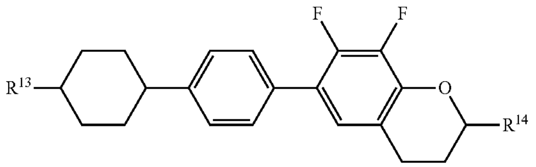

(10-11)

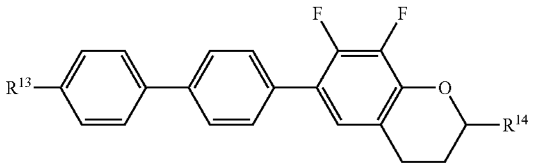

(11-1)

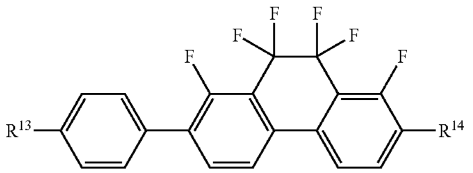

(11-2)

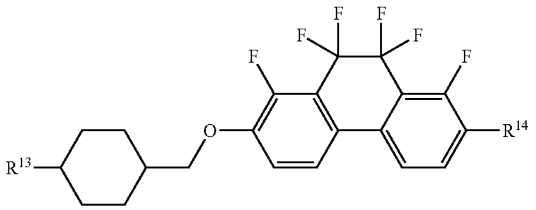

(11-3)

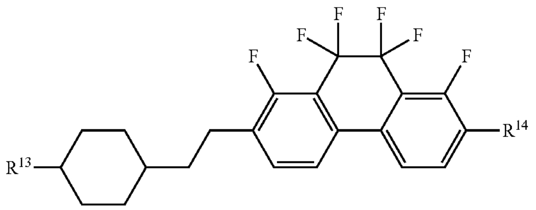

(12-1)

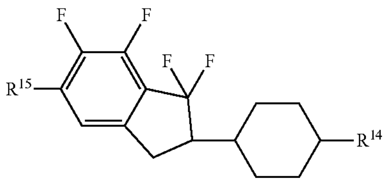

(12-2)

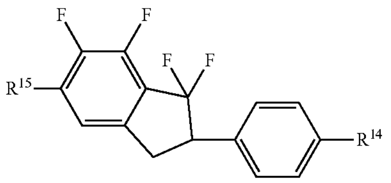

-continued (12-3)

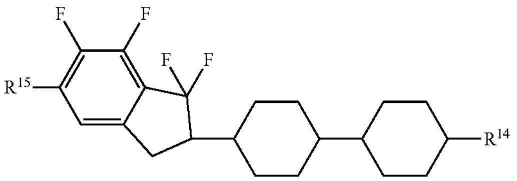

Component D is a compound having the negative dielectric anisotropy. Component D is mainly used for preparing a composition for the VA mode or the PSA mode. Among types of component D, compound (6) is a bicyclic compound, and therefore is mainly effective in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When a composition for the VA mode or the PSA mode is prepared, a content of component D is preferably in the range of 40% by weight or more, and further preferably in the range of 50 to 95% by weight, based on the weight of the composition. When component D is added to a composition having the positive dielectric anisotropy, the content of component D is preferably 30% by weight or less based on the weight of the composition. Addition of component D allows adjustment of the voltage-transmittance curve of the device.

Component E includes a compound in which two terminal groups are alkyl or the like. Specific preferred examples of components E include compounds (13-1) to (13-11), compounds (14-1) to (14-19) and compounds (15-1) to (15-7). In the compounds (components E), definitions of $R^{16}$ and $R^{17}$ are identical to compounds (13) to (15) described in item 12.

(13-1)

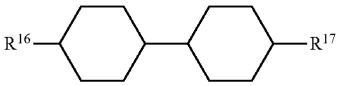

(13-2)

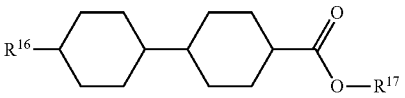

(13-3)

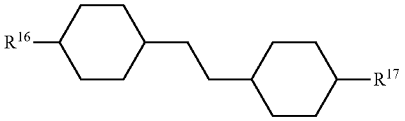

(13-4)

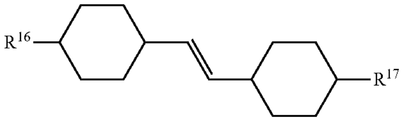

(13-5)

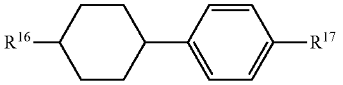

-continued
(13-6)
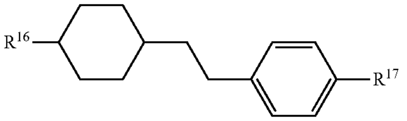
(13-7)
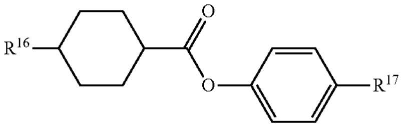
(13-8)
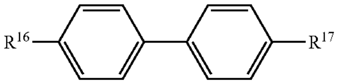
(13-9)
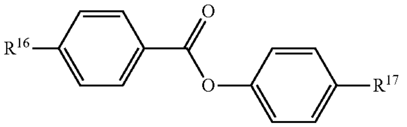
(13-10)
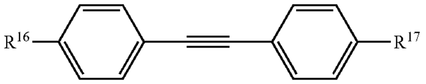
(13-11)
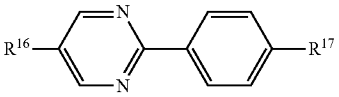
(14-1)
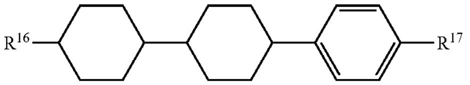
(14-2)
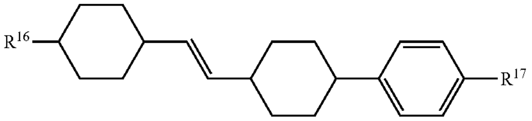
(14-3)
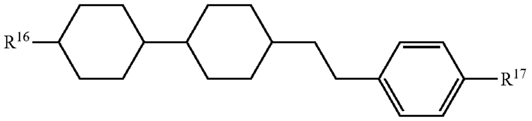
(14-4)
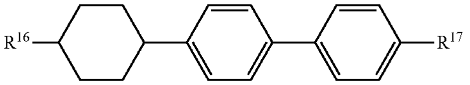
(14-5)
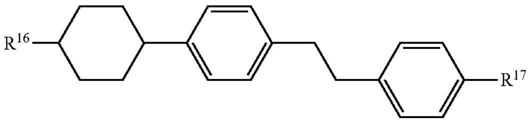
(14-6)
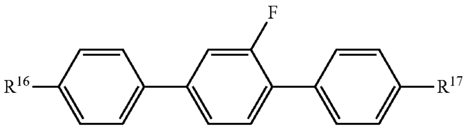
-continued
(14-7)
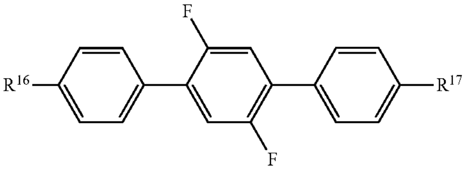
(14-8)
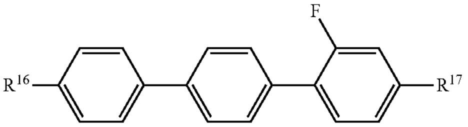
(14-9)
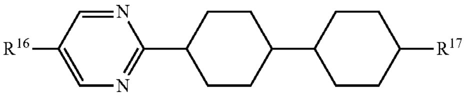
(14-10)
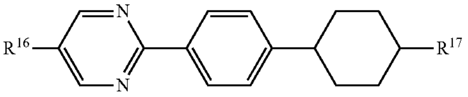
(14-11)
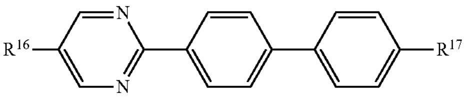
(14-12)
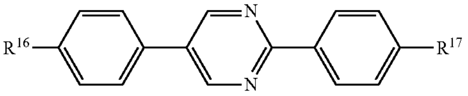
(14-13)
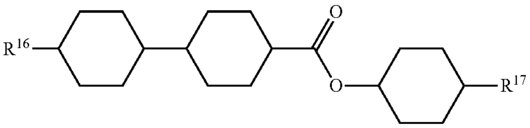
(14-14)
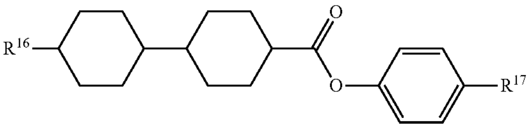
(14-15)
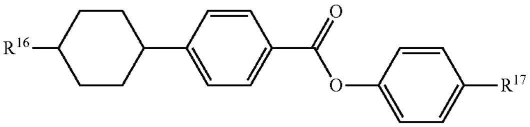
(14-16)
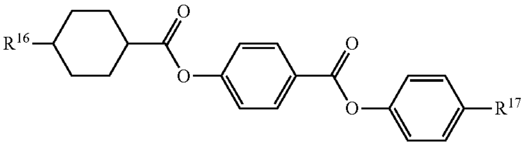
(14-17)
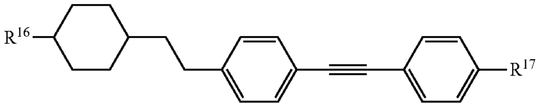

-continued (14-18)

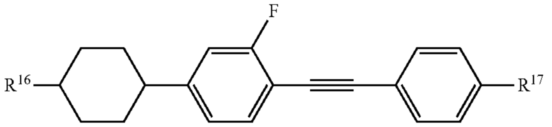

(14-19)

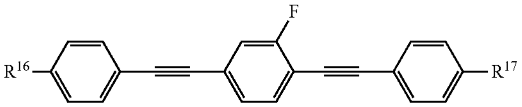

(15-1)

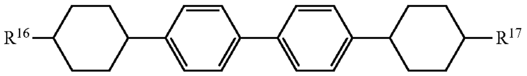

(15-2)

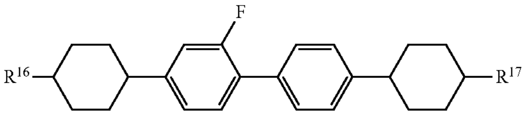

(15-3)

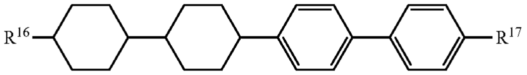

(15-4)

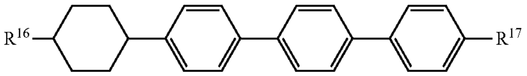

(15-5)

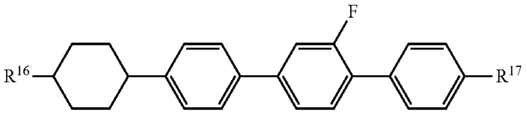

(15-6)

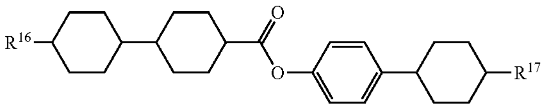

-continued (15-7)

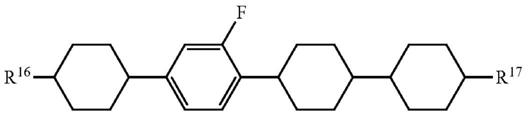

Component E has a small absolute value of dielectric anisotropy, and therefore is a compound close to neutrality. Compound (13) is mainly effective in adjusting the viscosity or adjusting the optical anisotropy. Compounds (14) and (15) are effective in extending the temperature range of the nematic phase by increasing the maximum temperature or effective in adjusting the optical anisotropy.

If a content of component E is increased, the dielectric anisotropy of the composition is decreased, but the viscosity is decreased. Thus, as long as a desired value of threshold voltage of the device is met, the content is preferably as large as possible. Accordingly, when the composition is prepared, the content of component E is preferably 30% by weight or more, and further preferably 40% by weight or more, based on the weight of the composition.

Preparation of composition (1) is performed by a method for dissolving required components at a high temperature, or the like. According to an application, an additive may be added to the composition. Specific examples of the additives include the optically active compound, the polymerizable compound, the polymerization initiator, the antioxidant, the ultraviolet light absorber, the light stabilizer, the heat stabilizer, the antifoaming agent and the dye. Such additives are well known to those skilled in the art, and described in literature.

Composition (1) may further contain at least one optically active compound. The optically active compound is effective in inducing helical structure in liquid crystal molecules to give a required twist angle, and thereby preventing a reverse twist. Specific preferred examples of the optically active compounds include compounds (Op-1) to (Op-18) described below.

(Op-1)

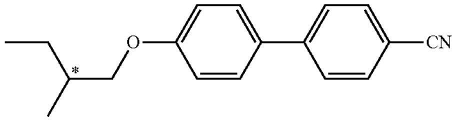

(Op-2)

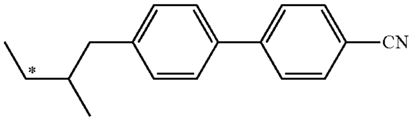

(Op-3)

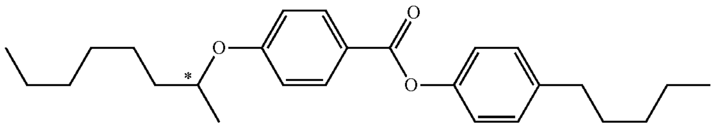

(Op-4)

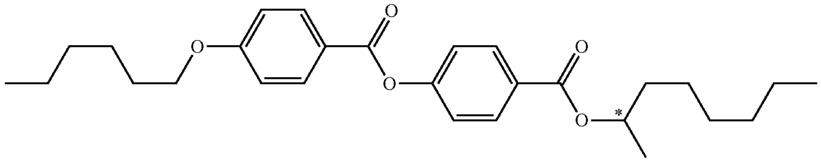

-continued
(Op-5)
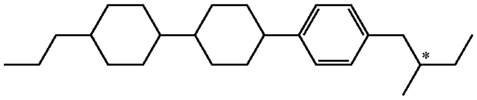
(Op-6)
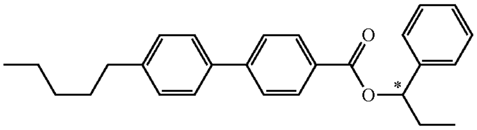
(Op-7)
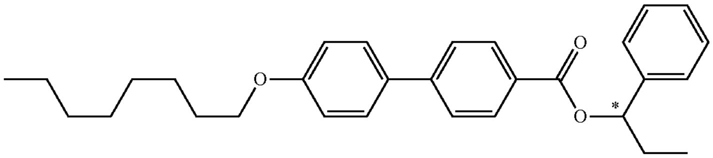
(Op-8)
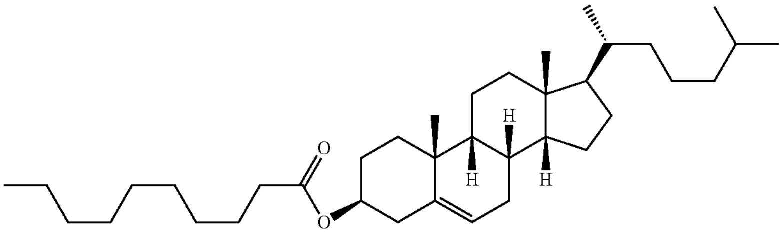
(Op-9)
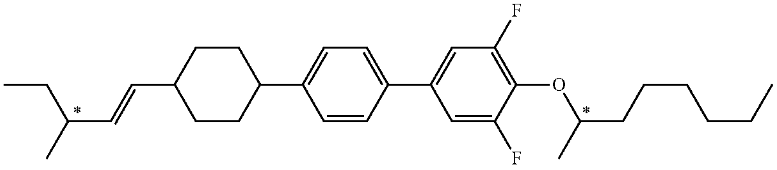
(Op-10)
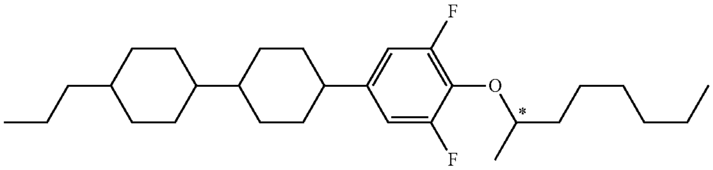
(Op-11)
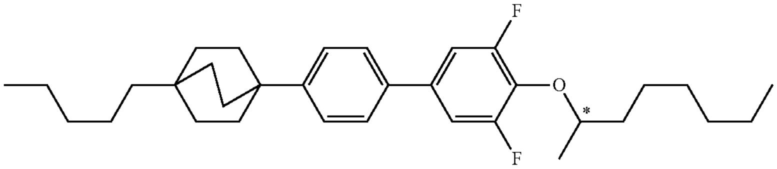
(Op-12)
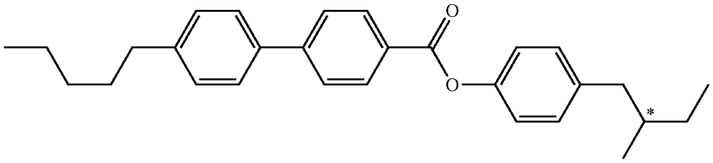
(Op-13)
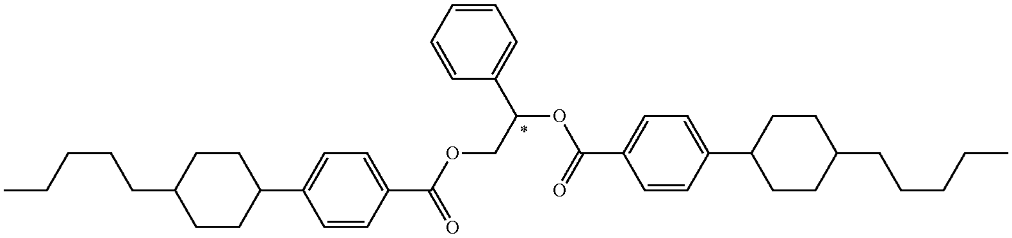

-continued (Op-14)

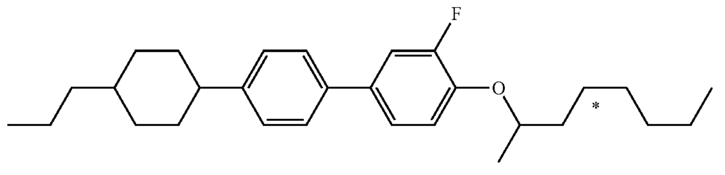

(Op-15)

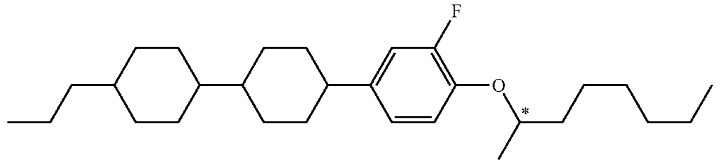

(Op-16)

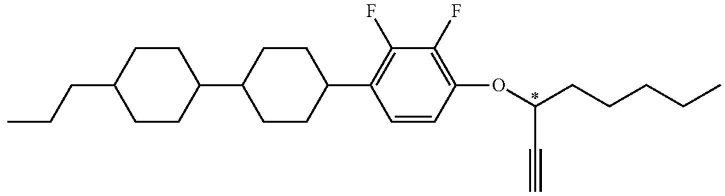

(Op-17)

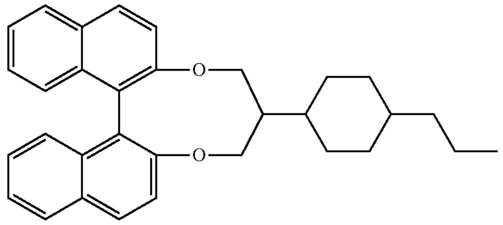

(Op-18)

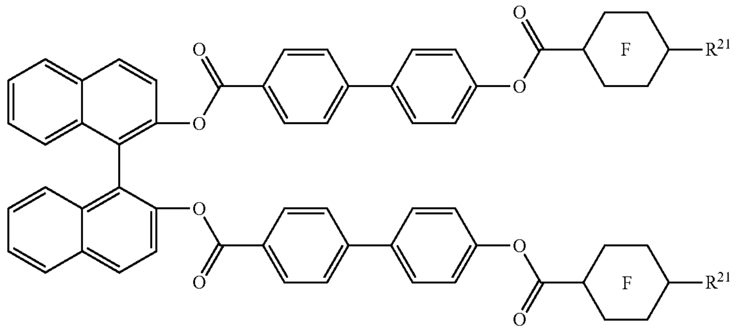

wherein, in compound (Op-18), ring F is 1,4-cyclohexylene or 1,4-phenylene, and $R^{21}$ is alkyl having 1 to 10 carbons.

In composition (1), a helical pitch is adjusted by adding such an optically active compound. The helical pitch is preferably adjusted in the range of 40 to 200 micrometers in a composition for the TFT mode and the TN mode. In a composition for the STN mode, the helical pitch is preferably adjusted in the range of 6 to 20 micrometers. In the case of a composition for the BTN mode, the helical pitch is preferably adjusted in the range of 1.5 to 4 micrometers. Two or more optically active compounds may be added for the purpose of adjusting temperature dependence of the helical pitch.

Composition (1) can also be used for the PSA mode by adding a polymerizable compound. Specific examples of the polymerizable compounds include acrylate, methacrylate, a vinyl compound, a vinyloxy compound, propenyl ether, an epoxy compound (oxirane, oxetane) and vinyl ketone. The polymerizable compound is polymerized by irradiation with ultraviolet or the like. An initiator such as a photopolymerization initiator may be added. Suitable conditions for polymerization, suitable types of the initiator and suitable amounts thereof are known to those skilled in the art and are described in literature. Specific preferred examples of the polymerizable compounds include compounds (M-1) to (M-12).

(M-1)
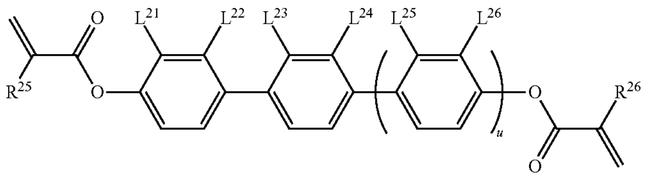
(M-2)
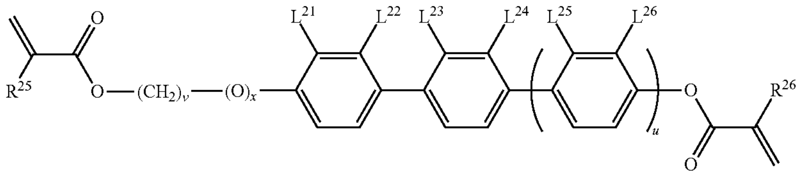
(M-3)
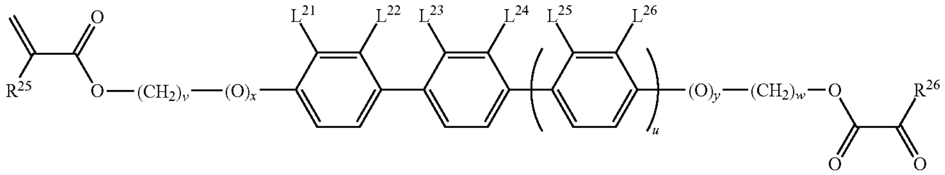
(M-4)
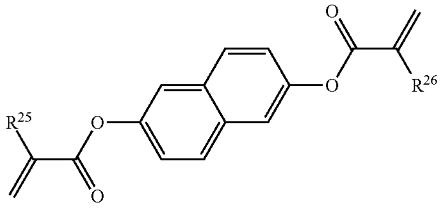
(M-5)
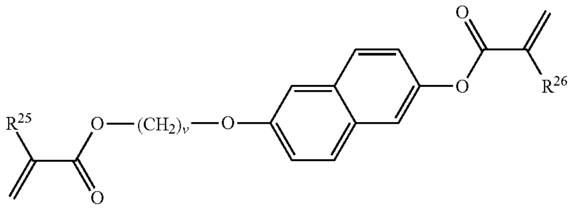
(M-6)
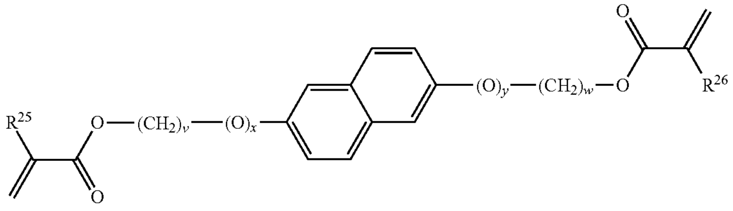
(M-7)
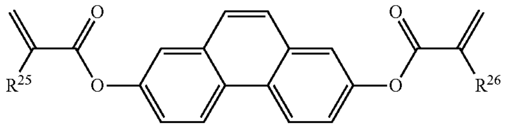
(M-8)
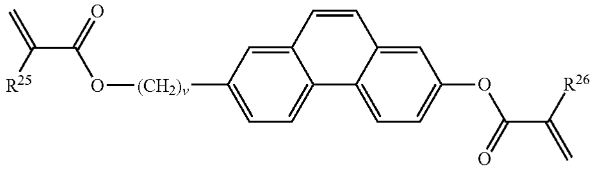

-continued (M-9)

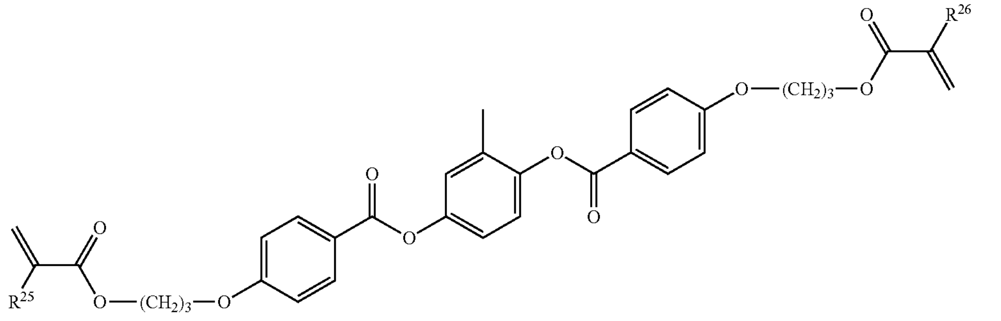

(M-10)

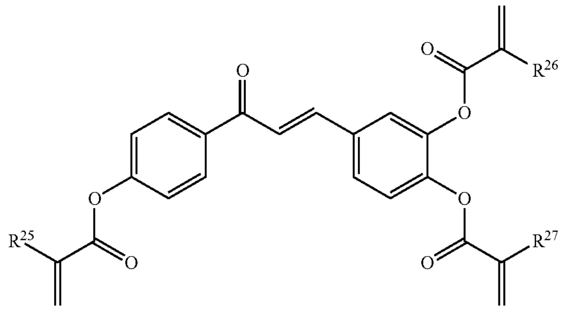

(M-11)

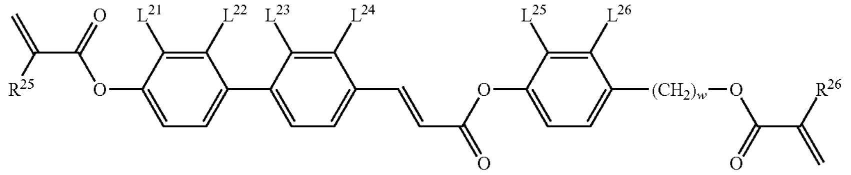

(M-12)

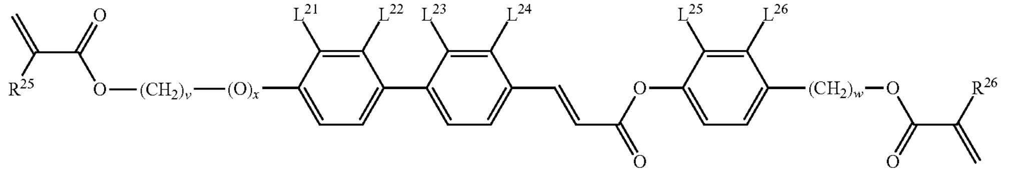

In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

The antioxidant is effective for maintaining the large voltage holding ratio. Specific preferred examples of the antioxidants include compounds (AO-1) and (AO-2) described below, IRGANOX 415, IRGANOX 565, IRGANOX 1010, IRGANOX 1035, IRGANOX 3114 and IRGANOX 1098 (trade names: BASF SE). The ultraviolet light absorber is effective in preventing a decrease of the maximum temperature. Specific preferred examples of the ultraviolet light absorbers include a benzophenone derivative, a benzoate derivative and a triazole derivative. Specific examples include compounds (AO-3) and (AO-4) described below, TINUVIN 329, TINUVIN P, TINUVIN 326, TINUVIN 234, TINUVIN 213, TINUVIN 400, TINUVIN 328 and TINUVIN 99-2 (trade names: BASF SE) and 1,4-diazabicyclo[2.2.2]octane (DABCO). The light stabilizer such as an amine having steric hindrance is preferred for maintaining the large voltage holding ratio. Specific preferred examples of the light stabilizers include compounds (AO-5) and (AO-6) described below, TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The antifoaming agent is effective for preventing foam formation. Specific preferred examples of the antifoaming agents include dimethyl silicone oil and methylphenyl silicone oil.

(AO-1)

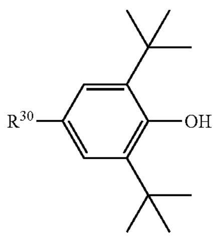

-continued (AO-2)

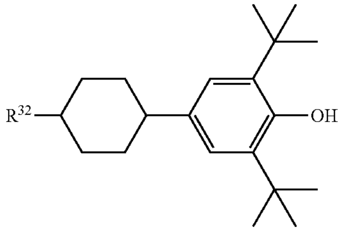

(AO-3)

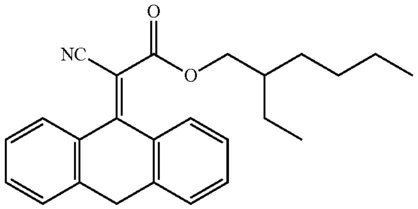

(AO-4)

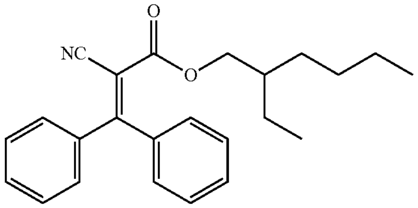

(AO-5)

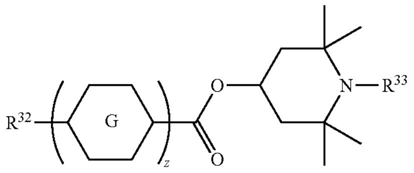

(AO-6)

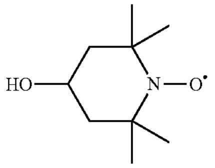

In compound (AO-1), $R^{30}$ is alkyl having 1 to 20 carbons, alkoxy having 1 to 20 carbons, —$COOR^{31}$ or —$CH_2CH_2COOR^{31}$, in which $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl or O. (oxygen radical); ring G is 1,4-cyclohexylene or 1,4-phenylene; and Z is 1, 2 or 3.

Composition (1) can also be used for a guest host (GH) mode by adding a dichroic dye such as a merocyanine type, a styryl type, an azo type, an azomethine type, an azoxy type, a quinophthalone type, an anthraquinone type and a tetrazine type.

3. Liquid Crystal Display Device

Composition (1) can be used in the liquid crystal display device having an operating mode such as the PC mode, the TN mode, the STN mode, the OCB mode and the PSA mode, and driven by an active matrix (AM) mode. Composition (1) can also be used in the liquid crystal display device having the operating mode such as the PC mode, the TN mode, the STN mode, the OCB mode, the VA mode and the IPS mode, and driven by a passive matrix (PM) mode. The AM mode and the PM mode devices can also be applied to any of a reflective type, a transmissive type and a transflective type.

Composition (1) can also be used in a nematic curvilinear aligned phase (NCAP) device prepared by microencapsulating a nematic liquid crystal, a polymer dispersed liquid crystal display device (PDLCD) and a polymer network liquid crystal display device (PNLCD) in which a three-dimensional network-polymer is formed in the liquid crystal.

EXAMPLES

The invention will be described in greater detail by way of Examples. The invention is not limited by the Examples.

1-1. Example of Compound (1)

Compound (1) was prepared according to procedures described below. The prepared compound was identified by a method such as an NMR analysis. Physical properties of the compound were measured by methods described below.

NMR Analysis

For measurement, DRX-500 made by Bruker BioSpin Corporation was used. In $^{1}H$-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}F$-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Sample for Measurement

Upon measuring phase structure and transition temperature, a liquid crystal compound itself was used as a sample. Upon measuring physical properties such as a maximum temperature of a nematic phase, viscosity, an optical anisotropy and a dielectric anisotropy, a composition prepared by mixing the compound with a base liquid crystal was used as a sample.

When a sample in which the compound was mixed with the base liquid crystal was used, measurement was carried out as described below. The sample was prepared by mixing 15% by weight of the compound and 85% by weight of the base liquid crystal. From a measured value of the sample, an extrapolated value was calculated according to an extrapolation method represented by the following formula, and the calculated value was described: [extrapolated value]=(100×[measured value of a sample]−[% by weight of a base liquid crystal]×[measured value of the base liquid crystal])/[% by weight of a compound].

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample were measured at a ratio at which no crystal (or no smectic phase) precipitated at 25° C. In addition, unless otherwise noted, the ratio of the compound to the base liquid crystal was (15% by weight:85% by weight).

As the base liquid crystal, base liquid crystal (i) described below was used. Proportions of components in base liquid crystal (i) were expressed in terms of % by weight.

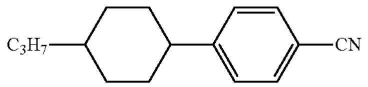

24%

-continued

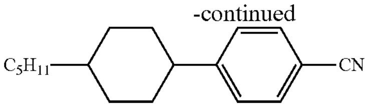

36%

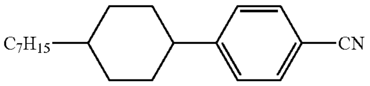

25%

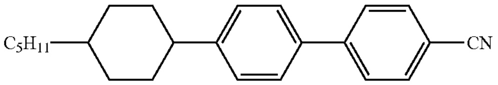

15%

Measuring Method

Physical properties were measured according to methods described below. Most of the measuring methods are applied as described in the Standard of Japan Electronics and Information Technology Industries Association (hereinafter abbreviated as JEITA) (JEITA ED-2521B) discussed and established by JEITA, or modified thereon. No TFT was attached to a TN device used for measurement.

(1) Phase Structure

A sample was placed on a hot plate in a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to an isotropic liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at Low Temperature

Samples in which the base liquid crystal and the compound were mixed for proportions of the compounds to be 20% by weight, 15% by weight, 10% by weight, 5% by weight, 3% by weight and 1% by weight were prepared, and put in glass vials. After the glass vials were kept in freezers at −10° C. or −20° C. for a predetermined period of time, whether or not crystals or a smectic phase precipitated was observed.

(4) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of a compound and the base liquid crystal, the maximum temperature was expressed in terms of a symbol $T_{NI}$. When the sample was a mixture of a compound and component B or the like, the maximum temperature was expressed in terms of a symbol NI.

(5) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as $T_C \leq -20°$ C. A minimum temperature of the nematic phase may be occasionally abbreviated as "minimum temperature."

(6) Viscosity (Bulk Viscosity; η; Measured at 20° C.; mPa·s)

For measurement, a cone-plate (E type) rotational viscometer made by Tokyo Keiki Inc. was used.

(7) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) on page 40 of the paper presented by M. Imai et al. A value of a dielectric anisotropy required for the calculation was determined using the device by which the rotational viscosity was measured and by a method described below.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n||) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n||−n⊥.

(9) Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈||) of liquid crystal molecules in a major axis direction was measured. Sine waves (0.5 V, 1 kHz) were applied to the device, and after 2 seconds, a dielectric constant ($\epsilon\perp$) of the liquid crystal molecules in a minor axis direction was measured. A value of dielectric anisotropy was calculated from an equation: $\Delta\epsilon=\epsilon\|-\epsilon\perp$.

(10) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(13) Voltage Holding Ratio (VHR-2; Measured at 80° C.; %)

A voltage holding ratio (VHR-2) was determined according to method identical with the method in VHR-1 except that measurement was carried out at 80° C.

Raw Material

Solmix A-11 (trade name) is a mixture of ethanol (85.5%), methanol (13.4%) and isopropanol (1.1%), and was purchased from Japan Alcohol Trading Co., Ltd.

Example 1

Synthesis of 4-((3,5-difluoro-4-(1,1,3,3-tetrafluoroallyl)oxy)phenoxy)difluoromethyl)-3,5-difluoro-4'-propyl-1,1'-biphenyl (No. 1-2-73)

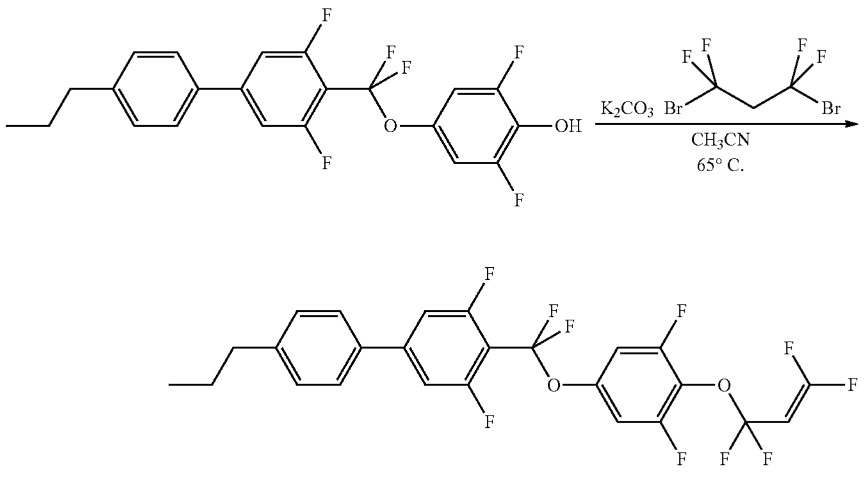

(No. 1-2-73)

(11) Threshold Voltage (Vth; Measured at 25° C.; V)

For measurement, an LCD5100 luminance meter made by Otsuka Electronics Co., Ltd. was used. A light source was a halogen lamp. A sample was put in a normally white mode TN device in which a distance (cell gap) between two glass substrates was about 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable Then, 4-((3,5-difluoro-4'-propyl-[1,1'-biphenyl]-4-yl)difluoromethoxy)-2,6-difluorophenol (2.00 g, 4.69 mmol) prepared by the method described in JP 2007-277127 A, potassium carbonate (2.16 g, 15.62 mmol) and 1,3-dibromo-1,1,3,3-tetrafluoropropane (2.15 g, 7.83 mmol) were stirred in acetonitrile at 65° C. for 3 hours. A resulting reaction mixture was poured into water and subjected to extraction with toluene. An organic layer was washed with water and saturated brine, and then dried over magnesium sulfate, and the solvent was distilled off with an evaporator. A residue was purified by silica gel chromatography and recrystallization to obtain compound (No. 1-2-73) (yield: 62%).

$^1$H-NMR ($CDCl_3$) δ 7.50-7.48 (m, 2H), 7.30-7.29 (m, 2H), 7.22-7.20 (m, 2H), 7.00-6.97 (m, 2H), 5.00-4.93 (m, 1H), 2.66-2.63 (m, 2H), 1.68 (sex, J=7.6 Hz, 2H), 0.97 (t, J=7.3 Hz, 3H).

Physical properties of compound (No. 1-2-73) were as described below. Phase transition temperature: C 52.5 I. Maximum temperature (NI)=39.0° C.; dielectric anisotropy ($\Delta\epsilon$)=16.2; optical anisotropy (Δn)=0.150; viscosity (η)=35.5 mPa·s.

Example 2

Synthesis of 4-(3,5-difluoro-4-((1,1,3,3-tetrafluoroallyl)oxy)phenyl)-4'-propyl-1,1'-bi(cyclohexane) (No. 1-2-40)

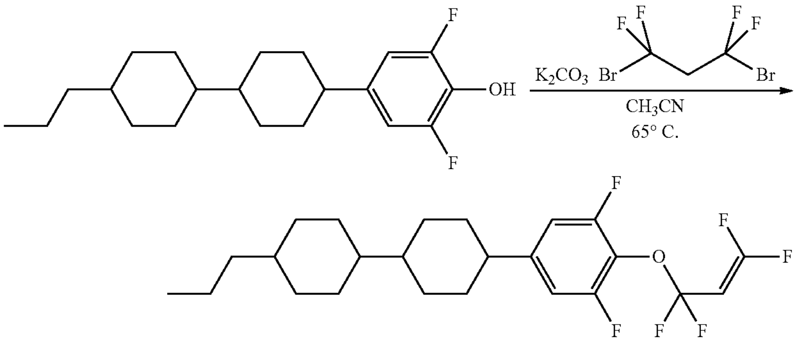

(No. 1-2-40)

Compound (No. 1-2-40) was obtained by using 2,6-difluoro-4-(4'-propyl-[1,1'-bi(cyclohexane)]-4-yl)phenol (3.00 g, 8.92 mmol) prepared by the method described in JP 2007-277127 A, according to method identical with Example 1 (yield: 75%).

$^1$H-NMR ($CDCl_3$) 6.83-6.79 (m, 2H), 4.99-4.91 (m, 1H), 2.44-2.38 (m, 1H), 1.91-1.84 (m, 4H), 1.78-1.71 (m, 4H), 1.38-1.23 (m, 5H), 1.16-0.95 (m, 8H), 0.89-0.82 (m, 5H).

Physical properties of compound (No. 1-2-40) were as described below. Phase transition temperature: C 46.0N 172 I. Maximum temperature (NI)=116° C.; dielectric anisotropy (Δ∈)=6.1; optical anisotropy (Δn)=0.104; viscosity (η)=33.5 mPa·s.

Example 3

Synthesis of 1-(4-propylcyclohexyl)-4-((1,1,3,3-tetrafluoroallyl)oxy)benzene (No. 1-1-9)

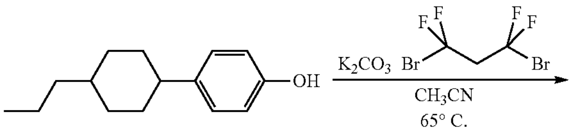

-continued

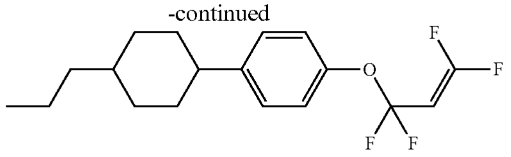

(No. 1-1-9)

Compound (No. 1-1-9) was obtained by using 4-(4-propylcyclohexyl)phenol (2.00 g, 9.16 mmol) prepared by the method described in JP 2007-277127 A, according to method identical with Example 1 (yield: 41%).

$^1$H-NMR ($CDCl_3$) δ 7.18-7.17 (m, 2H), 7.10-7.08 (m, 2H), 4.90-4.83 (m, 1H), 2.49-2.43 (m, 1H), 1.89-1.85 (m, 4H), 1.46-1.25 (m, 5H), 1.23-1.19 (m, 2H), 1.08-1.00 (m, 2H), 0.90 (t, J=7.3 Hz, 3H).

Physical properties of compound (No. 1-1-9) were as described below. Phase transition temperature: C 11.8 I. Maximum temperature (NI)=7.0° C.; dielectric anisotropy (Δ∈)=2.77; optical anisotropy (Δn)=0.0637; viscosity (η)=15.6 mPa·s.

Example 4

Synthesis of 4-propyl-4'-(4-((1,1,3,3-tetrafluoroallyl)oxy)phenoxy)-1,1'-bi(cyclohexane) (No. 1-2-36)

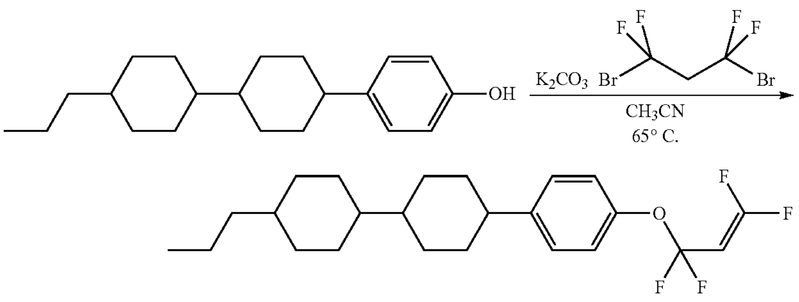

(No. 1-2-36)

Compound (No. 1-2-36) was obtained by using 4-(4'-propyl-[1,1'-bi(cyclohexane)]-4-yl)phenol (2.00 g, 6.66 mmol) prepared by the method described in JP 2007-277127 A, according to method identical with Example 1 (yield: 8.6%).

$^{1}$H-NMR ($CDCl_3$) δ 7.20-7.19 (m, 2H), 7.12-7.10 (m, 2H), 4.93-4.85 (m, 1H), 2.48-2.43 (m, 1H), 1.94-1.85 (m, 3H), 1.80-1.75 (m, 3H), 1.43-1.28 (m, 8H), 1.18-0.98 (m, 7H), 0.91-0.85 (m, 5H).

Physical properties of compound (No. 1-2-36) were as described below. Phase transition temperature: C 32.5 $S_B$ 180 N 192 I. Maximum temperature (NI)=151° C.; dielectric anisotropy (Δ∈)=3.43; optical anisotropy (Δn)=0.117; viscosity (η)=13.5 mPa·s.

Example 5

Synthesis of 2'-fluoro-4"-propyl-4'-((1,1,3,3-tetrafluoroallyl)oxy)-1,1':4'-1"-terphenyl (No. 1-2-3)

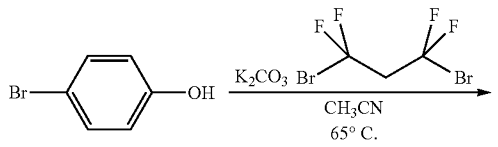

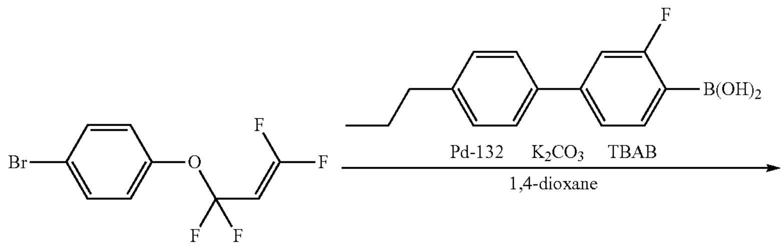

(T-1)

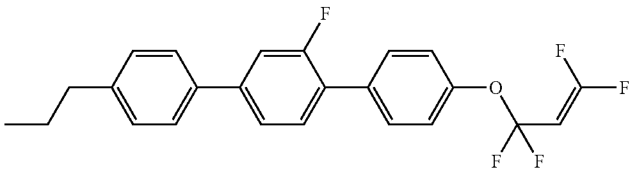
(No. 1-2-3)

Synthesis of Compound (T-1)

Then, 4-bromophenol (10.0 g, 57.8 mmol), potassium carbonate (2.26 g, 192.5 mmol) and 1,3-dibromo-1,1,3,3-tetrafluoropropane (26.4 g, 96.5 mmol) were stirred in acetonitrile at 65° C. for 3 hours. A resulting reaction mixture was poured into water and subjected to extraction with pentane. An organic layer was washed with water and saturated brine, and then dried over magnesium sulfate, and the solvent was distilled off with an evaporator. A residue was purified by silica gel chromatography to obtain 1-bromo-4-((1,1,3,3-tetrafluoroallyl)oxy)benzene (T-1) (yield: 67%).

Synthesis of Compound (1-2-3)

Compound (T-1) (6.00 g, 21.1 mmol) obtained above, 3-fluoro-4'-propyl-[1,1'-biphenyl]-4-ylboronic acid (5.98 g, 23.2 mmol), Pd-132 (0.15 g, 0.21 mmol), potassium carbonate (5.82 g, 42.1 mmol) and TBAB (2.41 g, 7.48 mmol) were added to a reaction vessel under a nitrogen atmosphere, and a resulting mixture was stirred in 1,4-dioxane at 100° C. for 8 hours. The resulting reaction mixture was poured into water and subjected to extraction with toluene. An organic layer was washed with water and saturated brine, and then dried over magnesium sulfate, and the solvent was distilled off with an evaporator. A residue was purified by silica gel chromatography and recrystallization to obtain compound (No. 1-2-3) (yield: 15%).

$^{1}$H-NMR ($CDCl_3$) δ 7.59-7.57 (m, 2H), 7.54-7.53 (m, 2H), 7.49-7.43 (m, 2H), 7.40-7.38 (m, 1H), 7.29-7.27 (m, 4H), 4.96-4.88 (m, 1H), 2.66-2.63 (m, 2H), 1.69 (sex, J=7.6 Hz, 2H), 0.98 (t, J=7.5 Hz, 3H).

Physical properties of compound (No. 1-2-3) were as described below. Phase transition temperature: C 57.2 $S_E$ 81.6 $S_B$ 117 N 181 I. Maximum temperature (NI)=120° C.; dielectric anisotropy (Δ∈)=8.77; optical anisotropy (Δn)=0.230; viscosity (η)=18.4 mPa·s.

Example 6

Synthesis of 4-(4-propylcyclohexyl)-4'-((1,1,3,3-tetrafluoroallyl)oxy)-1,1'-biphenyl (No. 1-2-21)

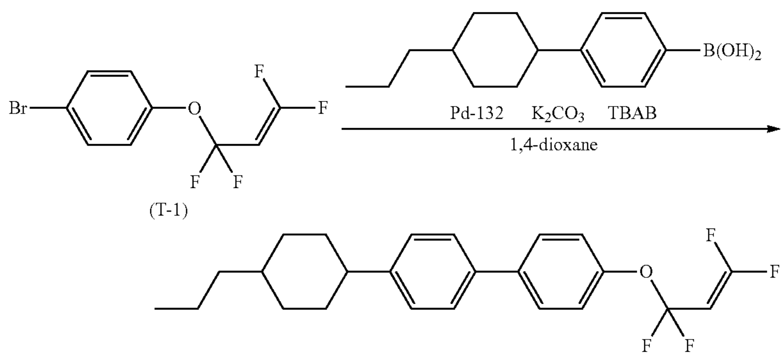

(T-1)

(No. 1-2-21)

Synthesis of Compound (1-2-21)

Compound (T-1) (10.6 g, 37.4 mmol) obtained in Example 5, (4(4-propylcyclohexyl)phenyl)boronic acid (10.1 g, 41.1 mmol), Pd-132 (0.26 g, 0.37 mmol), potassium carbonate (10.3 g, 74.8 mmol) and TBAB (2.41 g, 7.48 mmol) were added to a reaction vessel under a nitrogen atmosphere, and a resulting mixture was stirred in 1,4-dioxane at 100° C. for 8 hours. The resulting reaction mixture was poured into water and subjected to extraction with toluene. An organic layer was washed with water and saturated brine, and then dried over magnesium sulfate, and the solvent was distilled off with an evaporator. A residue was purified by silica gel chromatography and recrystallization to obtain compound (No. 1-2-21) (yield: 14%).

$^1$H-NMR ($CDCl_3$) δ 7.56-7.53 (m, 2H), 7.49-7.48 (m, 2H), 7.29-7.27 (m, 2H), 7.24-7.22 (m, 2H), 4.94-4.86 (m, 1H), 2.54-2.48 (m, 1H), 2.54-2.48 (m, 1H), 1.94-1.87 (m, 4H), 1.53-1.45 (m, 2H), 1.43-1.28 (m, 3H), 1.25-1.20 (m, 2H), 1.11-1.03 (m, 2H), 0.90 (t, J=7.4, 3H).

Physical properties of compound (No. 1-2-21) were as described below. Phase transition temperature: C 20.5 $S_B$ 178 $S_A$ 189 I. Maximum temperature (NI)=141° C.; dielectric anisotropy ($\Delta\epsilon$)=5.23; optical anisotropy (Δn)=0.170; viscosity (η)=13.1 mPa·s.

Example 7

Synthesis of 5-propyl-2-(4-((1,1,3,3-tetrafluoroallyl)oxy)phenyl)tetrahydro-2H-pyran (No. 1-1-12)

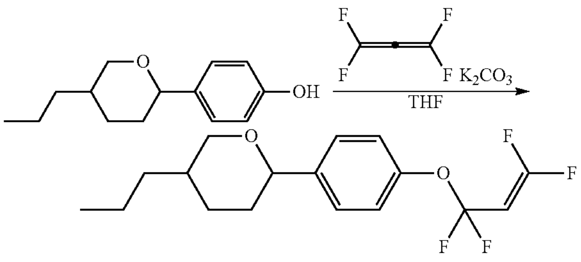

(No. 1-1-12)

Synthesis of Compound (1-1-12)

Then, 4-(5-propyltetrahydro-2H-pyrane-2-yl)phenol (2.00 g, 9.08 mmol) prepared by the method described in JP 2007-277127 A, and potassium carbonate (1.63 g, 11.8 mmol) were added to a reaction vessel under a nitrogen atmosphere, and a resulting mixture was stirred in THF at room temperature for 12 hours. In addition, tetrafluoroallene obtained by allowing 1,1,3,3,3-pentafluoropropene (4.80 g, 36.3 mmol) to react with t-butyllithium of 1.6M (22.7 mL, 36.3 mmol) in diethyl ether at −70° C. were all used. A resulting reaction mixture was poured into water and subjected to extraction with toluene. An organic layer was washed with water and saturated brine, and then dried over magnesium sulfate, and the solvent was distilled off with an evaporator. A residue was purified by silica gel chromatography and recrystallization to obtain compound (No. 1-1-12) (yield: 27%).

$^1$H-NMR ($CDCl_3$) δ 7.35-7.32 (m, 2H), 7.15-7.13 (m, 2H), 4.89-4.82 (m, 1H), 4.27-4.24 (m, 1H), 4.10-4.06 (m, 1H), 3.21 (t, J=11.2 Hz, 1H), 2.01-1.96 (m, 1H), 1.88-1.84 (m, 1H), 1.72-1.52 (m, 2H), 1.43-1.08 (m, 5H), 0.92 (t, J=7.4 Hz, 3H).

Physical properties of compound (No. 1-1-12) were as described below. Phase transition temperature: C 30.4 I. Maximum temperature (NI)=−1.6° C.; dielectric anisotropy ($\Delta\epsilon$)=4.1; optical anisotropy (Δn)=0.057; viscosity (η)=−11.9 mPa·s.

Example 8

Synthesis of 4-(4-((1,1,3,3-tetrafluoroallyl)oxy)phenyl)-4'-vinyl-1,1'-bi(cyclohexane) (No. 1-2-58)

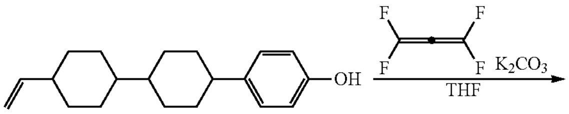

-continued

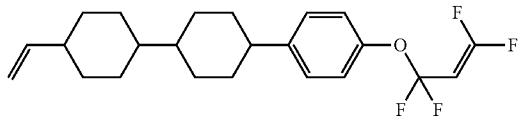

(No. 1-2-58)

Synthesis of Compound (1-2-58)

Compound (No. 1-2-58) was obtained by using 4-(4'-vinyl[1,1'-bi(cyclohexane)]-4-yl)phenol (2.51 g, 8.82 mmol) prepared by the method described in JP 2007-277127 A, according to method identical with Example 7 (yield: 26%).

$^1$H-NMR ($CDCl_3$) δ 7.18-7.16 (m, 2H), 7.10-7.08 (m, 2H), 5.82-5.75 (m, 1H), 4.98-4.94 (m, 1H), 4.90-4.83 (m, 2H), 2.47-2.41 (m, 1H), 1.92-1.79 (m, 9H), 1.44-1.37 (m, 2H), 1.17-1.07 (m, 8H).

Physical properties of compound (No. 1-2-58) were as described below. Phase transition temperature: C 32.7 $S_B$ 125.6 N 172.3 I. Maximum temperature (NI)=140.4° C.; dielectric anisotropy (Δε)=3.0; optical anisotropy (Δn)=0.124; viscosity (η)=7.6 mPa·s.

Compounds (No. 1-1-1) to (No. 1-1-32), (No. 1-2-1) to (No. 1-2-120), (No. 1-3-1) to (No. 1-3-150) and (No. 1-4-1) to (No. 1-4-32) described below can be prepared according to synthesis methods of compounds (1) described above and synthesis procedures described in Examples 1 to 4.

1-1-1

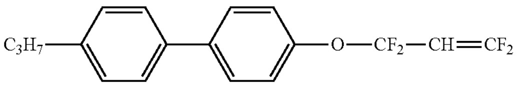

1-1-2

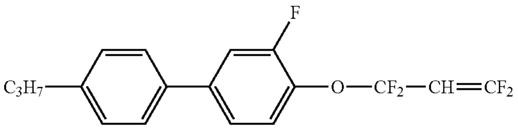

1-1-3

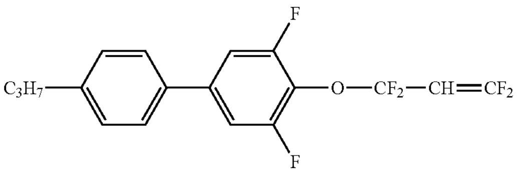

1-1-4

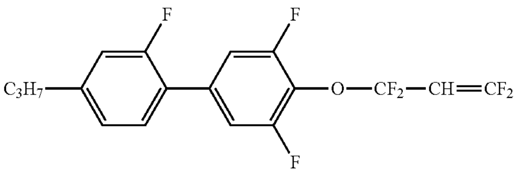

1-1-5

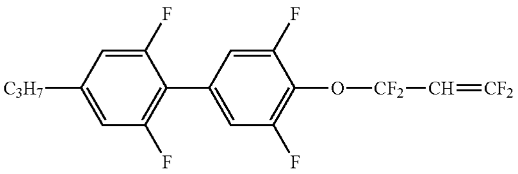

-continued 1-1-6

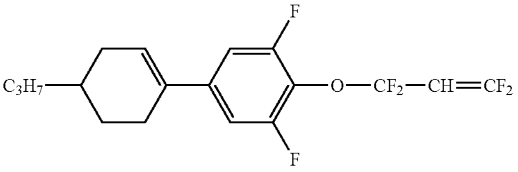

1-1-7

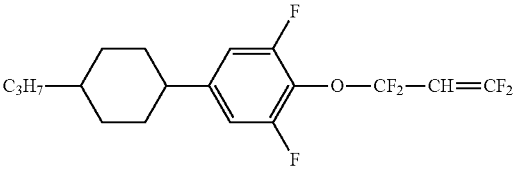

1-1-8

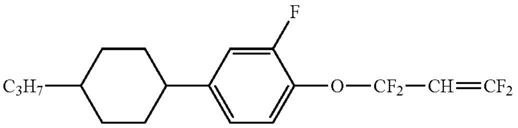

1-1-9

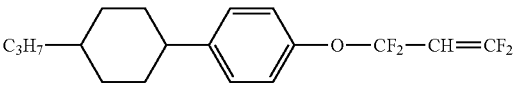

1-1-10

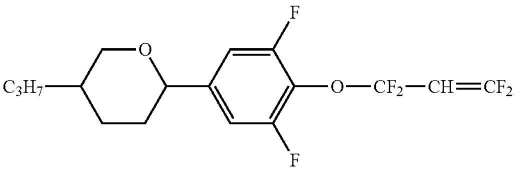

1-1-11

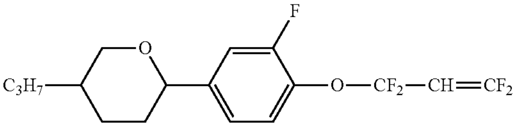

1-1-12

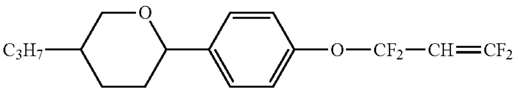

1-1-13

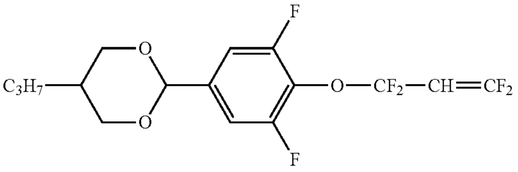

1-1-14

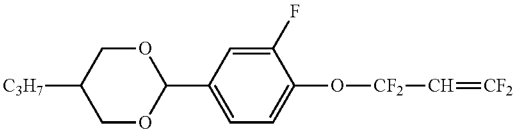

-continued
1-1-15
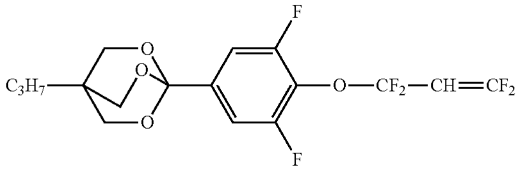
1-1-16
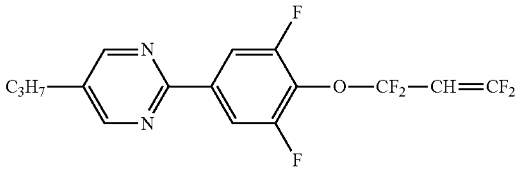
1-1-17
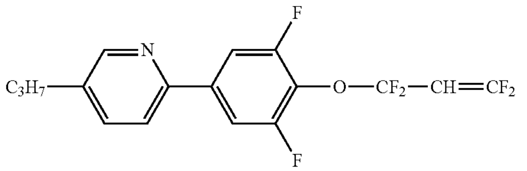
1-1-18
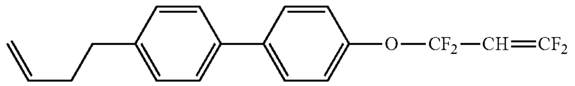
1-1-19
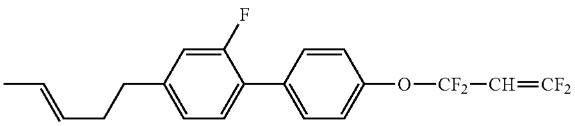
1-1-20
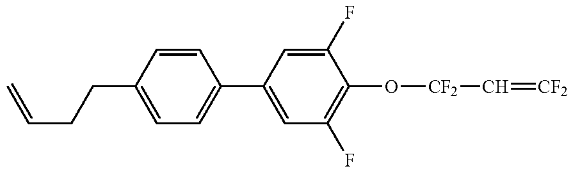
1-1-21
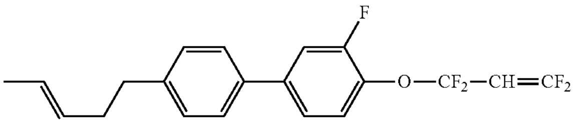
1-1-22
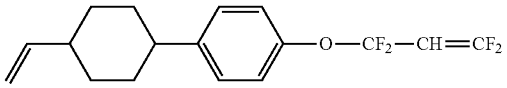
1-1-23
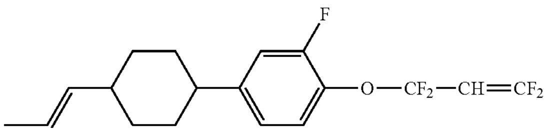
1-1-24
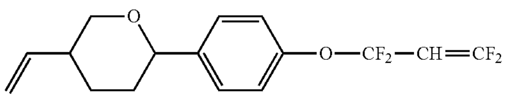
-continued
1-1-25
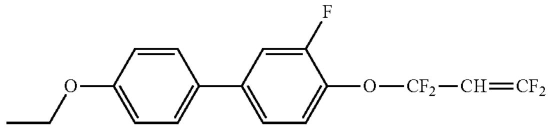
1-1-26
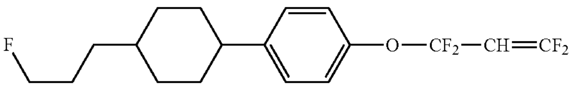
1-1-27
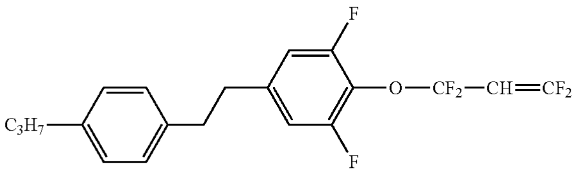
1-1-28
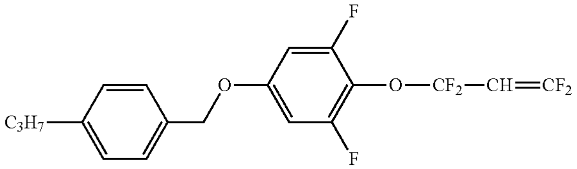
1-1-29
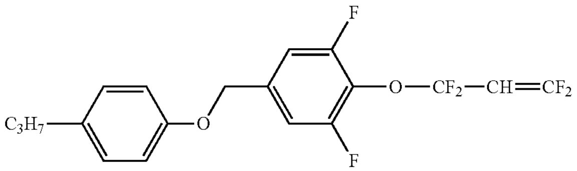
1-1-30
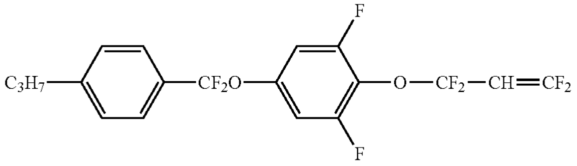
1-1-31
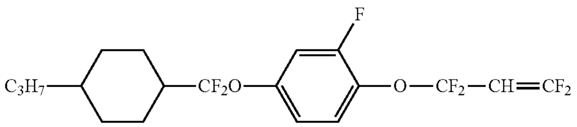
1-1-32
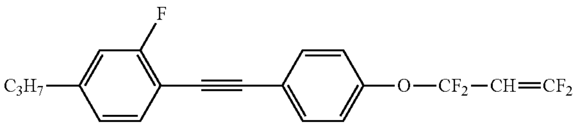
1-2-1
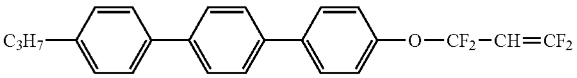
1-2-2
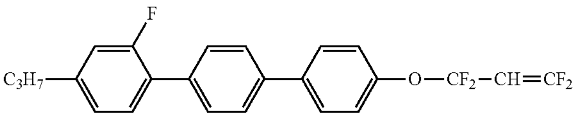

-continued
1-2-3
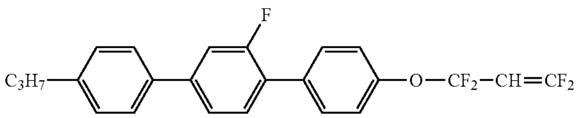
1-2-4
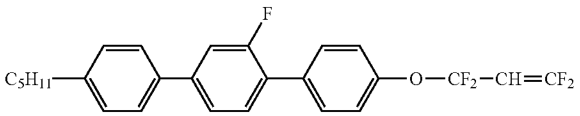
1-2-5
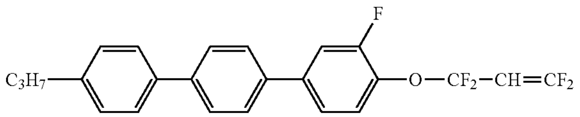
1-2-6
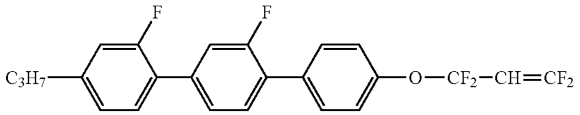
1-2-7
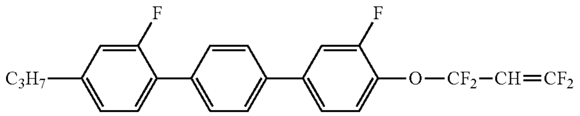
1-2-8
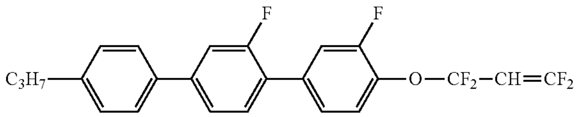
1-2-9
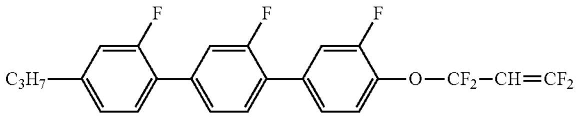
1-2-10
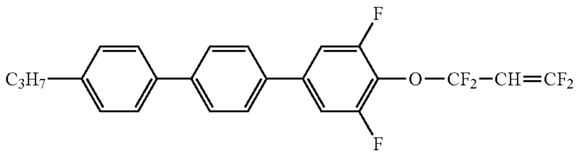
1-2-11
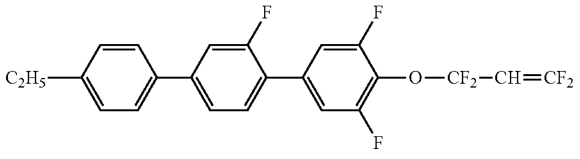
1-2-12
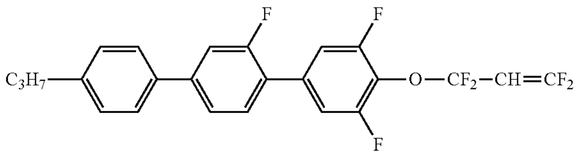
-continued
1-2-13
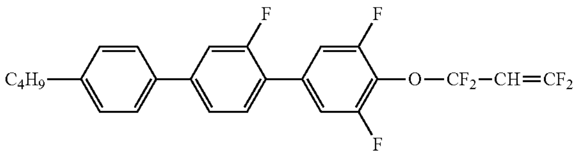
1-2-14
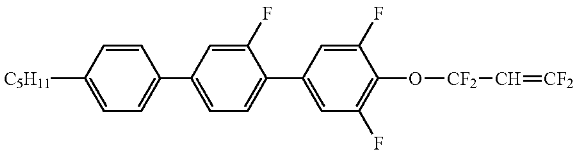
1-2-15
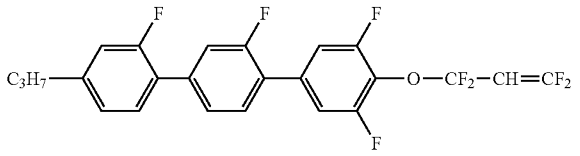
1-2-16
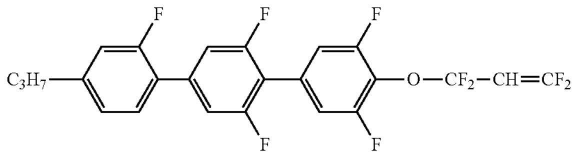
1-2-17
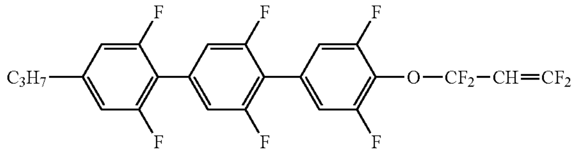
1-2-18
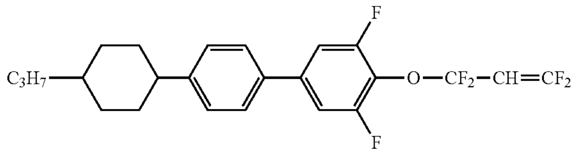
1-2-19
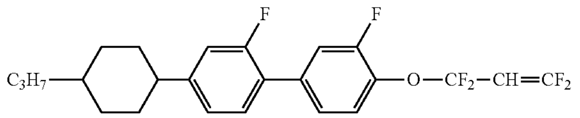
1-2-20
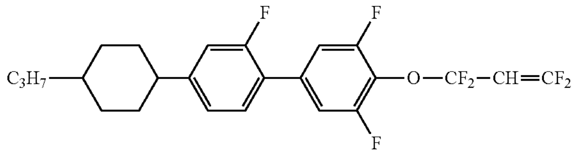
1-2-21
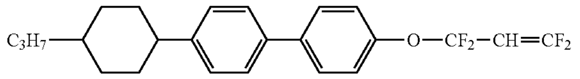

-continued
1-2-22
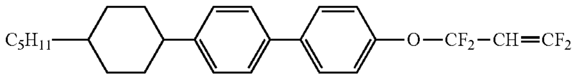
1-2-23
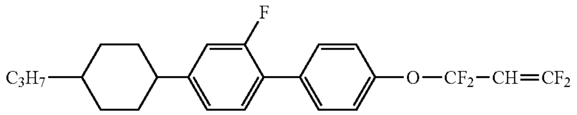
1-2-24
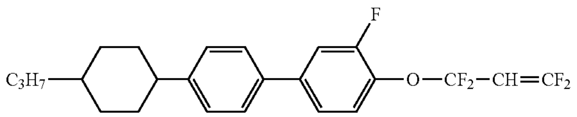
1-2-25
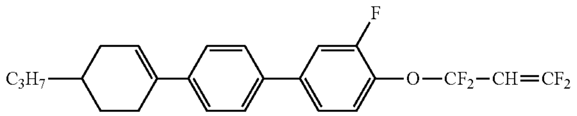
1-2-26
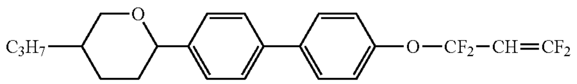
1-2-27
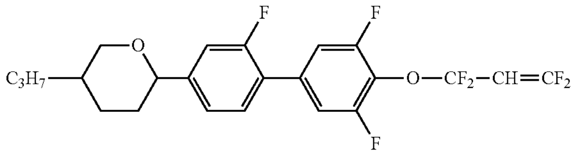
1-2-28
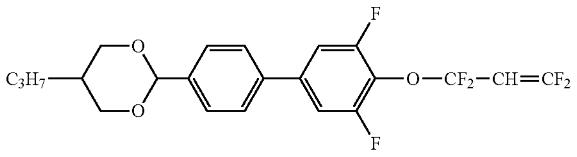
1-2-29
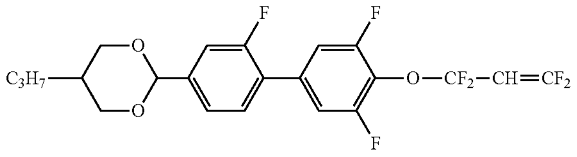
1-2-30
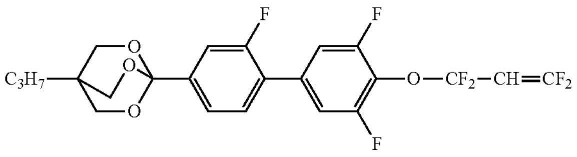
1-2-31
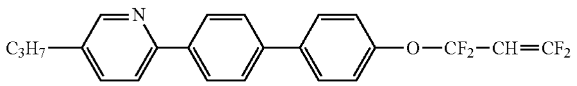
-continued
1-2-32
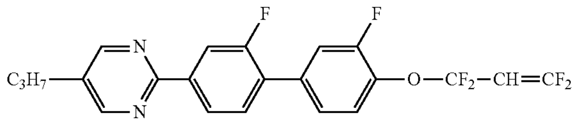
1-2-33
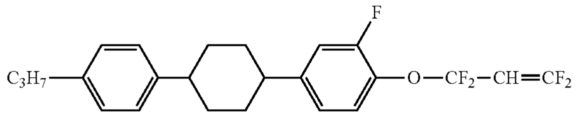
1-2-34
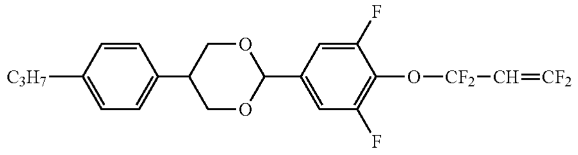
1-2-35
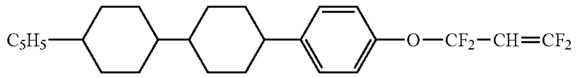
1-2-36
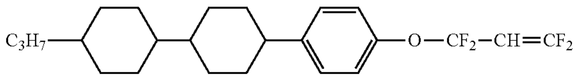
1-2-37
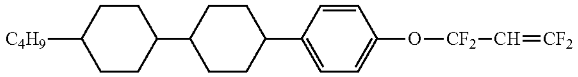
1-2-38
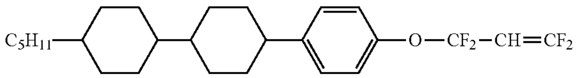
1-2-39
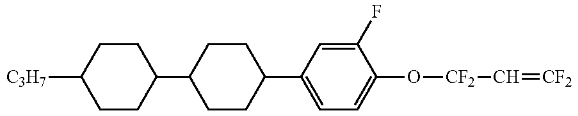
1-2-40
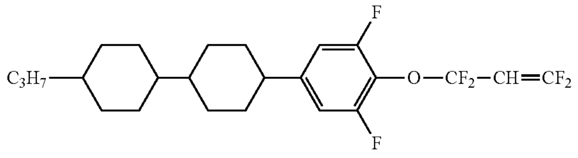
1-2-41
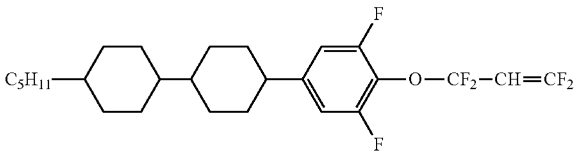
1-2-42
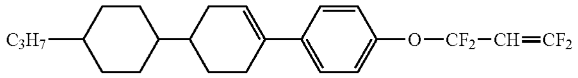

1-2-43
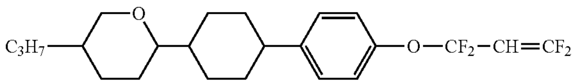
1-2-44
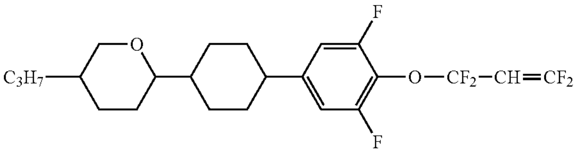
1-2-45
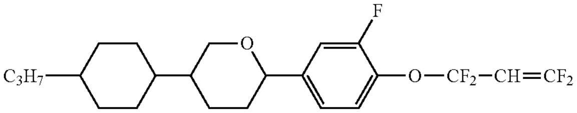
1-2-46
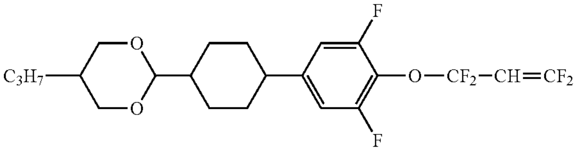
1-2-47
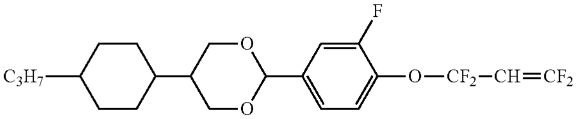
1-2-48
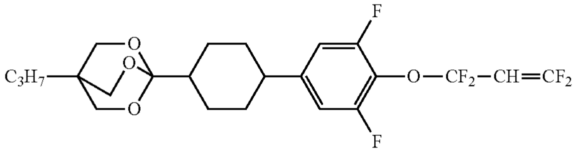
1-2-49
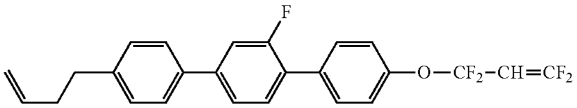
1-2-50
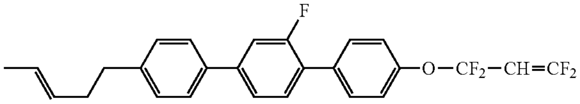
1-2-51
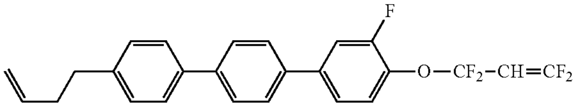
1-2-52
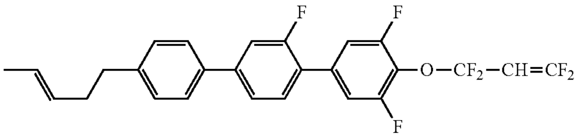
1-2-53
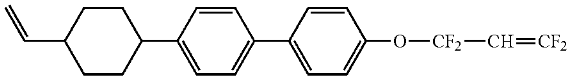
1-2-54
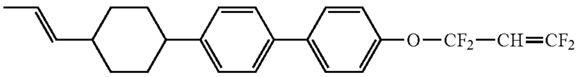
1-2-55
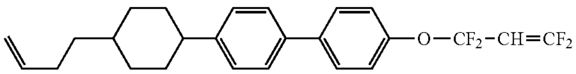
1-2-56
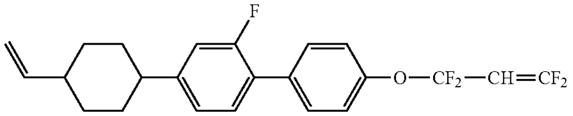
1-2-57
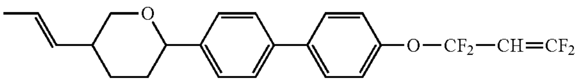
1-2-58
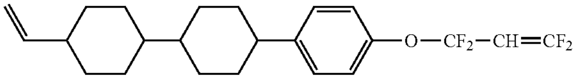
1-2-59
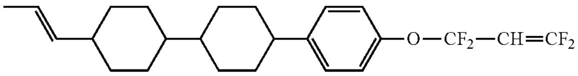
1-2-60
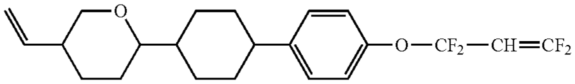
1-2-61
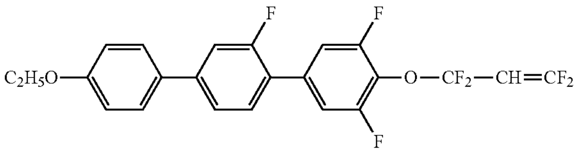
1-2-62
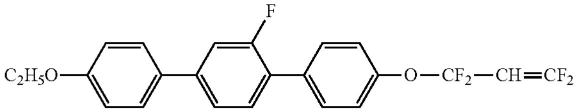
1-2-63
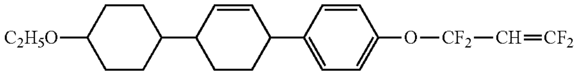
1-2-64
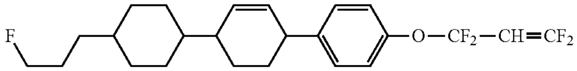

-continued
1-2-65
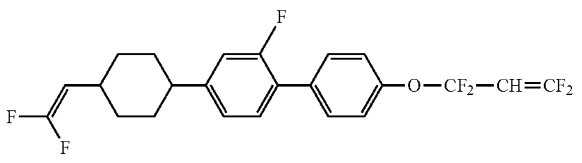
1-2-66
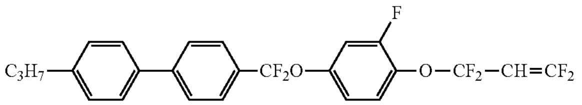
1-2-67
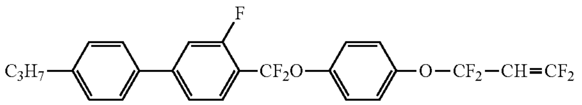
1-2-68
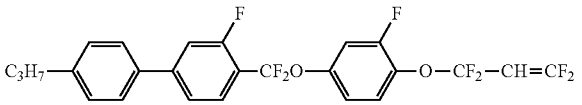
1-2-69
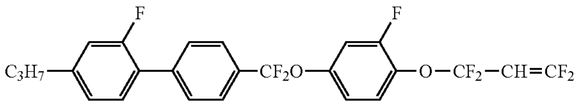
1-2-70
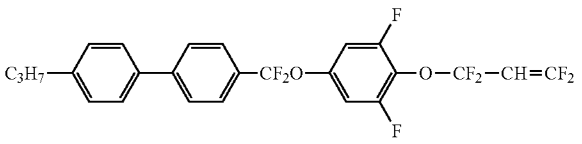
1-2-71
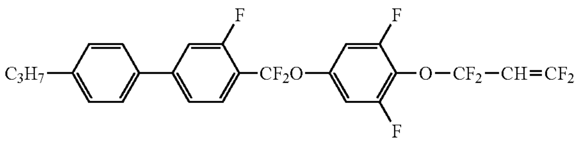
1-2-72
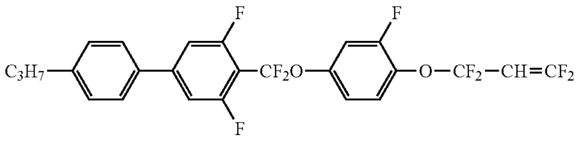
1-2-73
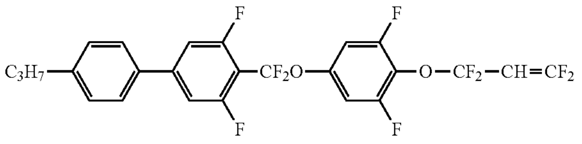
1-2-74
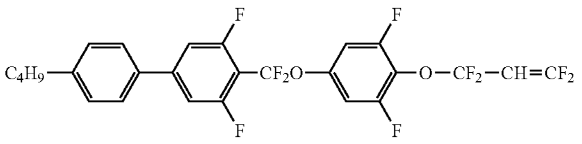
-continued
1-2-75
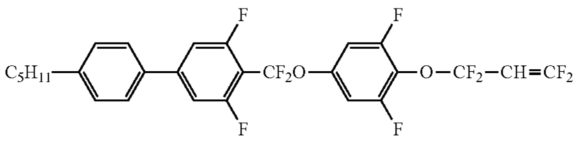
1-2-76
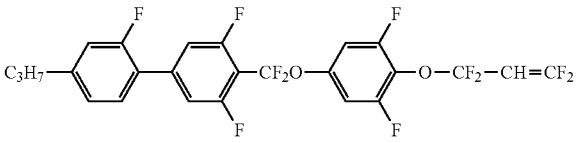
1-2-77
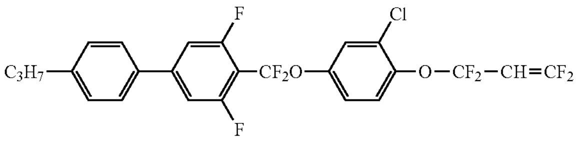
1-2-78
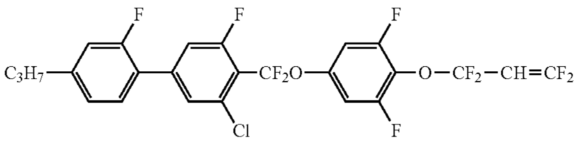
1-2-79
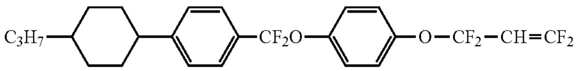
1-2-80
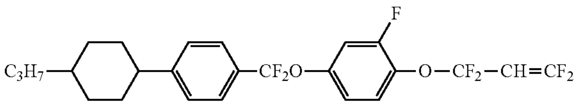
1-2-81
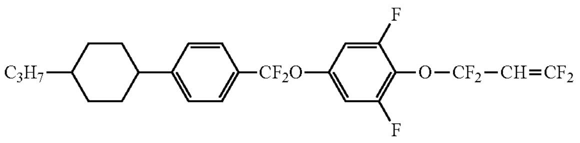
1-2-82
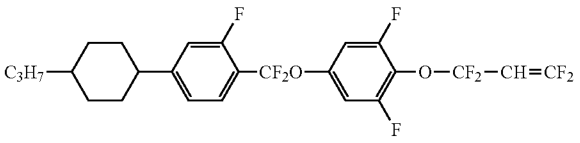
1-2-83
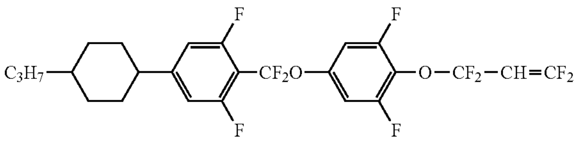
1-2-84
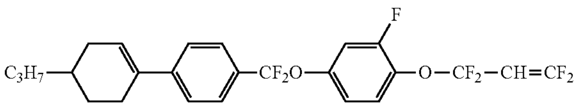

-continued
1-2-85
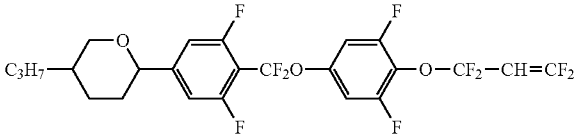
1-2-86
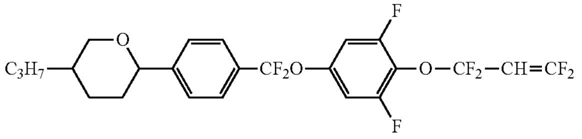
1-2-87
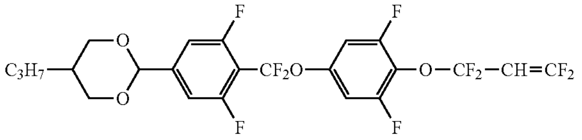
1-2-88
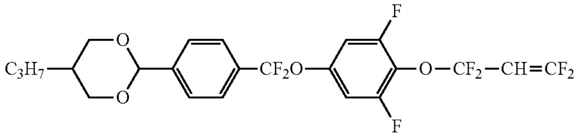
1-2-89
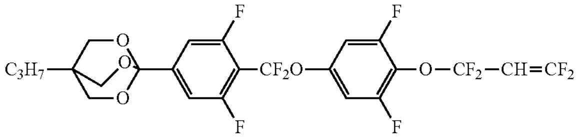
1-2-90
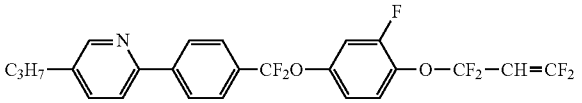
1-2-91
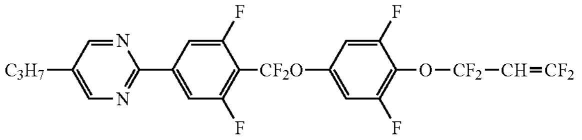
1-2-92
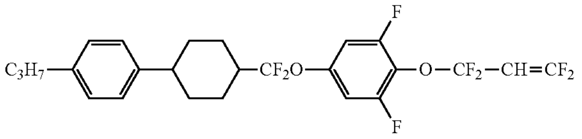
1-2-93
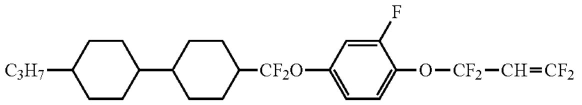
1-2-94
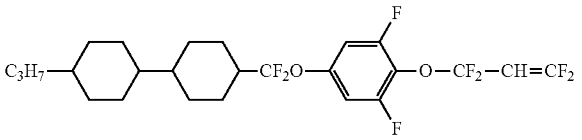
-continued
1-2-95
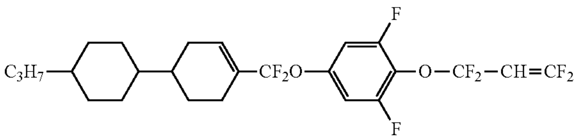
1-2-96
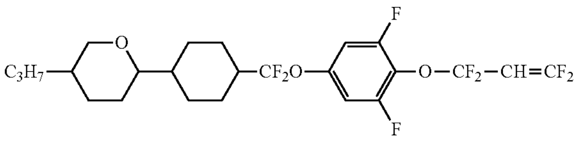
1-2-97
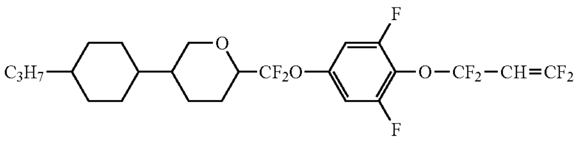
1-2-98
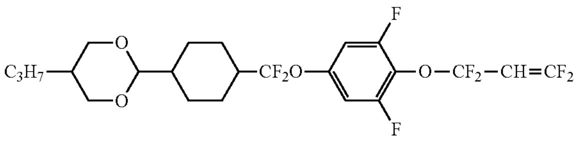
1-2-99
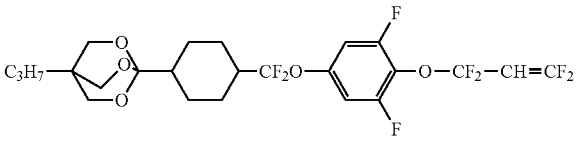
1-2-100
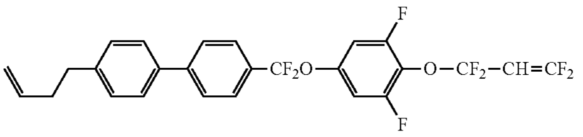
1-2-101
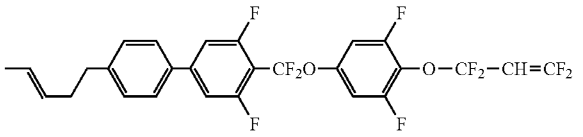
1-2-102
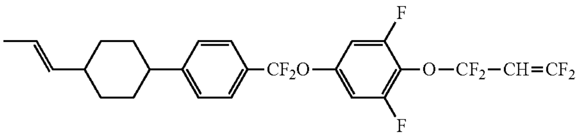
1-2-103
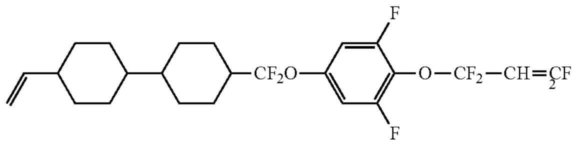

-continued
1-2-104
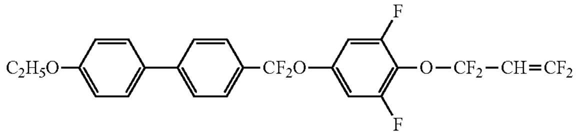
1-2-105
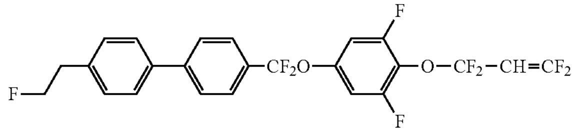
1-2-106
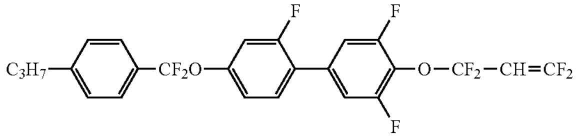
1-2-107
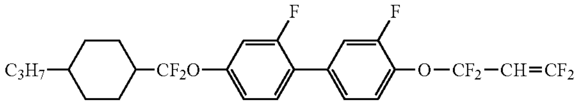
1-2-108
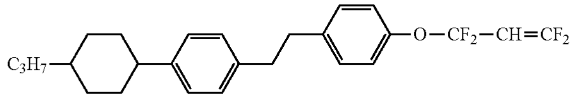
1-2-109
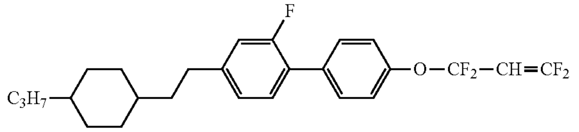
1-2-110
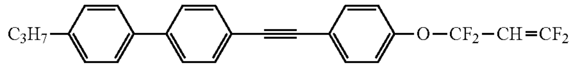
1-2-111
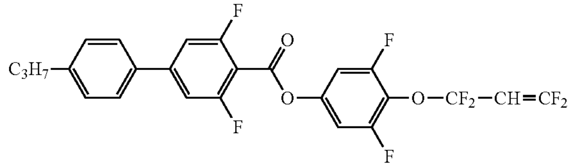
1-2-112
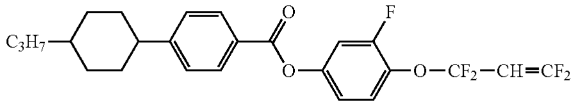
1-2-113
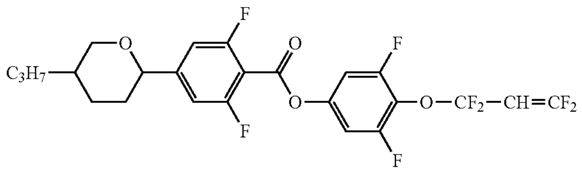
-continued
1-2-114
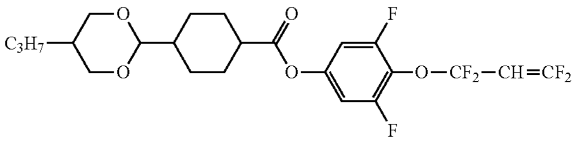
1-2-115
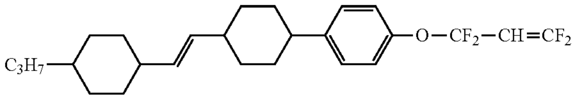
1-2-116
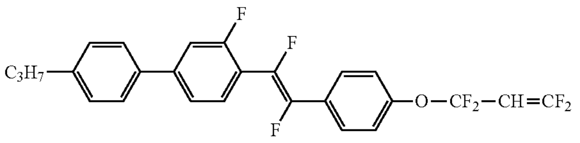
1-2-117
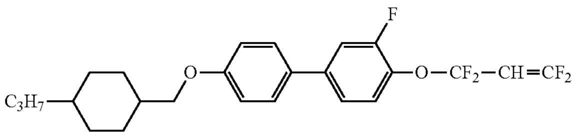
1-2-118
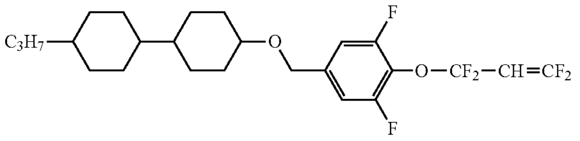
1-2-119
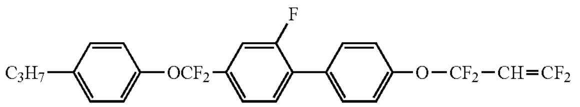
1-2-120
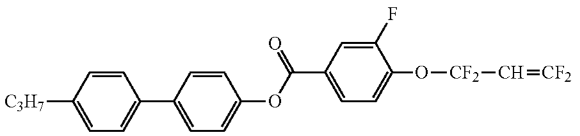
1-3-1
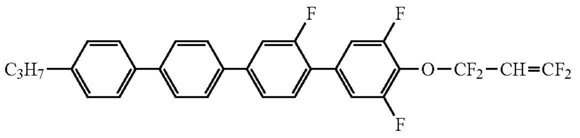
1-3-2
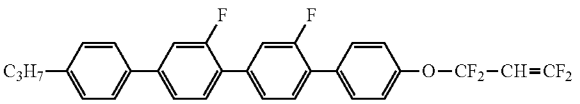
1-3-3
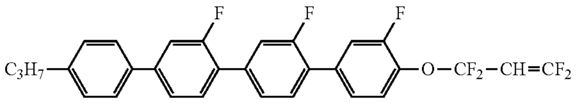

-continued
1-3-4
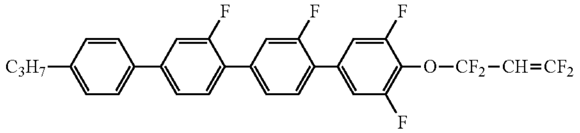
1-3-5
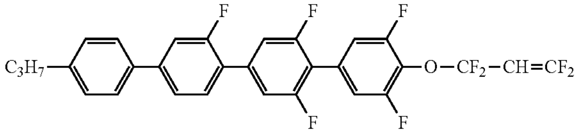
1-3-6
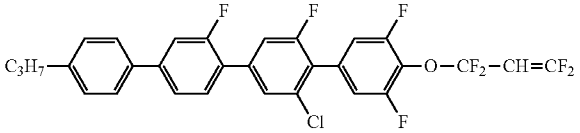
1-3-7
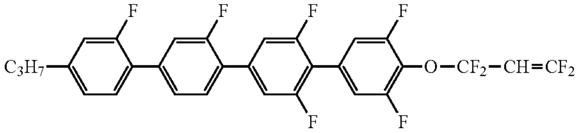
1-3-8
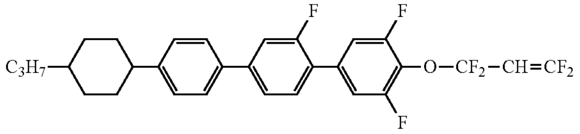
1-3-9
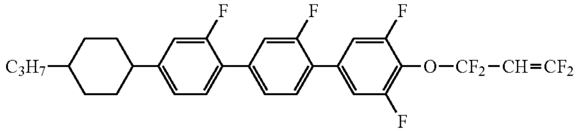
1-3-10
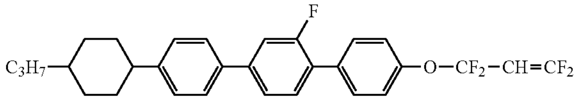
1-3-11
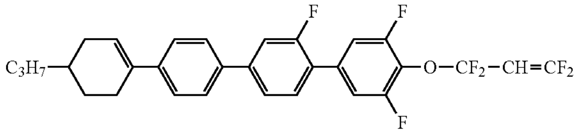
1-3-12
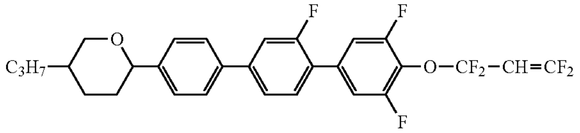
1-3-13
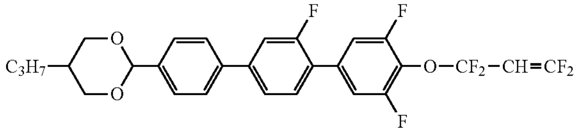
-continued
1-3-14
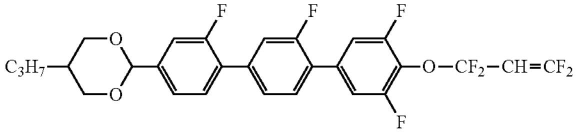
1-3-15
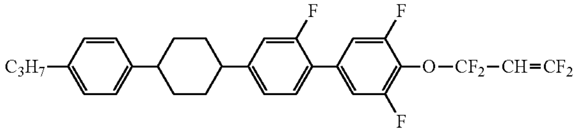
1-3-16
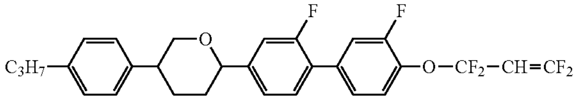
1-3-17
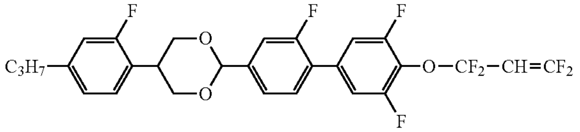
1-3-18
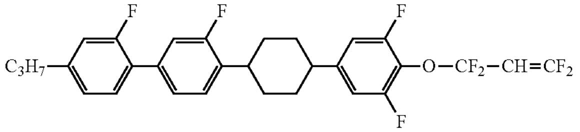
1-3-19
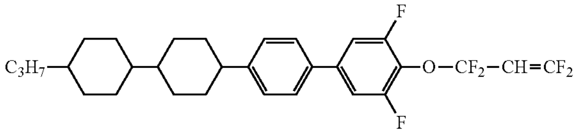
1-3-20
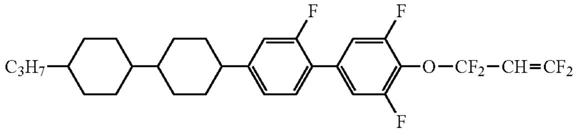
1-3-21
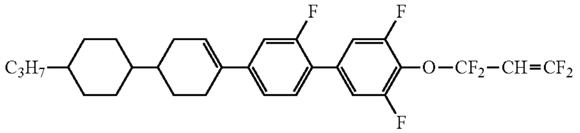
1-3-22
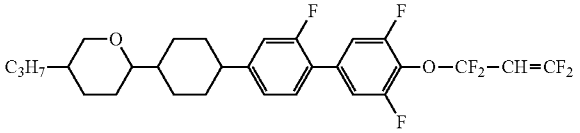
1-3-23
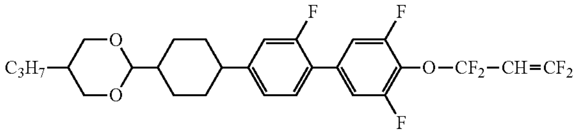

-continued
1-3-24
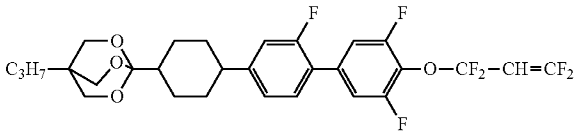
1-3-25
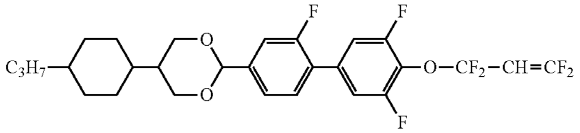
1-3-26
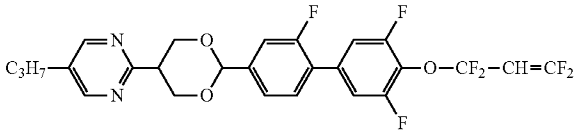
1-3-27
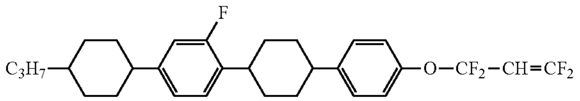
1-3-28
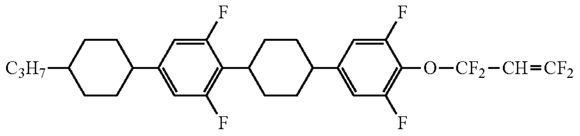
1-3-29
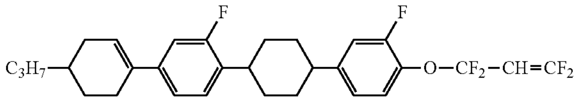
1-3-30
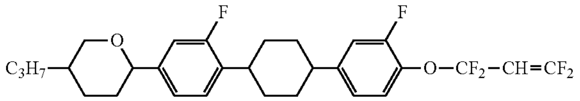
1-3-31
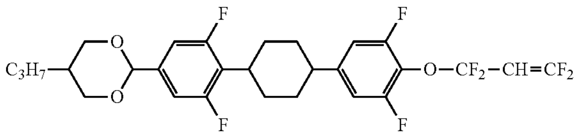
1-3-32
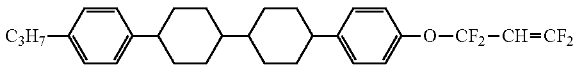
1-3-33
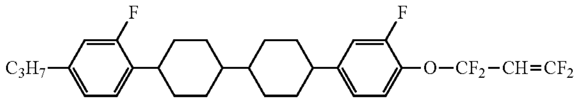
1-3-34
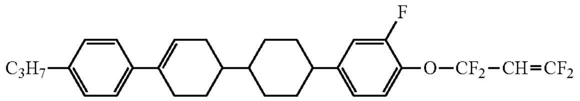
-continued
1-3-35
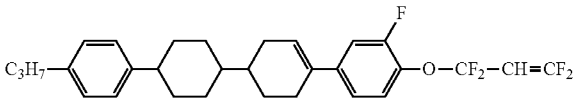
1-3-36
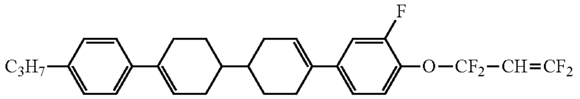
1-3-37
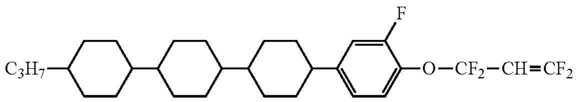
1-3-38
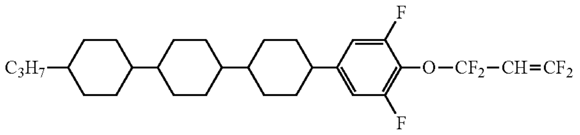
1-3-39
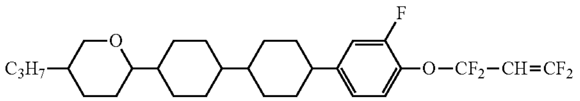
1-3-40
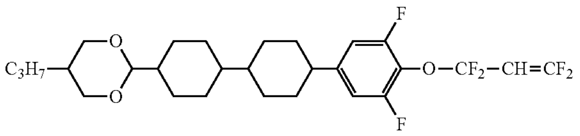
1-3-41
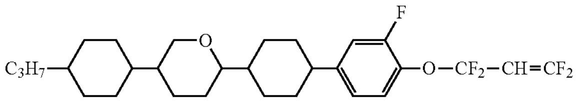
1-3-42
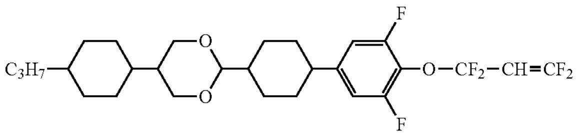
1-3-43
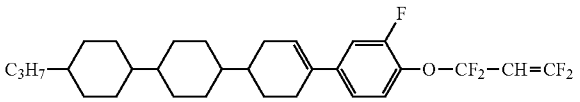
1-3-44
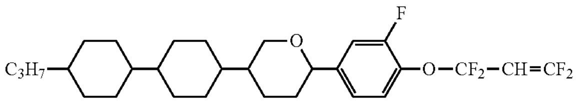
1-3-45
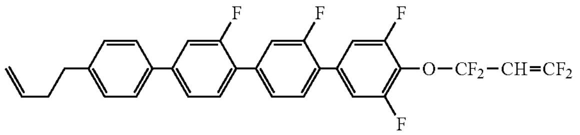

-continued
1-3-46
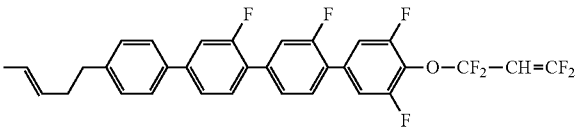
1-3-47
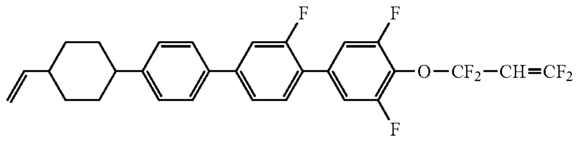
1-3-48
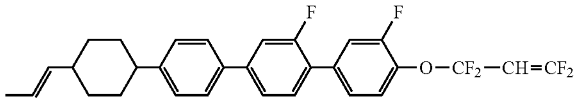
1-3-49
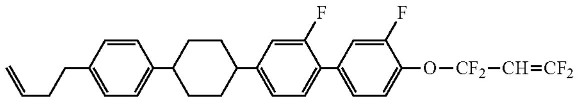
1-3-50
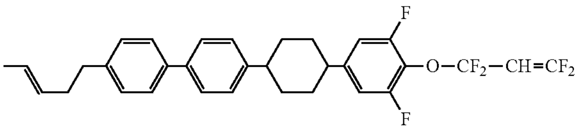
1-3-51
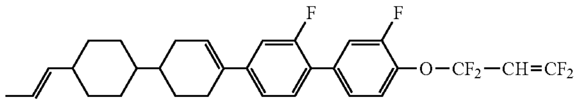
1-3-52
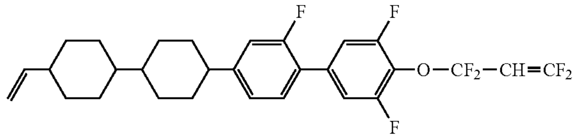
1-3-53
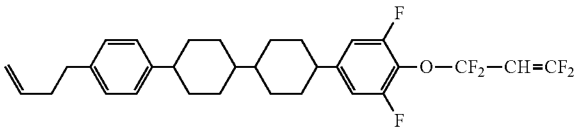
1-3-54
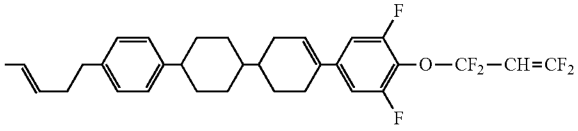
1-3-55
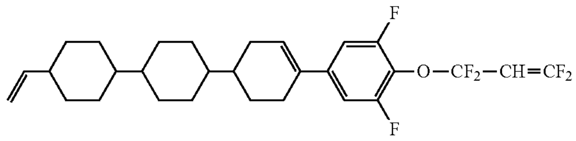
-continued
1-3-56
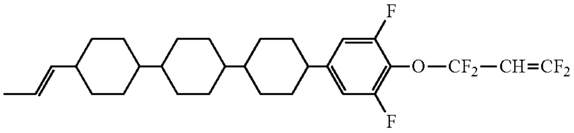
1-3-57
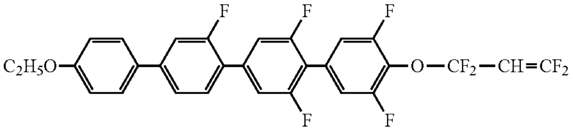
1-3-58
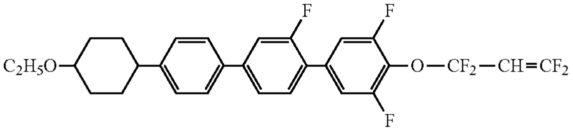
1-3-59
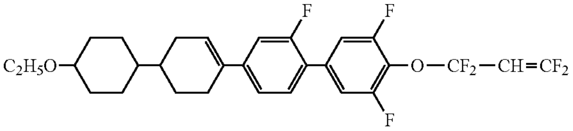
1-3-60
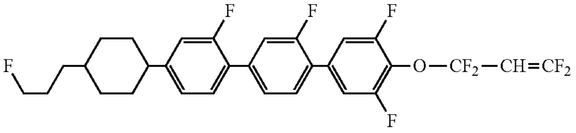
1-3-61
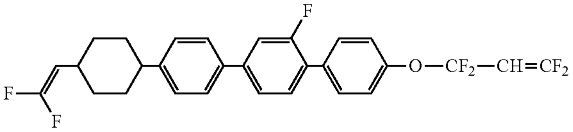
1-3-62
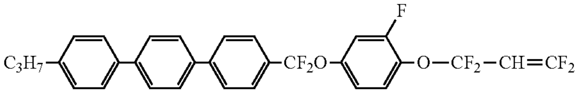
1-3-63
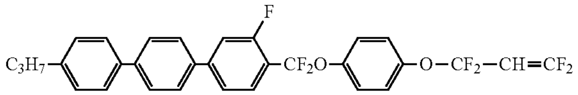
1-3-64
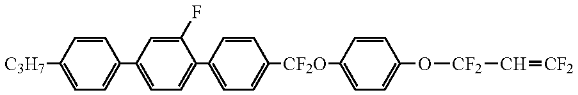
1-3-65
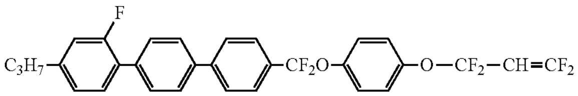
1-3-66
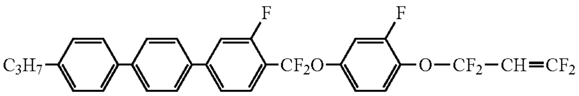

-continued
1-3-67
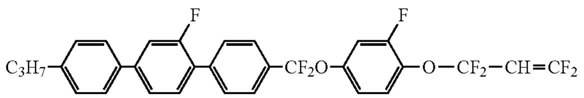
1-3-68
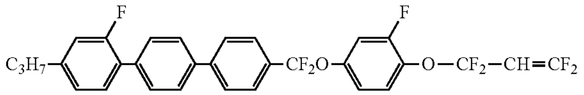
1-3-69
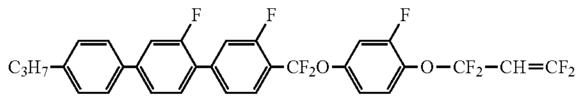
1-3-70
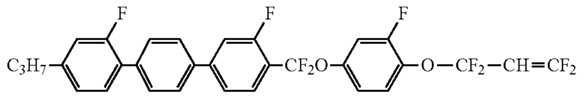
1-3-71
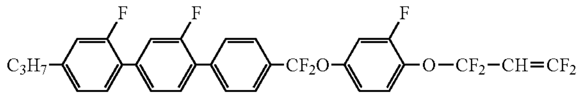
1-3-72
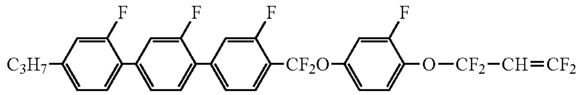
1-3-73
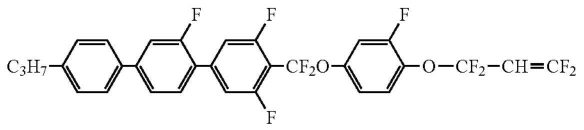
1-3-74
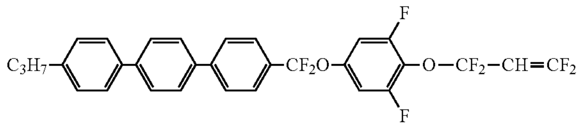
1-3-75
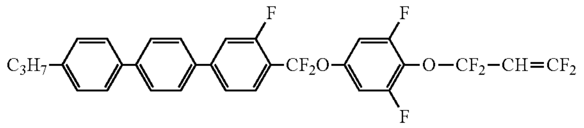
1-3-76
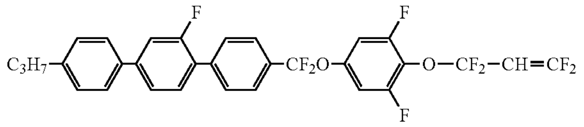
1-3-77
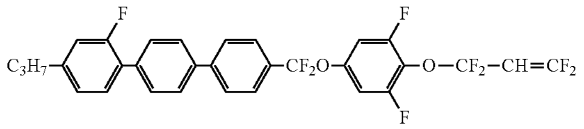
-continued
1-3-78
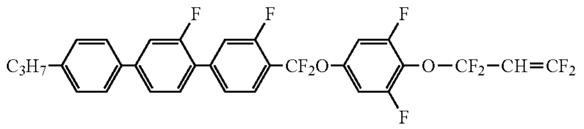
1-3-79
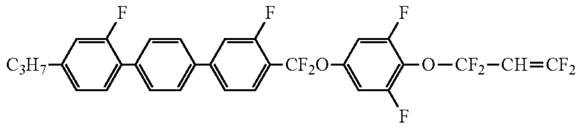
1-3-80
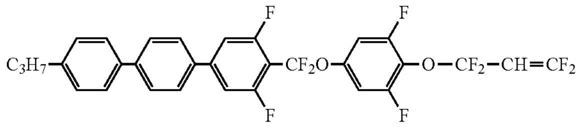
1-3-81
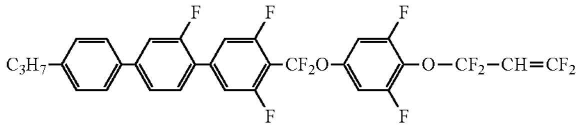
1-3-82
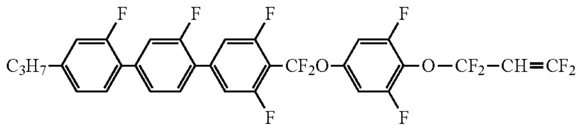
1-3-83
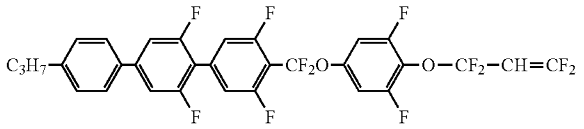
1-3-84
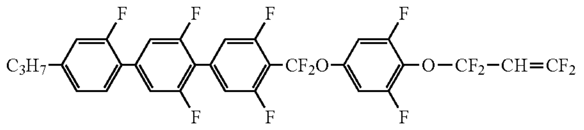
1-3-85
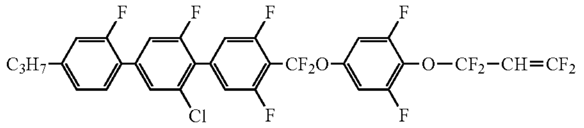
1-3-86
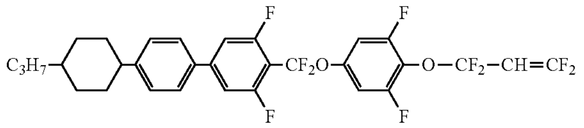
1-3-87
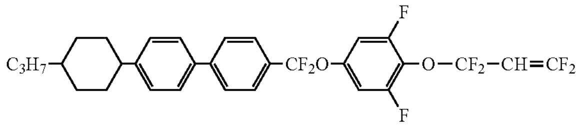

-continued
1-3-88
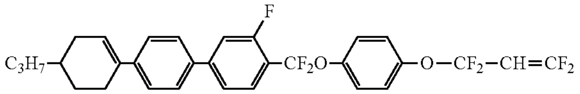
1-3-89
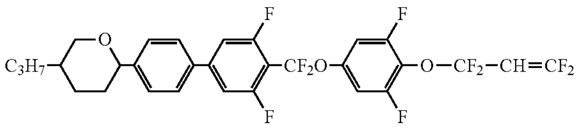
1-3-90
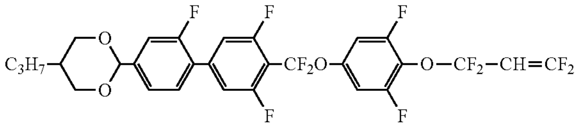
1-3-91
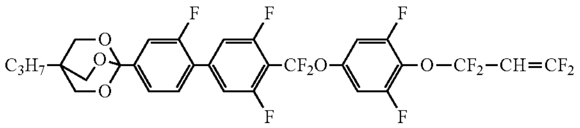
1-3-92
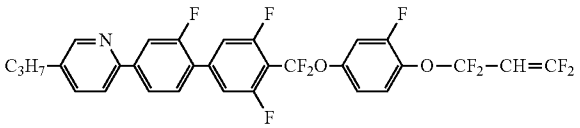
1-3-93
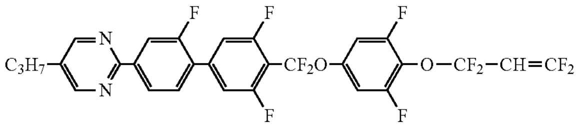
1-3-94
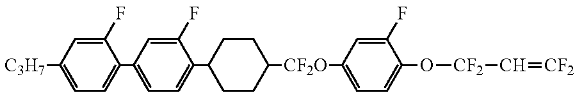
1-3-95
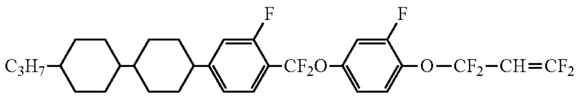
1-3-96
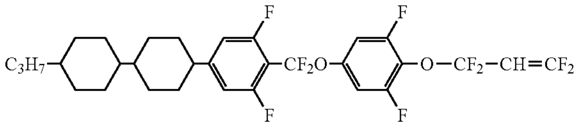
1-3-97
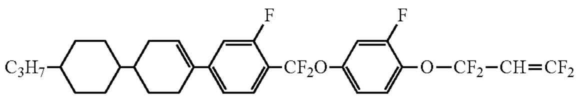
1-3-98
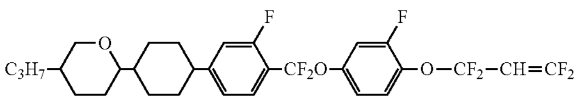
-continued
1-3-99
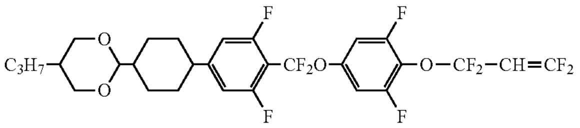
1-3-100
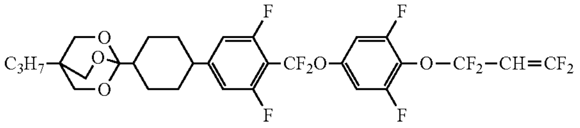
1-3-101
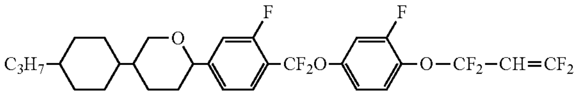
1-3-102
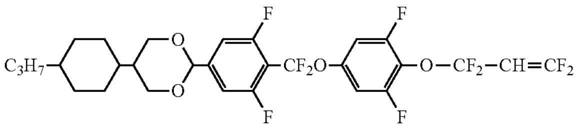
1-3-103
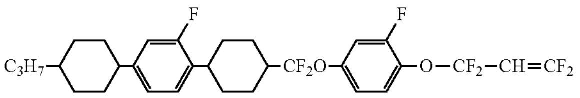
1-3-104
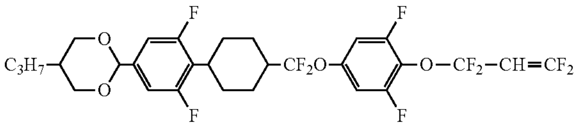
1-3-105
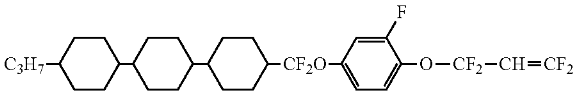
1-3-106
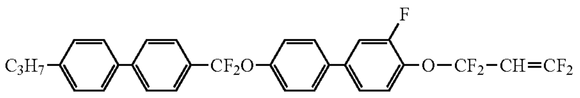
1-3-107
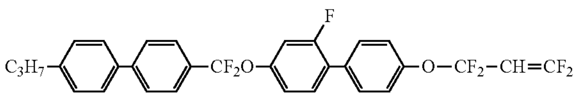
1-3-108
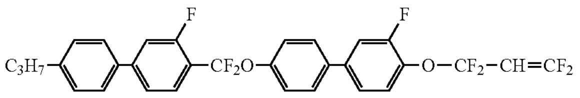
1-3-109
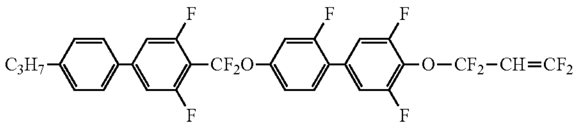

-continued
1-3-110
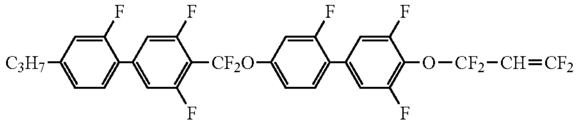
1-3-111
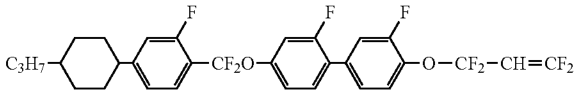
1-3-112
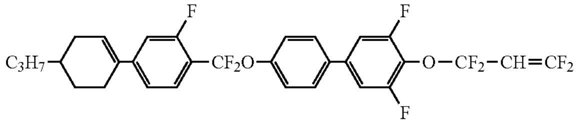
1-3-113
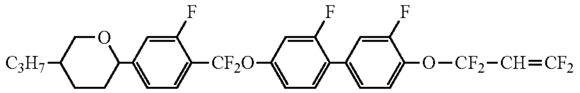
1-3-114
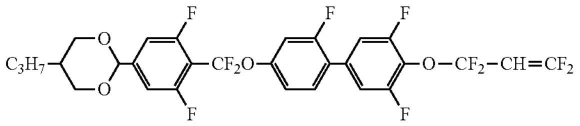
1-3-115
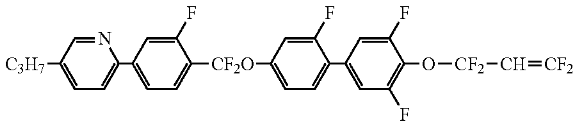
1-3-116
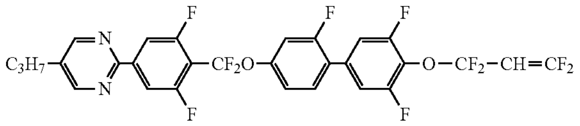
1-3-117
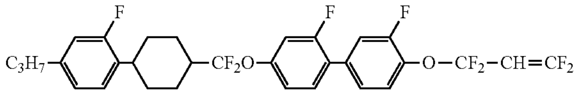
1-3-118
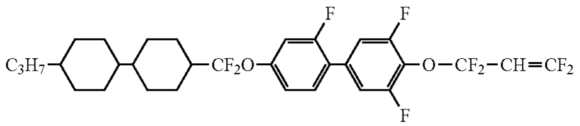
1-3-119
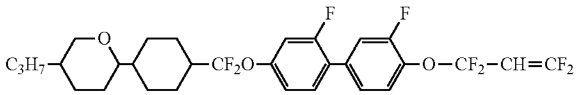
1-3-120
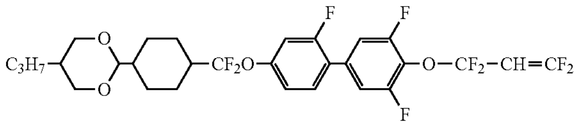
-continued
1-3-121
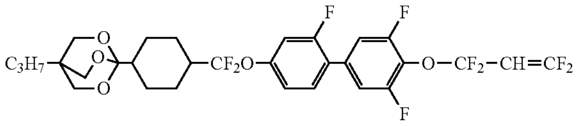
1-3-122
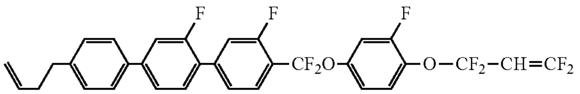
1-3-123
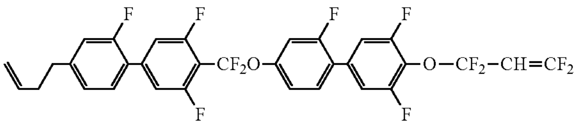
1-3-124
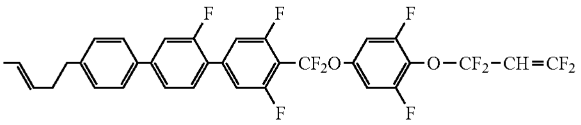
1-3-125
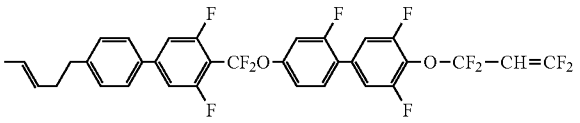
1-3-126
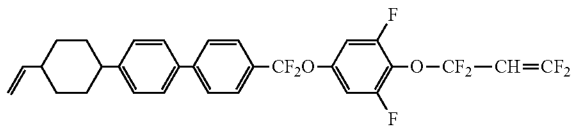
1-3-127
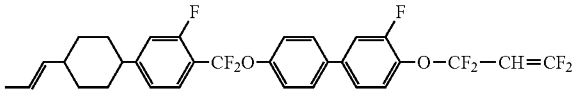
1-3-128
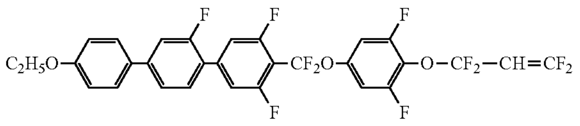
1-3-129
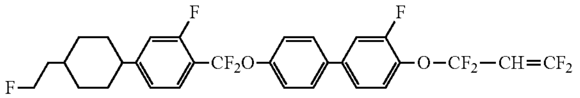
1-3-130
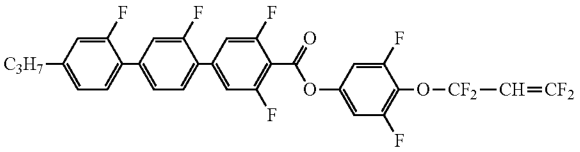

-continued
1-3-131
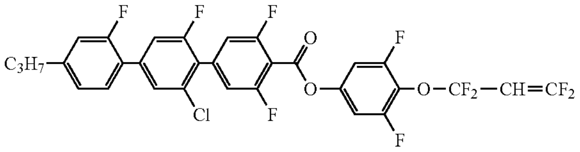
1-3-132
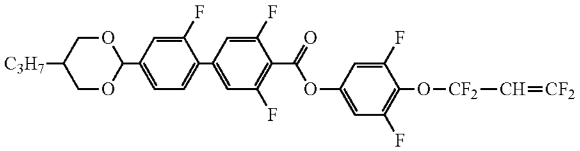
1-3-133
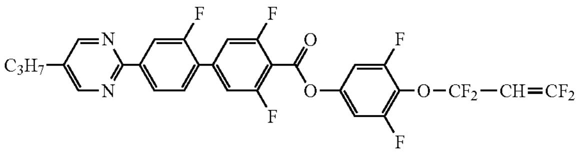
1-3-134
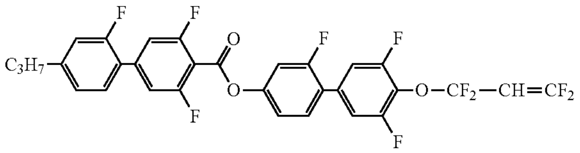
1-3-135
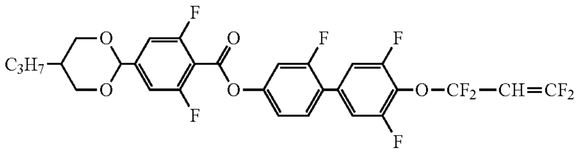
1-3-136
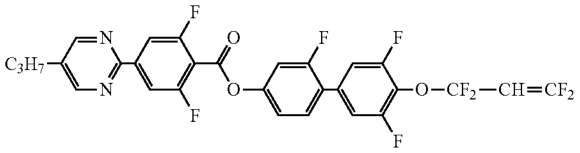
1-3-137
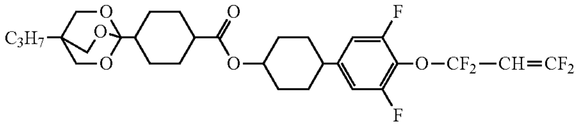
1-3-138
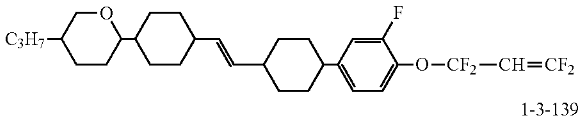
1-3-139
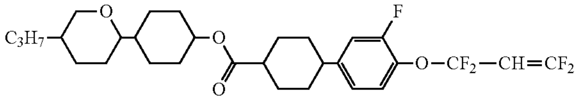
1-3-140
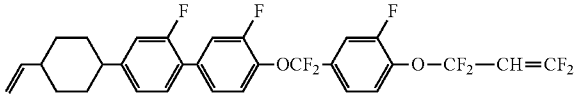
-continued
1-3-141
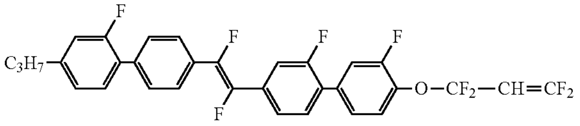
1-3-142
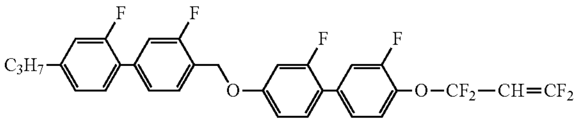
1-3-143
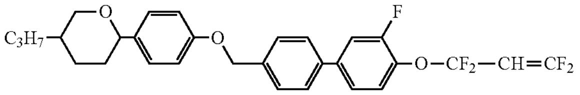
1-3-144
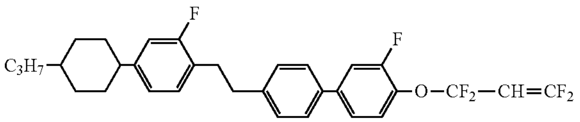
1-3-145
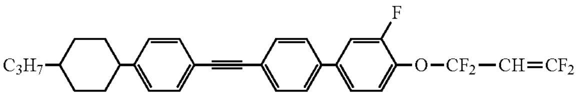
1-3-146
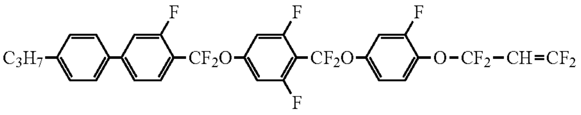
1-3-147
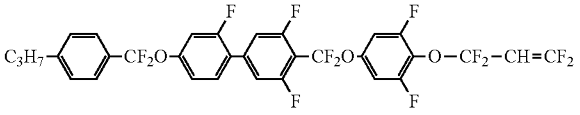
1-3-148
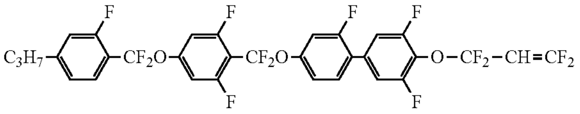
1-3-149
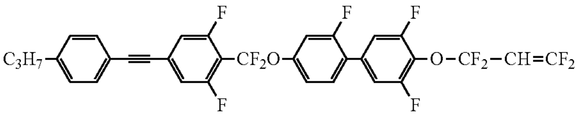
1-3-150
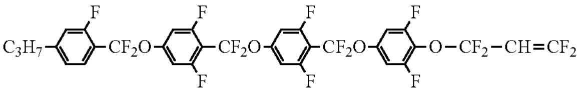
1-4-1
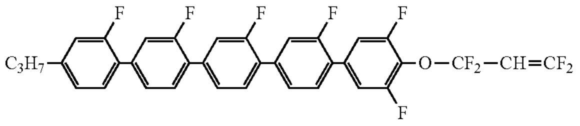

-continued
1-4-2
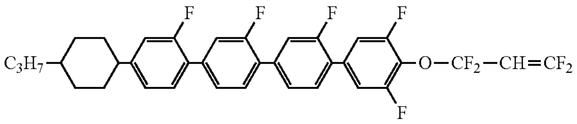
1-4-3
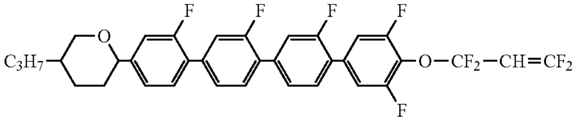
1-4-4
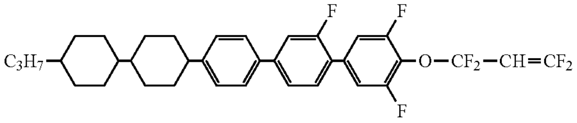
1-4-5
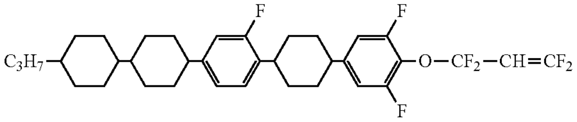
1-4-6
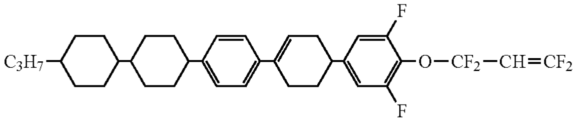
1-4-7
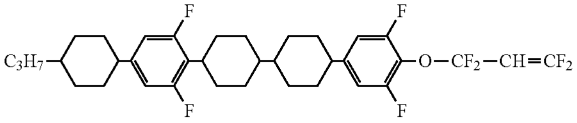
1-4-8
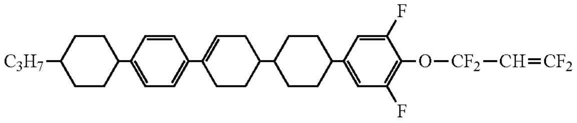
1-4-9
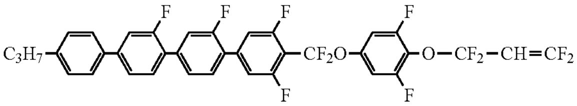
1-4-10
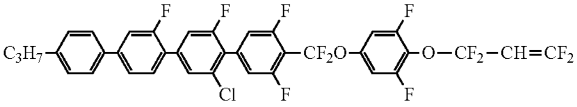
-continued
1-4-11
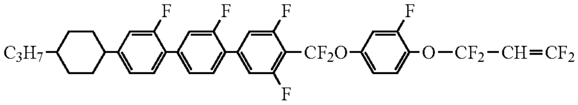
1-4-12
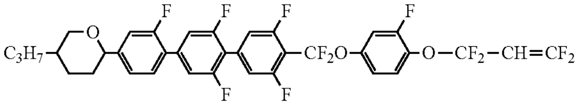
1-4-13
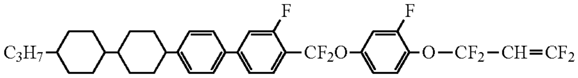
1-4-14
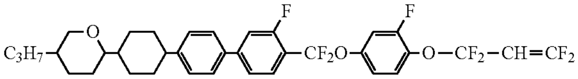
1-4-15
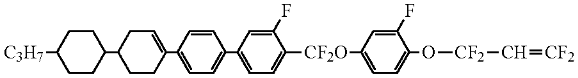
1-4-16
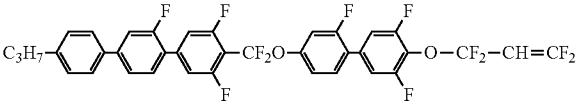
1-4-17
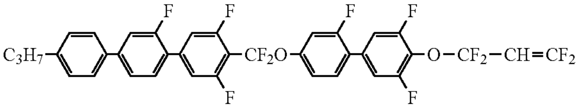
1-4-18
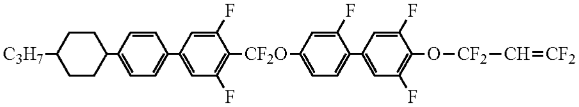
1-4-19
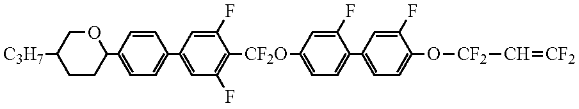
1-4-20
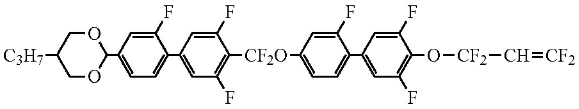
1-4-21
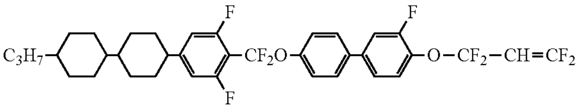

-continued 1-4-22

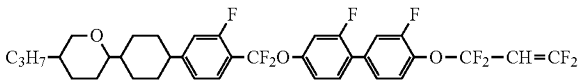

1-4-23

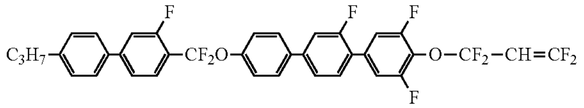

1-4-24

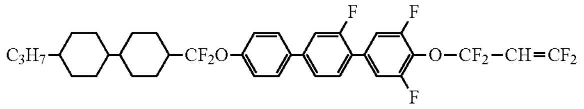

1-4-25

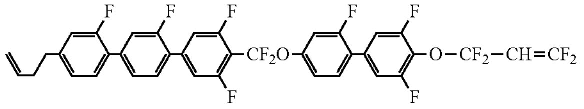

1-4-26

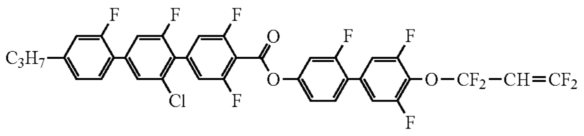

1-4-27

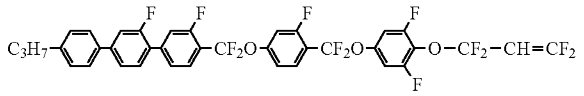

1-4-28

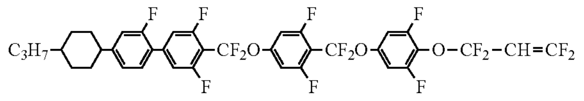

1-4-29

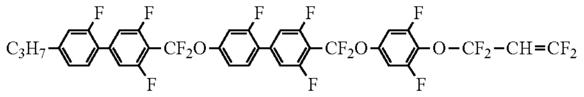

1-4-30

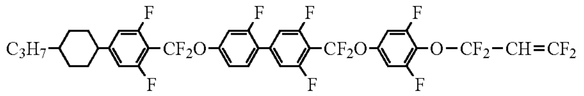

1-4-31

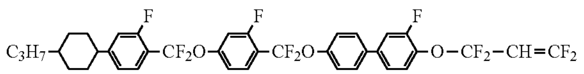

1-4-32

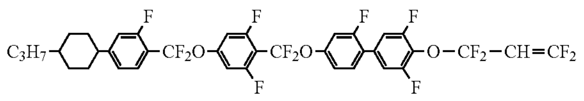

Comparative Example 1

Compound (S-1) was prepared as a comparative compound. The compound is described in JP 2007-277127 A, and has a perfluoroallyloxy group in which hydrogen is replaced by fluorine in a compound of the invention.

(S-1)

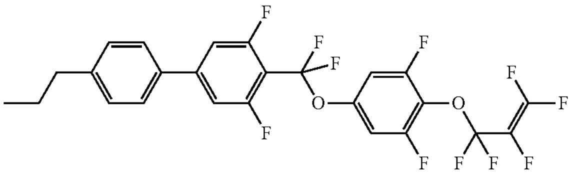

$^1$H-NMR ($CDCl_3$) δ 7.50-7.48 (m, 2H), 7.30-7.28 (m, 2H), 7.23-7.21 (m, 2H), 7.03-7.00 (m, 2H), 2.66-2.63 (m, 2H), 1.72-1.65 (sex, 2H), 0.99-0.96 (t, 3H).

Physical properties of compound (S-1) were as described below. Phase transition temperature: C 45.8 N 46.8 I. Maximum temperature (NI)=38.4° C.; dielectric anisotropy (Δε)=22.8; optical anisotropy (Δn)=0.130; viscosity (η)=33.5 mPa·s.

After making comparison of characteristics between the compound of Example 1 and compound (S-1) of Comparative Example 1, base liquid crystal (ii) described below was used. Proportions of components in base liquid crystal (ii) were expressed in terms of % by weight.

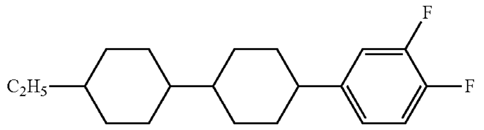

16.67%

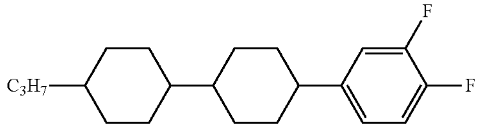

16.67%

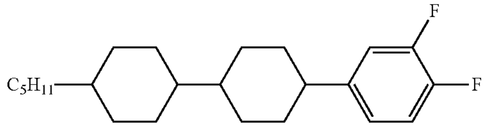

16.67%

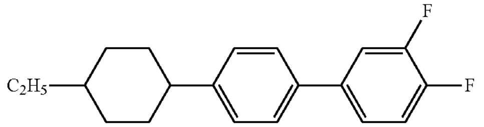

6.25%

-continued

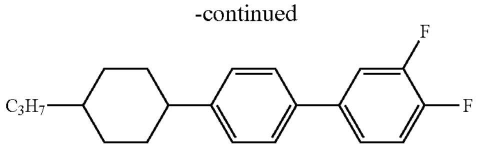

6.25%

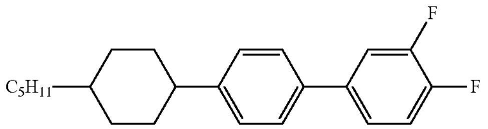

12.50%

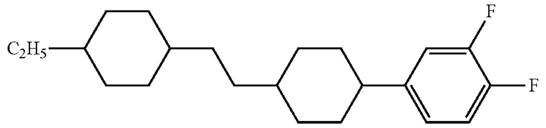

12.50%

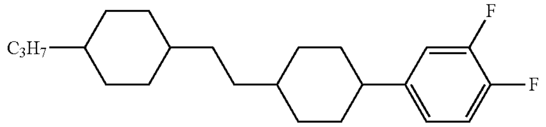

6.25%

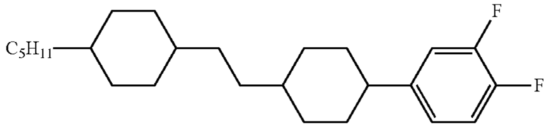

6.25%

TABLE 1

| Physical properties of compound (No. 1-2-73) and comparative compound (S-1) | | |
|---|---|---|
| | Compound (No. 1-2-73) | Comparative compound (S-1) |
| | 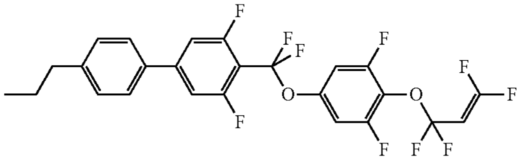 | 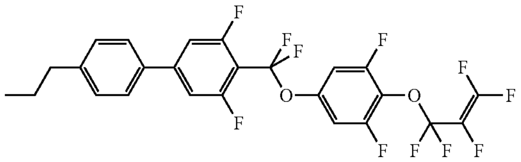 |
| Voltage holding ratio (VHR-2) | 97.23 | 88.72 |
| Compatibility at a low temperature (−20° C.) | 20 | 5 |

Physical properties of compound (No. 1-2-73) of Example 1 and comparative compound (S-1) are summarized in Table 1. Values of compatibility at a low temperature in the table represents that no crystal or smectic phase was precipitated, even after the compound was mixed with the base liquid crystal in the % by weight and the resulting mixture was left in a freezer at −20° C. for a predetermined period of time. Compound (No. 1-2-73) has higher voltage holding ratio (VHR-2) in comparison with comparative compound (S-1). Therefore, compound (No. 1-2-73) is a better compound that is more stable to heat. Moreover, compound (No. 1-2-73) has better compatibility at a low temperature at −20° C. in comparison with comparative compound (S-1). Accordingly, compound (No. 1-2-73) is a better compound that can be used in the wider range of temperature.

1-2. Example of Composition (1)

Liquid crystal composition (1) of the invention will be described in detail by way of Examples. The compounds in Examples were represented using symbols according to definitions in Table 2 described below. In Table 2, a configuration of 1,4-cyclohexylene is trans. In Examples, a parenthesized number next to a symbolized compound corresponds to the number of the compound. A symbol (-) means any other liquid crystal compound. A proportion (percentage) of the liquid crystal compound is expressed in terms of weight percent (% by weight) based on the weight of the liquid crystal composition. Values of the physical properties of the composition are summarized in a last part. The physical properties were measured according to the methods described above, and measured values are directly described (without extrapolation).

TABLE 2

| Method for Description of Compounds using Symbols $R—(A_1)—Z_1— \ldots —Z_n—(A_n)—R'$ | Symbol |
|---|---|
| 1) Left-terminal Group R• | |
| $C_nH_{2n+1}—$ | n- |
| $C_nH_{2n+1}O—$ | nO— |
| $C_mH_{2m+1}OC_nH_{2n}—$ | mOn- |
| $CH_2{=}CH—$ | V— |
| $C_nH_{2n+1}—CH{=}CH—$ | nV— |

TABLE 2-continued

| Method for Description of Compounds using Symbols $R—(A_1)—Z_1— \ldots —Z_n—(A_n)—R'$ | Symbol |
|---|---|
| $CH_2{=}CH—C_nH_{2n}—$ | Vn- |
| $C_mH_{2m+1}—CH{=}CH—C_nH_{2n}—$ | mVn- |
| $CF_2{=}CH—$ | VFF— |
| $CF_2{=}CH—C_nH_{2n}—$ | VFFn- |

TABLE 2-continued

| Method for Description of Compounds using Symbols $R-(A_1)-Z_1-\ldots-Z_n-(A_n)-R'$ | Symbol |
|---|---|
| 2) Right-terminal Group —R' | |
| $-C_nH_{2n+1}$ | -n |
| $-OC_nH_{2n+1}$ | —On |
| $-COOCH_3$ | —EMe |
| $-CH{=}CH_2$ | —V |
| $-CH{=}CH-C_nH_{2n+1}$ | —Vn |
| $-C_nH_{2n}-CH{=}CH_2$ | -nV |
| $-C_mH_{2m}-CH{=}CH-C_nH_{2n+1}$ | -mVn |
| $-CH{=}CF_2$ | —VFF |
| —F | —F |
| —Cl | —CL |
| $-OCF_3$ | —OCF3 |
| $-OCF_2H$ | —OCF2H |
| $-CF_3$ | —CF3 |
| $-OCF_2-CH{=}CF_2$ | —OCF2VFF |
| $-C{\equiv}N$ | —C |
| 3) Bonding Group $-Z_n-$ | |
| $-C_nH_{2n}-$ | n |
| —COO— | E |
| —CH═CH— | V |
| $-CH_2O-$ | 1O |
| $-OCH_2-$ | O1 |
| $-CF_2O-$ | X |
| —C≡C— | T |
| 4) Ring Structure $-A_n-$ | |
| 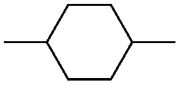 | H |
| 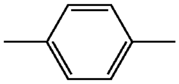 | B |
| 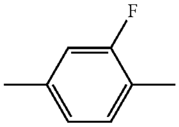 | B(F) |
| 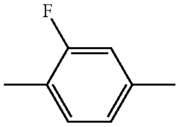 | B(2F) |
| 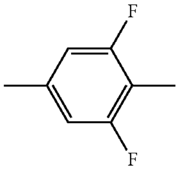 | B(F, F) |
| 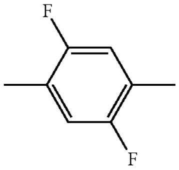 | B(2F, 5F) |

TABLE 2-continued

| Method for Description of Compounds using Symbols $R-(A_1)-Z_1-\ldots-Z_n-(A_n)-R'$ | Symbol |
|---|---|
| 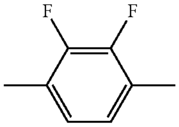 | B(2F, 3F) |
| 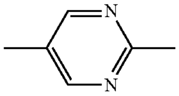 | Py |
| 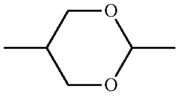 | G |
| 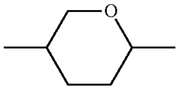 | dh |
| 5) Examples of Description | |
| Example 1 3-HB—O2 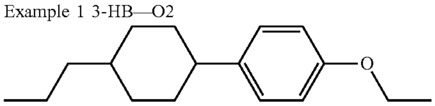 | |
| Example 2 3-BB(F, F)XB(F, F)—OCF2VFF 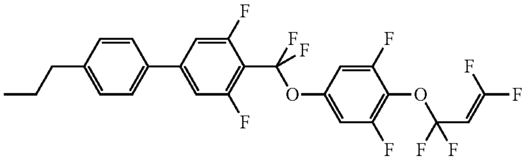 [SMILES: CCCc1ccc(-c2cc(F)c(C(F)(F)Oc3cc(F)c(OC(F)(F)C=C(F)F)c(F)c3)c(F)c2)cc1] | |
| Example 3 3-HH-4 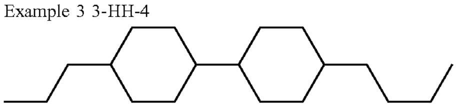 | |
| Example 4 3-HBB(F, F)—F 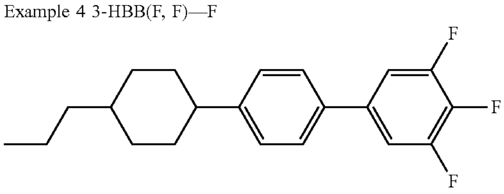 | |

Example 5

| | | |
|---|---|---|
| 3-BB(F,F)XB(F,F)-OCF2VFF | (1-2-73) | 3% |
| 3-HB-O2 | (13-5) | 10% |
| 5-HB-CL | (2-2) | 13% |
| 3-HBB(F,F)-F | (3-24) | 4% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |

-continued

| | | |
|---|---|---|
| 5-HBB(F)B-2 | (15-5) | 10% |
| 5-HBB(F)B-3 | (15-5) | 10% |

NI=99.0° C.; Δn=0.191; Δ∈=8.1; η=39.6 mPa·s.

Example 6

| | | |
|---|---|---|
| 3-HHB(F,F)-OCF2VFF | (1-2-40) | 5% |
| 2-HB-C | (5-1) | 4% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 6% |
| 3-HHB-O1 | (14-1) | 5% |
| 3-HHB-3 | (14-1) | 12% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI=100.1° C.; Δn=0.100; Δ∈=4.7; η=18.6 mPa·s.

Example 7

| | | |
|---|---|---|
| 3-HB-OCF2VFF | (1-1-9) | 4% |
| 5-HB-CL | (2-2) | 13% |
| 3-HH-4 | (13-1) | 12% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 8% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=114.3° C.; Δn=0.091; Δ∈=3.7; η=18.7 mPa·s.

Example 8

| | | |
|---|---|---|
| 3-HHB-OCF2VFF | (1-2-36) | 3% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 20% |
| 5-HBB(F,F)-F | (3-24) | 19% |
| 3-H2BB(F,F)-F | (3-27) | 9% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

NI=100.7° C.; Δn=0.116; Δ∈=8.8; η=34.3 mPa·s.

A pitch was 65.3 micrometers when 0.25 part by weight of compound (Op-05) was added to 100 parts by weight of the composition described above.

Example 9

| | | |
|---|---|---|
| 3-B(F)B(F,F)XB(F,F)-OCF2VFF | (1-2-76) | 5% |
| 5-HB-CL | (2-2) | 11% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 20% |
| 5-HBB(F,F)-F | (3-24) | 13% |
| 3-HHEB(F,F)-F | (3-12) | 10% |
| 4-HHEB(F,F)-F | (3-12) | 3% |
| 5-HHEB(F,F)-F | (3-12) | 3% |
| 3-HBEB(F,F)-F | (3-39) | 5% |
| 5-HBEB(F,F)-F | (3-39) | 3% |
| 3-HHBB(F,F)-F | (4-6) | 6% |

Example 10

| | | |
|---|---|---|
| 3-GB(F)B(F,F)-OCF2VFF | (1-2-29) | 4% |
| 3-HH-4 | (13-1) | 4% |
| 3-HBB(F,F)-F | (3-24) | 31% |
| 5-HBB(F,F)-F | (3-24) | 30% |
| 3-H2HB(F,F)-F | (3-15) | 10% |
| 4-H2HB(F,F)-F | (3-15) | 10% |
| 5-H2HB(F,F)-F | (3-15) | 8% |
| 3-HHBB(F,F)-F | (4-6) | 3% |

Example 11

| | | |
|---|---|---|
| 3-BB(F)B(F,F)-OCF2VFF | (1-2-12) | 3% |
| 5-HB-CL | (2-2) | 3% |
| 7-HB(F)-F | (2-3) | 7% |
| 3-HH-4 | (13-1) | 9% |
| 3-HH-EMe | (13-2) | 20% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Example 12

| | | |
|---|---|---|
| 3-HBB(F,F)-OCF2VFF | (1-2-18) | 5% |
| 1V2-BEB(F,F)-C | (5-15) | 6% |
| 3-HB-C | (5-1) | 17% |
| 2-BTB-1 | (13-10) | 10% |
| 5-HH-VFF | (13-1) | 28% |
| 3-HHB-1 | (14-1) | 4% |
| VFF-HHB-1 | (14-1) | 8% |
| VFF2-HHB-1 | (14-1) | 10% |
| 3-H2BTB-2 | (14-17) | 4% |
| 3-H2BTB-3 | (14-17) | 4% |
| 3-H2BTB-4 | (14-17) | 4% |

INDUSTRIAL APPLICABILITY

A liquid crystal compound of the invention satisfies at least one of physical properties such as a high stability to heat, light or the like, a high clearing point, a low minimum temperature of a liquid crystal phase, a small viscosity, a suitable optical anisotropy, a large dielectric anisotropy, a suitable elastic constant and an excellent compatibility with other liquid crystal compounds. A liquid crystal composition of the invention contains the compound and satisfies at least one of physical properties such as a high maximum temperature, a low minimum temperature, a small viscosity, a suitable optical anisotropy, a large dielectric anisotropy and a suitable elastic constant. The composition has a suitable balance regarding at least two of physical properties. A liquid crystal display device of the invention includes the composition and has a wide temperature range in which the device can be used, a short response time, a large voltage holding ratio, a low threshold voltage, a large contrast ratio and a long service life. Accordingly, a wide application is allowed to the liquid crystal display device used in a personal computer, a television and so forth.

What is claimed is:

1. A compound, represented by formula (1):

(1)

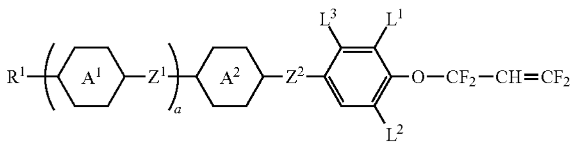

wherein, in formula (1), $R^1$ is alkyl having 1 to 15 carbons, and in the alkyl, at least one piece of $—CH_2—$ may be replaced by $—O—$, and at least one piece of $—CH_2CH_2—$ may be replaced by $—CH{=}CH—$, and in the groups, at least one piece of hydrogen may be replaced by halogen;

ring $A^1$ and ring $A^2$ are independently 1,4-cyclohexylene, 1,4-cyclohexenylene, 1,4-phenylene, 1,4-phenylene in which at least one piece of hydrogen is replaced by halogen, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl;

$Z^1$ and $Z^2$ are independently a single bond, $—CH_2CH_2—$, $—C{\equiv}C—$, $—CH{=}CH—$, $—CF{=}CF—$, $—CF_2O—$, $—OCF_2—$, $—CH_2O—$, $—OCH_2—$, $—COO—$ or $—OCO—$;

$L^1$, $L^2$ and $L^3$ are independently hydrogen or halogen; and a is 0, 1, 2 or 3.

2. The compound according to claim 1, wherein, in formula (1), $R^1$ is alkyl having 1 to 15 carbons, alkenyl having 2 to 15 carbons, alkoxy having 1 to 14 carbons or alkenyloxy having 2 to 14 carbons.

3. The compound according to claim 1, wherein, in formula (1), $Z^1$ and $Z^2$ are independently a single bond, $—CH_2CH_2—$, $—C{\equiv}C—$, $—CH{=}CH—$, $—CF_2O—$ or $—COO—$.

4. The compound according to claim 1, represented by any one of formulas (1-1) to (1-4):

(1-1)

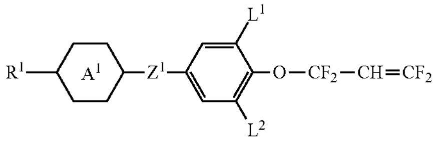

(1-2)

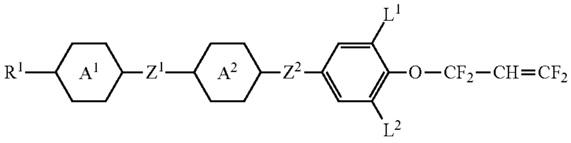

(1-3)

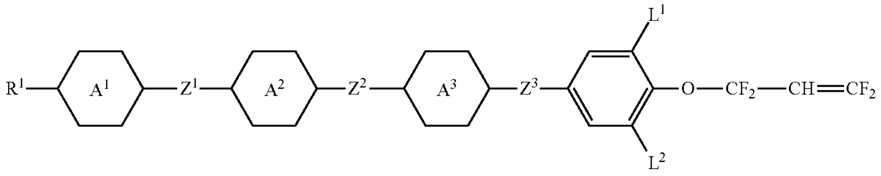

(1-4)

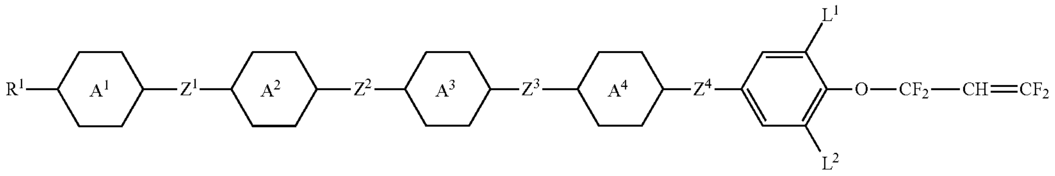

wherein, in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by halogen, tetrahydropyran-2,5-diyl, 1,3-dioxane-2,5-diyl or 2,6,7-trioxabicyclo[2.2.2]octane-1,4-diyl;

$Z^1$, $Z^2$, $Z^3$ and $Z^4$ are independently a single bond, $—CH_2CH_2—$, $—CH{=}CH—$, $—CF_2O—$ or $—COO—$;

$R^1$ is alkyl having 1 to 10 carbons or alkenyl having 2 to 10 carbons; and $L^1$ and $L^2$ are independently hydrogen or halogen.

5. The compound according to claim 4, wherein, in formulas (1-1) to (1-4), ring $A^1$, ring $A^2$, ring $A^3$ and ring $A^4$ are independently 1,4-cyclohexylene, 1,4-phenylene, 1,4-phenylene in which at least one piece of hydrogen is replaced by fluorine or chlorine, tetrahydropyran-2,5-diyl or 1,3-dioxane-2,5-diyl;

$Z^1$, $Z^2$, $Z^3$ and $Z^4$ are independently a single bond, $—CH_2CH_2—$, $—CH{=}CH—$ or $—CF_2O—$;

$R^1$ is alkyl having 1 to 10 carbons or alkenyl having 2 to 10 carbons; and $L^1$ and $L^2$ are independently hydrogen or fluorine (1-1)
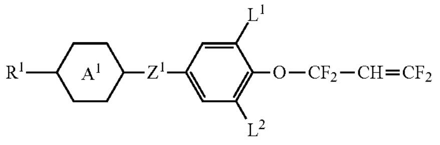
(1-2)
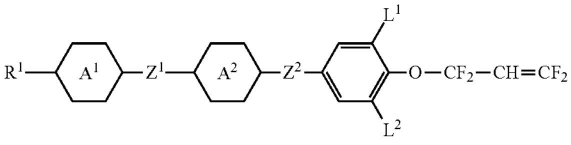
(1-3)
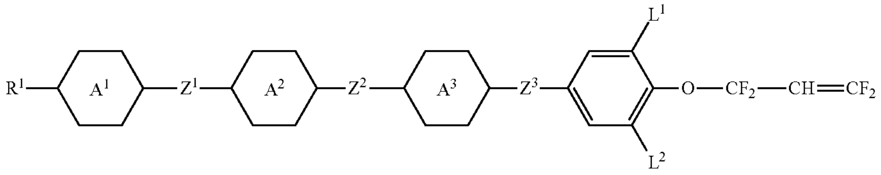
(1-4)
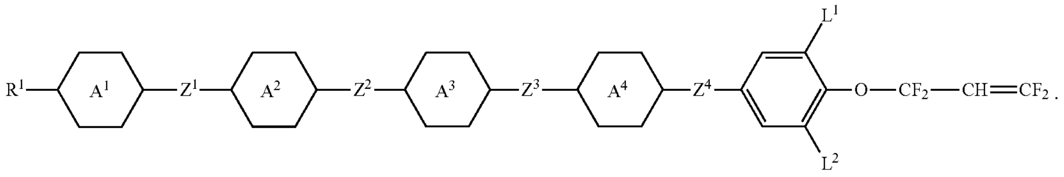
6. The compound according to claim 1, represented by any one of formulas (1-5) to (1-12):
(1-5)
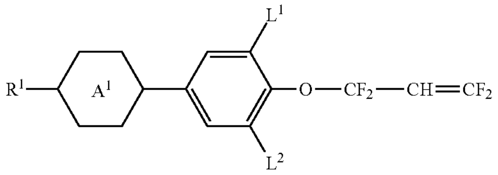
(1-6)
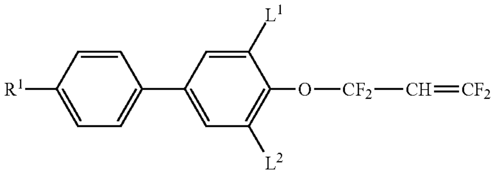
(1-7)
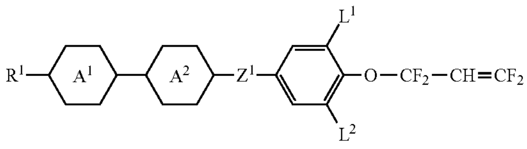
(1-8)
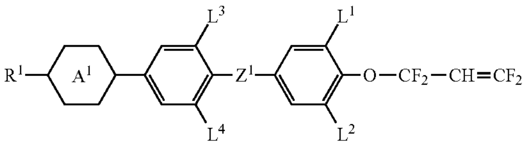
(1-9)
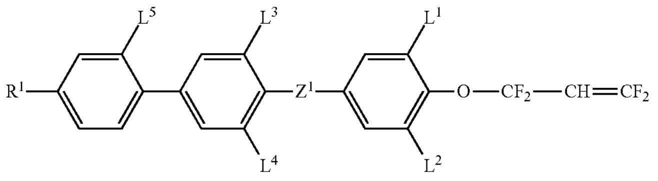
(1-10)
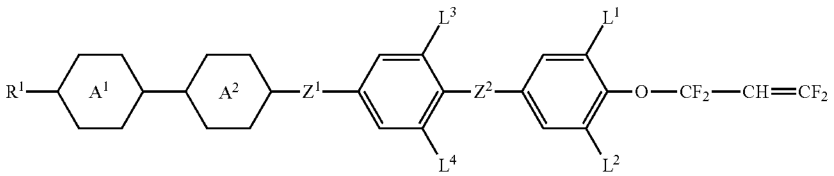
(1-11)
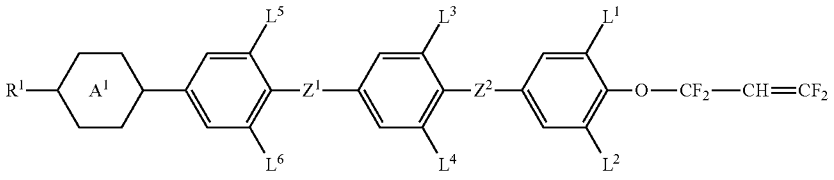

-continued (1-12)

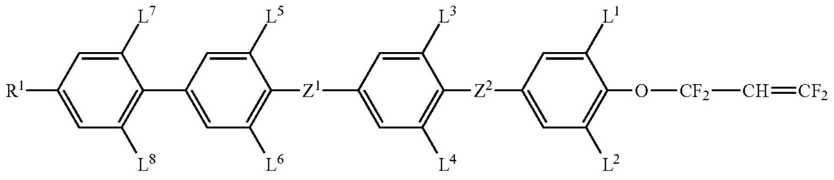

wherein, in formulas (1-5) to (1-12), ring $A^1$ and ring $A^2$ are independently 1,4-cyclohexylene, tetrahydropyran-2,5-diyl or 1,3-dioxane-2,5-diyl;

$Z^1$ and $Z^2$ are independently a single bond or —$CF_2O$—;

$R^1$ is alkyl having 1 to 10 carbons or alkenyl having 2 to 10 carbons; and $L^1$, $L^2$, $L^3$, $L^4$, $L^5$, $L^6$, $L^7$ and $L^8$ are independently hydrogen or fluorine.

7. The compound according to claim 1, represented by any one of formulas (1-13) to (1-23):

(1-13)

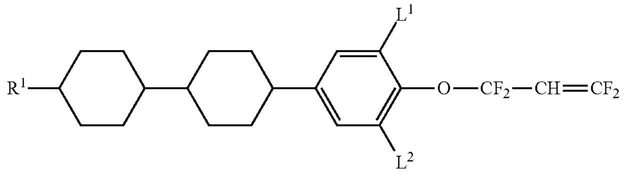

(1-14)

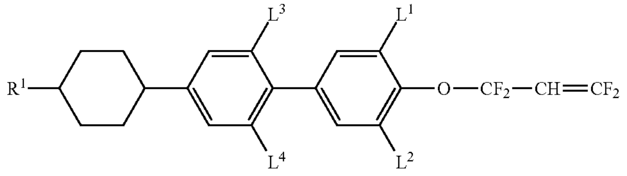

(1-15)

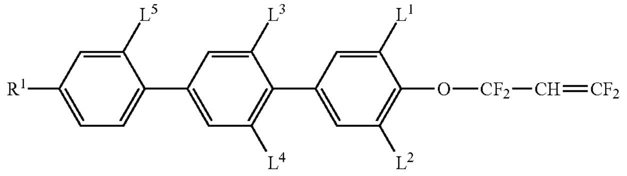

(1-16)

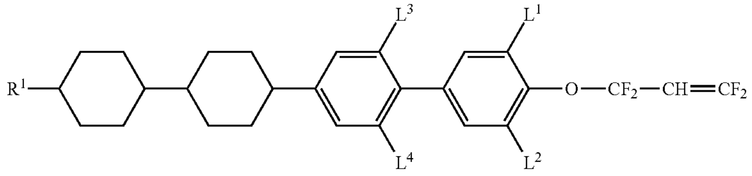

(1-17)

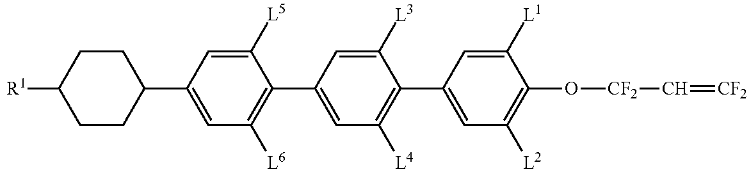

(1-18)

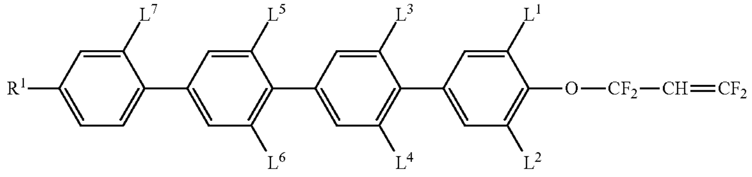

-continued (1-19)

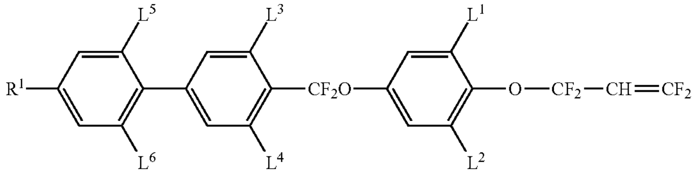

(1-20)

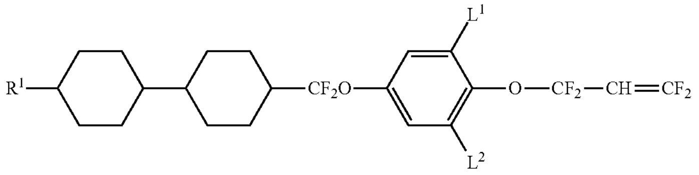

(1-21)

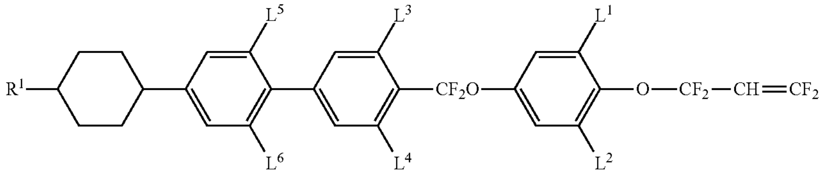

(1-22)

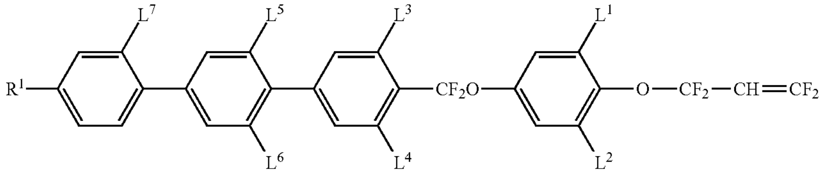

(1-23)

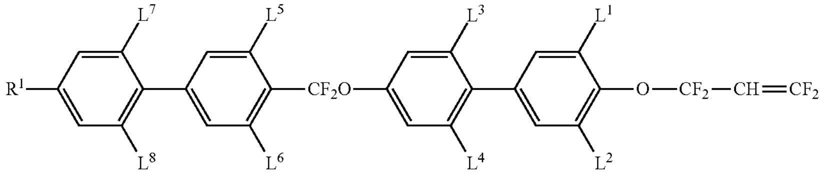

wherein, in formulas (1-13) to (1-23), $R^1$ is alkyl having 1 to 10 carbons or alkenyl having 2 to 10 carbons; and $L^1$, $L^2$, $L^3$, $L^4$, $L^5$, $L^6$, $L^7$ and $L^8$ are independently hydrogen or fluorine.

8. A liquid crystal composition, containing at least one of the compounds according to claim 1.

9. The liquid crystal composition according to claim 8, further containing at least one compound selected from the group of compounds represented by formulas (2) to (4):

(2)

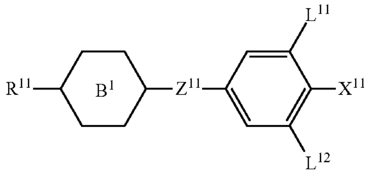

-continued (3)

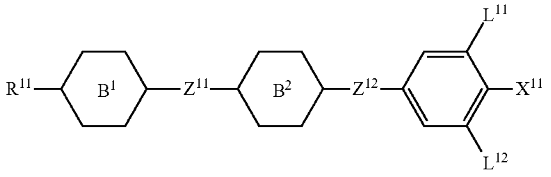

(4)

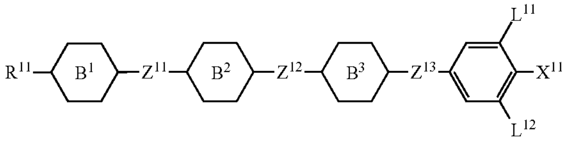

wherein, in formulas (2) to (4), $R^{11}$ is alkyl having 1 to 10 carbons or alkenyl having 2 to 10 carbons, and in the alkyl and the alkenyl, at least one piece of hydrogen may be replaced by fluorine, and at least one piece of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

10. The liquid crystal composition according to claim 8, further containing at least one compound selected from the group of compounds represented by formula (5):

(5)

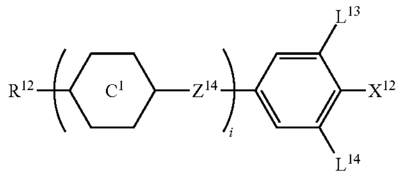

wherein, in formula (5), $R^{12}$ is alkyl having 1 to 10 carbons or alkenyl having 2 to 10 carbons, and in the alkyl and the alkenyl, at least one piece of hydrogen may be replaced by fluorine, and at least one piece of —$CH_2$— may be replaced by —O—;

$X^{12}$ is —C≡N or —C≡C—C≡N;

ring $C^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

11. The liquid crystal composition according to claim 8, further containing at least one compound selected from the group of compounds represented by formulas (6) to (12):

(6)

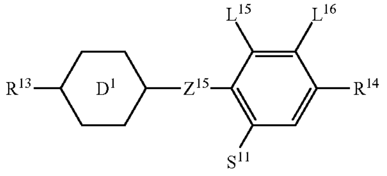

(7)

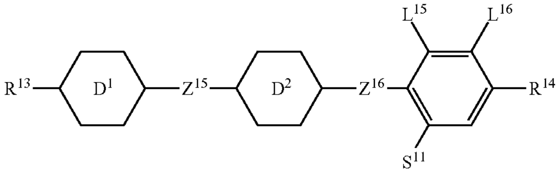

(8)

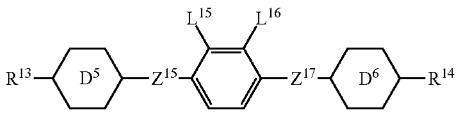

(9)

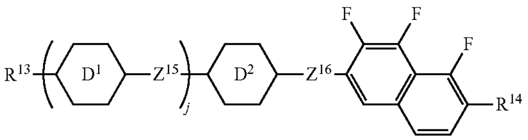

(10)

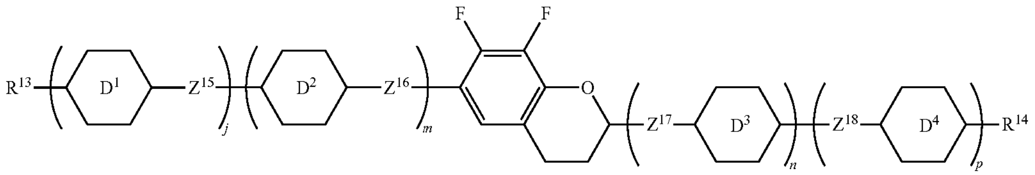

(11)

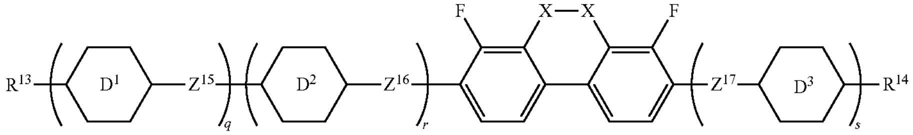

(12)

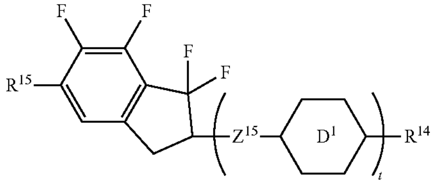

wherein, in formulas (6) to (12), $R^{13}$ and $R^{14}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$R^{15}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$S^{11}$ is hydrogen or methyl;

X is —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

12. The liquid crystal composition according to claim 8, further containing at least one compound selected from the group of compounds represented by formulas (13) to (15):

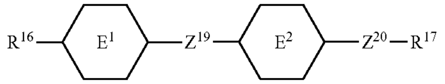

(13)

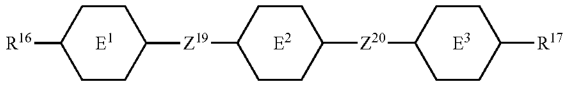

(14)

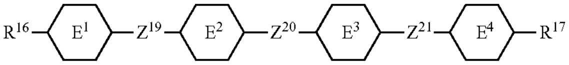

(15)

wherein, in formulas (13) to (15), $R^{16}$ and $R^{17}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

13. The liquid crystal composition according to claim 8, further containing at least one selected from a polymerizable compound, an optically active compound, an antioxidant, an ultraviolet light absorber, a light stabilizer, a heat stabilizer and an antifoaming agent.

14. A liquid crystal display device, including the liquid crystal composition according to claim 8.

* * * * *